(12) United States Patent
Tsien et al.

(10) Patent No.: US 11,246,940 B2
(45) Date of Patent: Feb. 15, 2022

(54) PEPTIDES WHOSE UPTAKE IN CELLS IS CONTROLLABLE

(71) Applicant: The Regents of the University of California, Oakland, CA (US)

(72) Inventors: Roger Tsien, La Jolla, CA (US); Todd Aguilera, San Diego, CA (US); Emilia Olson, Seattle, WA (US); Tao Jiang, San Diego, CA (US); Quyen Nguyen, Del Mar, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/457,763

(22) Filed: Jun. 28, 2019

(65) Prior Publication Data

US 2020/0046843 A1  Feb. 13, 2020

Related U.S. Application Data

(63) Continuation of application No. 15/427,427, filed on Feb. 8, 2017, now abandoned, which is a continuation of application No. 13/384,591, filed as application No. PCT/US2010/042184 on Jul. 15, 2010, now Pat. No. 9,682,151.

(60) Provisional application No. 61/225,872, filed on Jul. 15, 2009.

(51) Int. Cl.
| | |
|---|---|
| *A61K 47/64* | (2017.01) |
| *A61K 49/00* | (2006.01) |
| *C07K 7/06* | (2006.01) |
| *A61K 47/60* | (2017.01) |
| *A61K 47/59* | (2017.01) |
| *A61K 47/62* | (2017.01) |
| *A61K 47/69* | (2017.01) |

(52) U.S. Cl.
CPC ............ *A61K 47/64* (2017.08); *A61K 47/595* (2017.08); *A61K 47/60* (2017.08); *A61K 47/62* (2017.08); *A61K 47/6911* (2017.08); *A61K 49/0032* (2013.01); *A61K 49/0056* (2013.01); *C07K 7/06* (2013.01)

(58) Field of Classification Search
CPC ........ A61K 47/00; A61K 47/60; A61K 47/64; A61K 47/595; A61K 47/62; A61K 47/6911; A61K 49/00; A61K 49/0032; A61K 49/0056; C07K 7/06; A61P 9/00; A61P 35/00
USPC ........ 424/1.11, 1.65, 1.69, 9.1, 9.2, 9.3, 9.4, 424/9.5, 9.6; 514/1, 1.1; 530/300, 324, 530/325, 326, 327, 328, 329
See application file for complete search history.

(56) References Cited

U.S. PATENT DOCUMENTS

| | | | |
|---|---|---|---|
| 7,985,401 B2* | 7/2011 | Jiang | A61K 41/0095 424/1.69 |
| 8,110,554 B2* | 2/2012 | Jiang | A61K 49/0056 514/21.6 |
| 8,642,561 B2* | 2/2014 | Jiang | A61K 47/65 514/21.6 |
| 9,072,792 B2* | 7/2015 | Jiang | C07K 7/08 |
| 9,682,151 B2* | 6/2017 | Tsien | A61K 49/0032 |
| 9,808,532 B2* | 11/2017 | Tsien | C07K 7/06 |
| 10,259,845 B2* | 4/2019 | Jiang | A61K 47/65 |

FOREIGN PATENT DOCUMENTS

WO  WO-2006125134 A1 * 11/2006 ............. A61K 47/64

* cited by examiner

*Primary Examiner* — D. L. Jones
(74) *Attorney, Agent, or Firm* — Morgan, Lewis & Bockius, LLP; Christina A. MacDougall

(57) ABSTRACT

Disclosed herein, in certain embodiments, is a selective transport molecule with increased in vivo circulation. In some embodiments, a selective transport molecule disclosed herein has the formula (A-X-B-C)-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and M is a macromolecular carrier.

13 Claims, 40 Drawing Sheets
Specification includes a Sequence Listing.

A. Thioether

Aromatic

Urea

Peg

B.

A.

B.

A.

B.

C.

D.

A.

B.

C.

D.

PEPTIDES WHOSE UPTAKE IN CELLS IS CONTROLLABLE

CROSS-REFERENCE

This application is a Continuation of U.S. application Ser. No. 15/427,427, filed Feb. 8, 2017, which is a Continuation of U.S. application Ser. No. 13/384,591, filed Feb. 16, 2012, now U.S. Pat. No. 9,682,151, which is a 371 of PCT/US2010/042184, filed Jul. 15, 2010, which claims the benefit of U.S. Provisional Application No. 61/225,872, filed Jul. 15, 2009, which applications are incorporated herein by reference in its entirety.

STATEMENT AS TO FEDERALLY SPONSORED RESEARCH

This invention was made with governmental support under grant no. W81XWH-05-1-0183 awarded by the US Army Department of Defense, and grant no. NIBIB-K08 EB008122 awarded by the NIH. The government has certain rights in the invention.

REFERENCE TO A "SEQUENCE LISTING," A TABLE, OR A COMPUTER PROGRAM, LISTING APPENDIX SUBMITTED ON A COMPACT DISK

This invention incorporated by reference the Sequence Listing text copy submitted herewith, which was created on Oct. 22, 2019, entitled 008075-5007-US11-Sequence-Listing.txt which is 17,992 bytes in size.

BACKGROUND OF THE INVENTION

Cell membranes delimit the outer boundaries of cells, and regulate transport into and out of the cell interior. Made primarily of lipids and proteins, they provide a hydrophilic surface enclosing a hydrophobic interior across which materials must pass before entering a cell. Although many small, lipophilic compounds are able to cross cell membranes passively, most compounds, particles and materials must rely on active mechanisms in order to gain entry into a living cell.

SUMMARY OF THE INVENTION

Disclosed herein, in certain embodiments, is a molecule of the structure (A-X-B-C)-M, wherein
C is at least one imaging agent;
A is a peptide with a sequence comprising 5 to 9 consecutive acidic amino acids, wherein the amino acids are selected from: aspartates and glutamates;
B is a peptide with a sequence comprising 5 to 20 consecutive basic amino acids;
X is a linker; and
M is a macromolecular carrier;
wherein M is bound to A or B.

In some embodiments, A has a sequence comprising 5 to 9 consecutive glutamates. In some embodiments, B has a sequence comprising 5 to 12 consecutive arginines. In some embodiments, B has a sequence comprising 9 consecutive arginines. In some embodiments, (a) A has a sequence comprising 8 to 9 consecutive glutamates and (b) B has a sequence comprising 9 consecutive arginines. In some embodiments, A and B comprise D-amino acids. In some embodiments, X is a cleavable linker. In some embodiments, X comprises a peptide linkage. In some embodiments, X comprises 6-aminohexanoyl, 5-amino-3-oxapentanoyl, or a combination thereof. In some embodiments, X comprises a disulfide linkage. In some embodiments, X is about 6 to about 30 atoms in length. In some embodiments, X is a pH-sensitive linker. In some embodiments, X is cleaved in the extracellular space. In some embodiments, X is cleaved by a protease, a matrix metalloproteinase, or a combination thereof. In some embodiments, X is cleaved by a reducing agent. In some embodiments, the X is selected from: PLGLAG (SEQ ID NO: 1), PLGLAx (SEQ ID NO: 2) wherein X is any amino acid, PLG-C(me)-AG (SEQ ID NO: 3), ESPAYYTA (SEQ ID NO: 4), and RLQLKL (SEQ ID NO: 5), AND RLQLK(AC) (SEQ ID NO: 6). In some embodiments, M is a macromolecular carrier selected from: a dendrimer, dextran, a PEG polymer, or albumin. In some embodiments, M is a PEG polymer. In some embodiments, C comprises an imaging agent, a therapeutic agent, or a combination thereof. In some embodiments, C comprises an imaging agent selected from: a fluorescent moiety, a luminescent moiety, a phosphorescent moiety, a fluorescence-quenching moiety, a radioactive moiety, a radiopaque moiety, a paramagnetic moiety, a contrast agent, or a combination thereof. In some embodiments, C comprises a therapeutic agent selected from: a chemotherapeutic agent, a radiation sensitizer, an agent that modulates apoptosis, and agent that modulates the cell cycle, an agent that modulates a signaling cascade, or a combination thereof. In some embodiments, the cargo is an indocarbocyanine dye. In some embodiments, the cargo is indocarbocyanine dye, Cy5, Cy5.5, Cy7, IRDYE 800CW, ALEXA647, or a combination thereof. In some embodiments, the cargo is an MRI contrast agent. In some embodiments, the cargo is Gd complex of [4,7,10-tris(carboxymethyl)-1,4,7,10-tetraazacyclododec-1-yl]acetyl.

Disclosed herein, in certain embodiments, is a molecule of the structure $(A-X-B)_n$-L, wherein
L comprises a lipid or lipid-coated therapeutic agent or imaging agent;
A is a peptide with a sequence comprising 5 to 9 consecutive acidic amino acids, wherein the amino acids are selected from: aspartates and glutamates;
B is a peptide with a sequence comprising 5 to 20 consecutive basic amino acids;
X is a linker; and
n is an integer between 1 and 20; and
wherein L is attached to an (A-X-B) moiety by a bond with a B.

In some embodiments, A has a sequence comprising 5 to 9 consecutive glutamates. In some embodiments, B has a sequence comprising 5 to 12 consecutive arginines. In some embodiments, B has a sequence comprising 9 consecutive arginines. In some embodiments, (a) A has a sequence comprising 8 to 9 consecutive glutamates and (b) B has a sequence comprising 9 consecutive arginines. In some embodiments, A and B comprise D-amino acids. In some embodiments, X is a cleavable linker. In some embodiments, X comprises a peptide linkage. In some embodiments, X comprises 6-aminohexanoyl, 5-(amino)-3-oxapentanoic acid, or a combination thereof. In some embodiments, X comprises a disulfide linkage. In some embodiments, X is about 6 to about 30 atoms in length. In some embodiments, X is a pH-sensitive linker. In some embodiments, X is cleaved in the extracellular space. In some embodiments, X is cleaved by a protease, a matrix metalloproteinase, or a combination thereof. In some embodiments, X is cleaved by a reducing agent. In some embodiments, the X is selected from: PLGLAG (SEQ ID NO: 1), PLGLAx (SEQ ID NO: 2) wherein x is any amino acid, PLG-C(me)-AG (SEQ ID NO: 3), ESPAYYTA (SEQ ID NO: 4), and RLQLKL (SEQ ID NO: 5), AND RLQLK(AC) (SEQ ID NO: 6). In some embodiments, the lipid is PEGylated. In some embodiments, the lipid is PEG(2K)-phosphatidylethanolamine. In some embodiments, the therapeutic agent is hydrophobic. In some embodiments, the therapeutic agent is selected from: a chemotherapeutic agent, a radiation sensitizer, an agent that modulates apoptosis, and agent that modulates the cell cycle, an agent that modulates a signaling cascade, or a combination thereof. In some embodiments, the therapeutic agent is doxorubicin or paclitaxel.

Disclosed herein, in certain embodiments, is a molecule of the structure $(A-X-B)_n$-D, wherein D is a dendrimer;
  A is a peptide with a sequence comprising 5 to 9 consecutive acidic amino acids, wherein the amino acids are selected from: aspartates and glutamates;
  B is a peptide with a sequence comprising 5 to 20 consecutive basic amino acids;
  X is a linker; and
  N is an integer between 1 and 20; and
  wherein D is attached to an (A-X-B) moiety by a bond with a B.
In some embodiments, D comprises at least one cargo moiety. In some embodiments, the at least one cargo moiety is an imaging agent, a therapeutic agent, or a combination thereof. In some embodiments, the at least one cargo moiety is an imaging agent selected from: a fluorescent moiety, a luminescent moiety, a phosphorescent moiety, a fluorescence-quenching moiety, a radioactive moiety, a radiopaque moiety, a paramagnetic moiety, a contrast agent, or a combination thereof. In some embodiments, the at least one cargo moiety is a therapeutic agent selected from: a chemotherapeutic agent, a radiation sensitizer, an agent that modulates apoptosis, and agent that modulates the cell cycle, an agent that modulates a signaling cascade, or a combination thereof. In some embodiments, the at least one cargo moiety is an indocarbocyanine dye. In some embodiments, the at least one cargo moiety is indocarbocyanine dye, Cy5, Cy5.5, Cy7, IRDYE 800CW, ALEXA647, or a combination thereof. In some embodiments, the at least one cargo moiety is an MRI contrast agent. In some embodiments, the at least one cargo moiety is Gd complex of [4,7,10-tris(carboxymethyl)-1,4,7,10-tetraazacyclododec-1-yl]acetyl. In some embodiments, A has a sequence comprising 5 to 9 consecutive glutamates. In some embodiments, B has a sequence comprising 5 to 12 consecutive arginines. In some embodiments, B has a sequence comprising 9 consecutive arginines. In some embodiments, (a) A has a sequence comprising 8 to 9 consecutive glutamates and (b) B has a sequence comprising 9 consecutive arginines. In some embodiments, A and B comprise D-amino acids. In some embodiments, X is a cleavable linker. In some embodiments, X comprises a peptide linkage. In some embodiments, X comprises 6-aminohexanoyl, 5-(amino)-3-oxapentanoic acid, or a combination thereof. In some embodiments, X comprises a disulfide linkage. In some embodiments, X is about 6 to about 30 atoms in length. In some embodiments, X is a pH-sensitive linker. In some embodiments, X is cleaved in the extracellular space. In some embodiments, X is cleaved by a protease, a matrix metalloproteinase, or a combination thereof. In some embodiments, X is cleaved by a reducing agent. In some embodiments, the X is selected from: PLGLAG (SEQ ID NO: 1), PLGLAx (SEQ ID NO: 2) wherein x is any amino acid, PLG-C(me)-AG (SEQ ID NO: 3), ESPAYYTA (SEQ ID NO: 4), and RLQLKL (SEQ ID NO: 5), AND RLQLK(AC) (SEQ ID NO: 6).

Disclosed herein, in certain embodiments, is a method of imaging a tumor in a subject, comprising imaging the tumor after the subject has been administered a molecule of the structure (A-X-B-C)-M, wherein
  C is at least one imaging agent;
  A is a peptide with a sequence comprising 5 to 9 consecutive acidic amino acids, wherein the amino acids are selected from: aspartates and glutamates;
  B is a peptide with a sequence comprising 5 to 20 consecutive basic amino acids;
  X is a linker; and
  M is a macromolecular carrier;
wherein M is bound to A or B.

Disclosed herein, in certain embodiments, is a use of a molecule to of structure (A-X-B-C)-M for imaging a tumor in a subject in need thereof, wherein
  C is at least one imaging agent;
  A is a peptide with a sequence comprising 5 to 9 consecutive acidic amino acids, wherein the amino acids are selected from: aspartates and glutamates;
  B is a peptide with a sequence comprising 5 to 20 consecutive basic amino acids;
  X is a linker; and
  M is a macromolecular carrier;
wherein M is bound to A or B.

Disclosed herein, in certain embodiments, is a method of imaging the surgical margins for a tumor or tissue resection in a subject, comprising imaging the surgical margins after the subject has been administered a molecule of the structure (A-X-B-C)-M, wherein
  C is at least one imaging agent;
  A is a peptide with a sequence comprising 5 to 9 consecutive acidic amino acids, wherein the amino acids are selected from: aspartates and glutamates;
  B is a peptide with a sequence comprising 5 to 20 consecutive basic amino acids;
  X is a linker; and
  M is a macromolecular carrier;
wherein M is bound to A or B.

Disclosed herein, in certain embodiments, is a use of a molecule to of structure (A-X-B-C)-M to image the surgical margins for a tumor or tissue resection in a subject in need thereof, wherein
  C is at least one imaging agent;
  A is a peptide with a sequence comprising 5 to 9 consecutive acidic amino acids, wherein the amino acids are selected from: aspartates and glutamates;
  B is a peptide with a sequence comprising 5 to 20 consecutive basic amino acids;
  X is a linker; and
  M is a macromolecular carrier;
wherein M is bound to A or B.

Disclosed herein, in certain embodiments, is a method of removing a tumor in a subject, comprising removing the tumor after the subject has been administered a molecule of the structure (A-X-B-C)-M, wherein
  C is at least one imaging agent;
  A is a peptide with a sequence comprising 5 to 9 consecutive acidic amino acids, wherein the amino acids are selected from: aspartates and glutamates;
  B is a peptide with a sequence comprising 5 to 20 consecutive basic amino acids;
  X is a linker; and
  M is a macromolecular carrier; and
  wherein M is bound to A or B.

Disclosed herein, in certain embodiments, is a use of a molecule to of structure (A-X-B-C)-M for removing a tumor from a subject in need thereof, wherein C is at least one imaging agent;
A is a peptide with a sequence comprising 5 to 9 consecutive acidic amino acids, wherein the amino acids are selected from: aspartates and glutamates;
B is a peptide with a sequence comprising 5 to 20 consecutive basic amino acids;
X is a linker; and
M is a macromolecular carrier;
wherein M is bound to A or B.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

(B) shows relative intensity of tumor and a background region drawn over the thorax. For ease of comparison, the top background value has been normalized to one. (C) and (D) show similar data for the succinyl capped compound.

Figure 33:
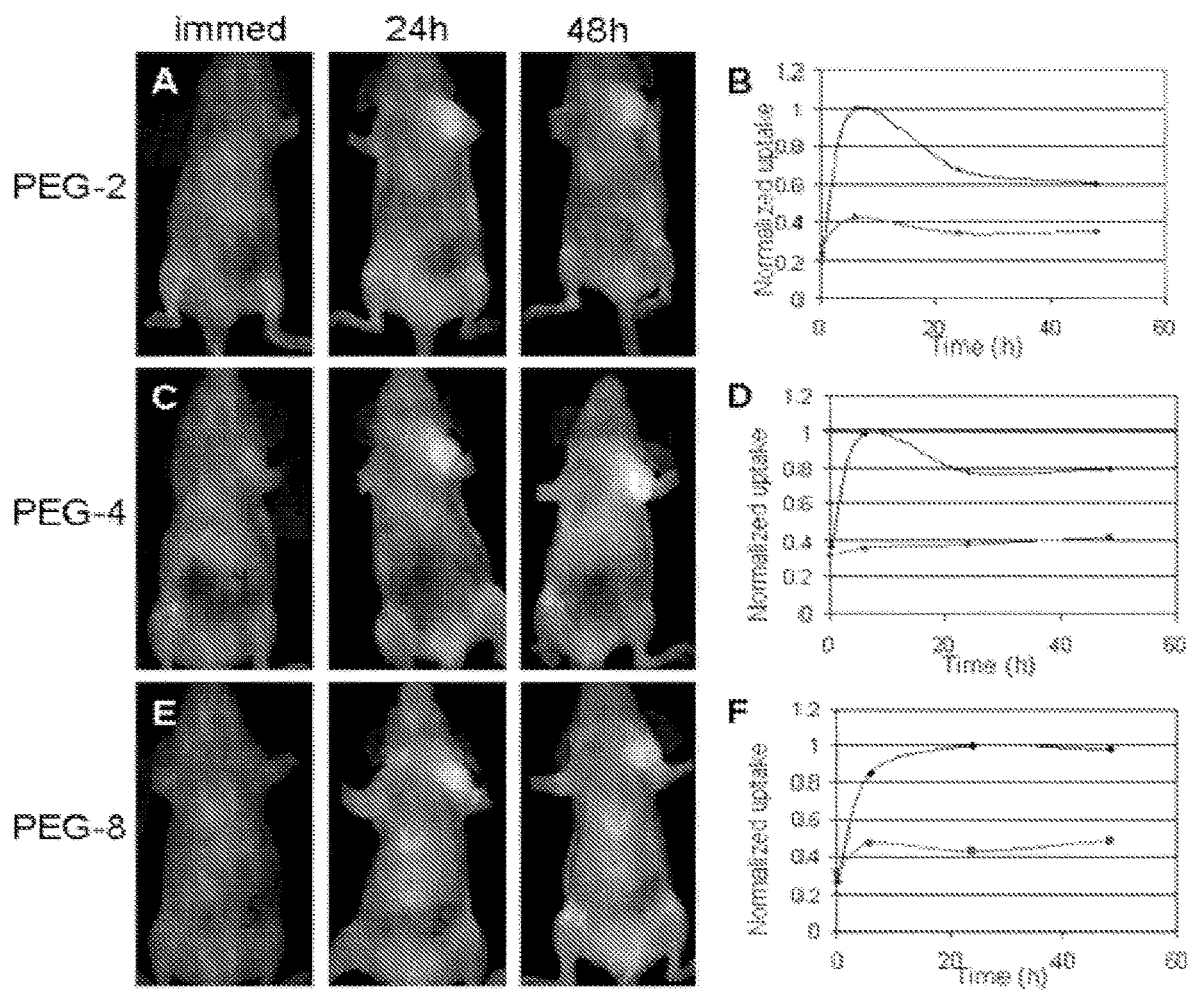

FIG. 33. Exemplary in vivo images for mice injected with PEG-2, PEG-4, PEG-8 and PEG-12 capped dendrimers. (A) shows images of a mouse immediately post, 24 h post and 48 hours post injection with an PEG-2 capped dendrimer. Fluorescence dissection images are shown and labeled T (tumor), L (liver) and K (kidney). (B) shows intensity of tumor and a background region drawn over the thorax. For ease of comparison, the top background value has been normalized to one. (C) and (D) show similar data for the PEG-4 capped compound, and (E) and (F) show similar data for the PEG-8 capped compound. PEG-12 behaved similarly to PEG-8.

Figure 34:
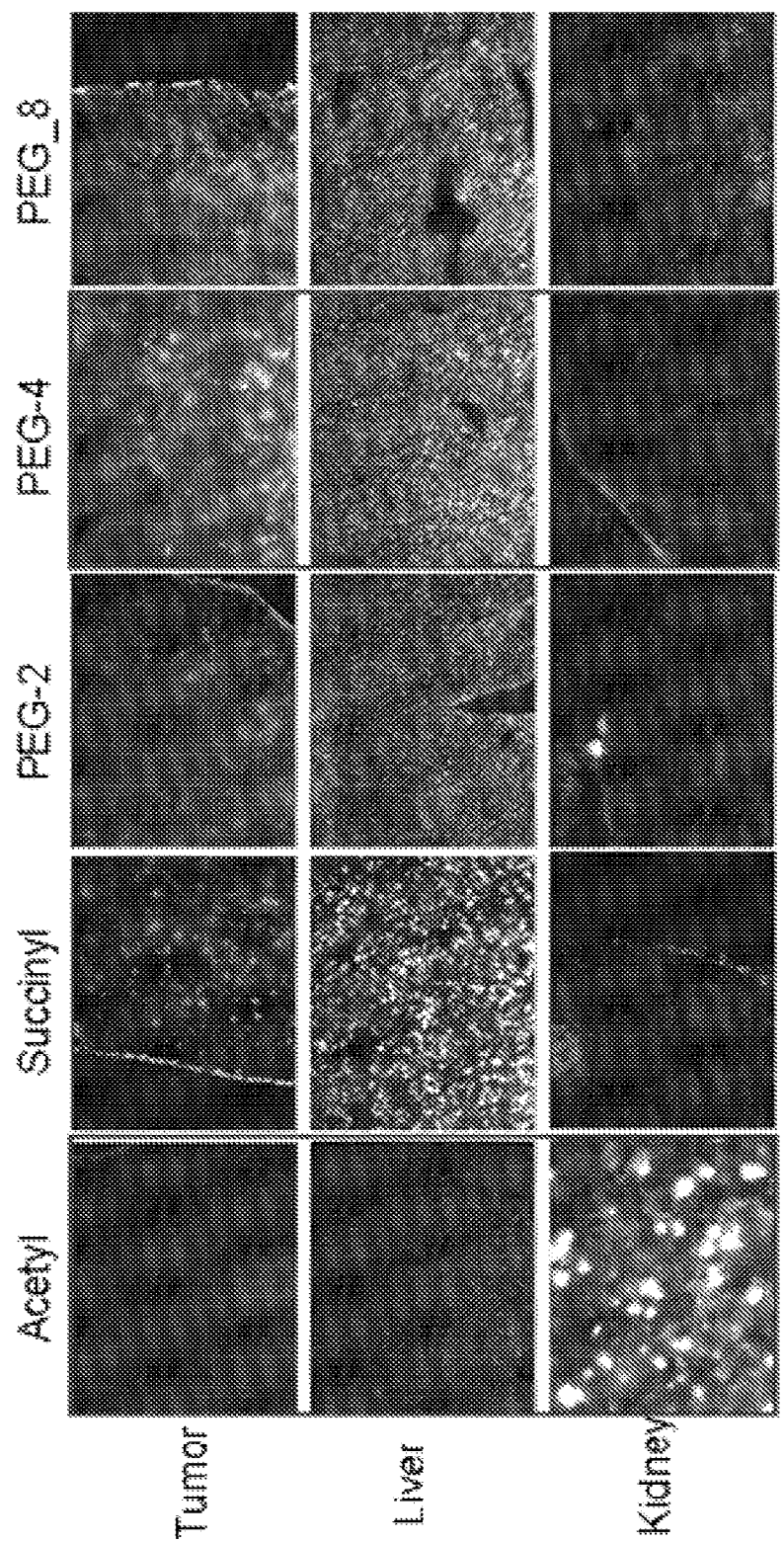

FIG. 34. Organ histology for dendrimers with the indicated cap.

Figure 35:
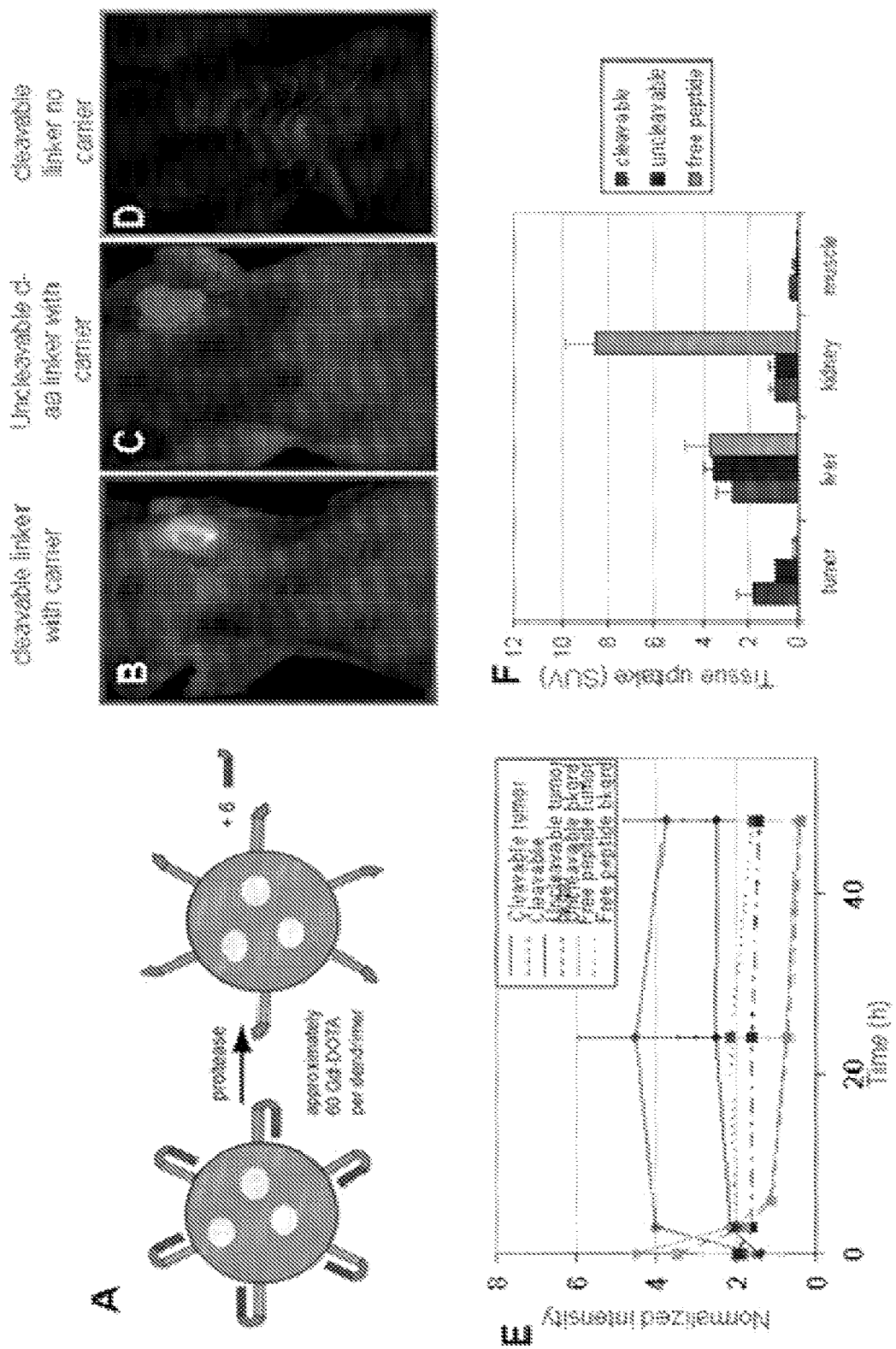

FIG. 35. Selective transport molecules conjugated to dendrimeric nanoparticles cause localized uptake in tumors that stays put even after 48 h. (A) shows a schematic of the new molecules. Selective transport molecules are linked via the polycation. Upon cleavage, the polyanion is released, leaving a highly charged molecule to stick to and enter cells. (B-D) show images 48 hours after injection with 10 nmol of the cy5. (E) shows a timelapse comparing skin values from animals injected with cleavable and all-d-amino acid Selective transport molecules conjugated to dendrimeric nanoparticles to that of an animal injected with a cleavable free peptide. (F) shows standardized uptake values comparing tumor, liver, kidney and muscle from the three peptides. Free peptide data is from a PLG-C(me)-AG (SEQ ID NO: 3) peptide after six hours (MeC=S-methylcysteine).

Figure 36:
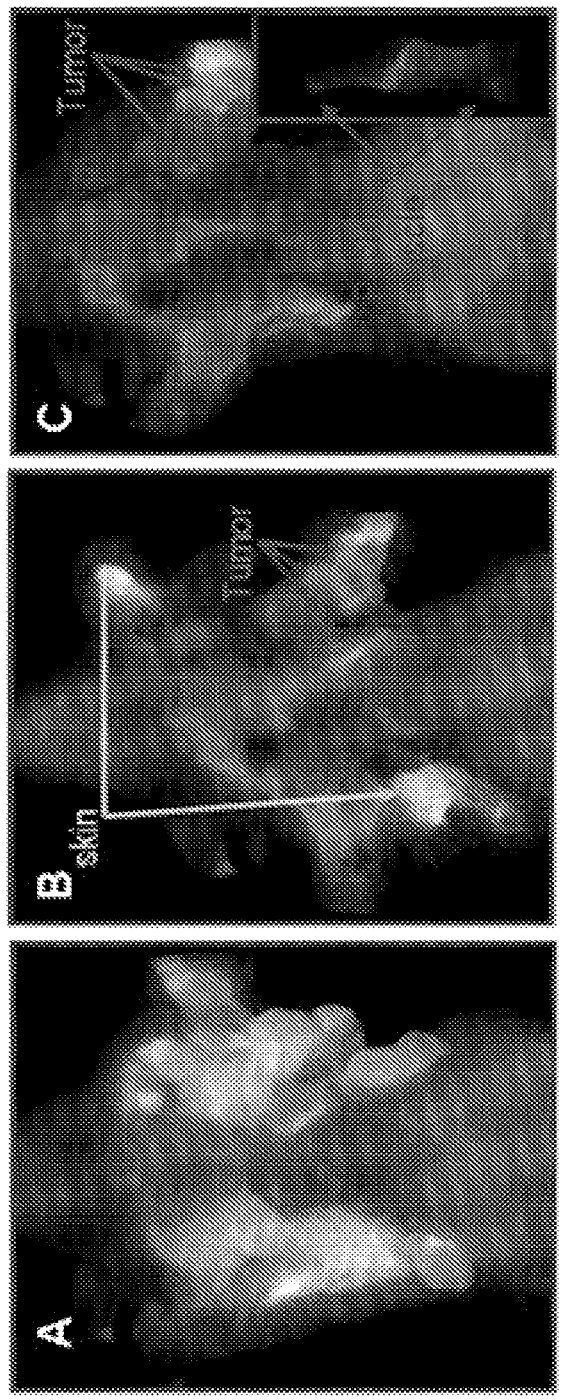
Figure 36:
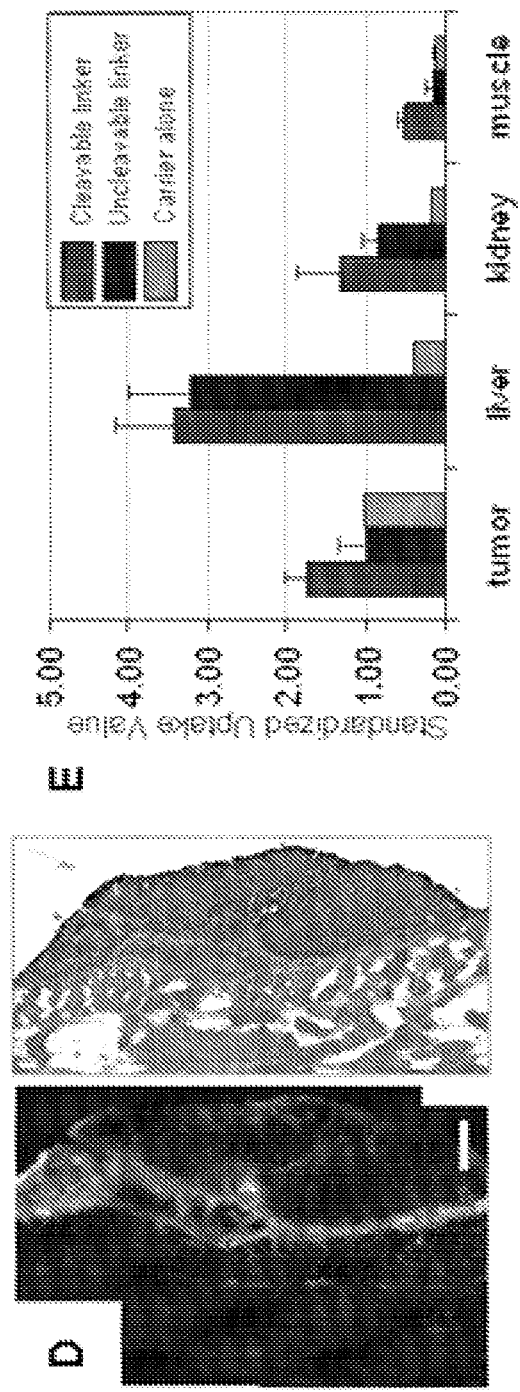

FIG. 36. Protease dependent uptake highlights residual tumor following injection of cleavable probe into MMTV-PyMT mice. (A) shows a PyMT mouse 48 hours following injection of probe and removal of skin. (B) shows the same mouse after gross removal of tumor. A strip of tumor on the pectoralis muscle remains. (C) shows the mouse following removal of the pectoralis muscle, with the muscle shown in the inset. Small pieces of residual tumor are present. (D) shows a cross section of the strip of tumor demonstrating an intense band of protease activation at the interface between tumor and pectoralis muscle. (E) shows standardized uptake values for the cleavable and all-d-amino acid probes compared to the PAMAM dendrimer alone in the MMTV-PyMT model.

Figure 37:
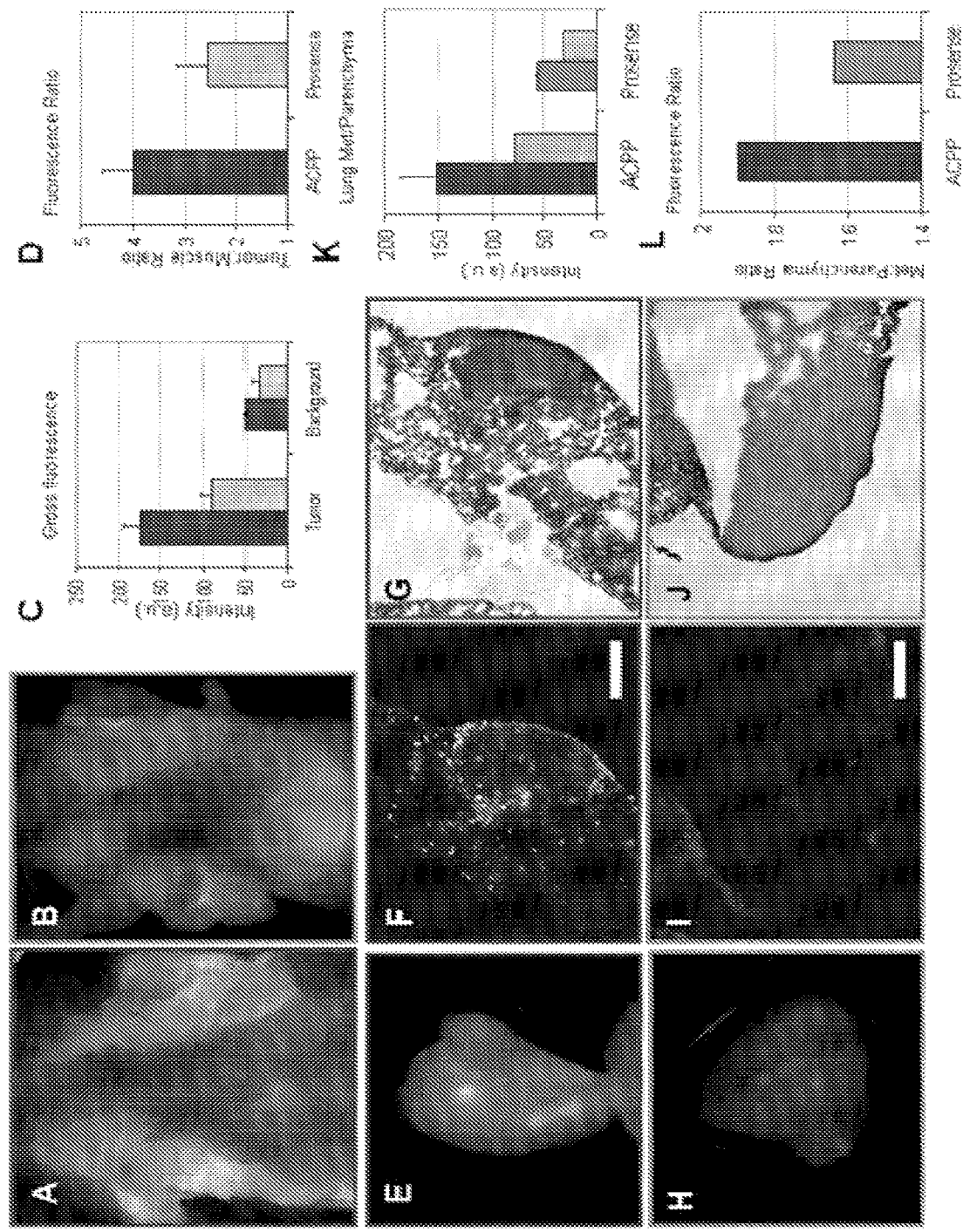

FIG. 37. Selective transport molecules conjugated to dendrimeric nanoparticles contrast agents are brighter and demonstrate more contrast than comparable dequenching agents. (A) and (B) show a representative mouse injected with either an selective transport molecule-bomb (A) or Prosense. A dequenching probe activated by intracellular cathepsins (B). Each mouse was sacrificed at the time deemed to give the best contrast (48 hours for selective transport molecules, 24 hours for Prosense as per the manufacturer's instruction). (C) shows gross fluroresence in tumor and background. (D) shows tumor to muscle ratios in PyMT mice injected with either an selective transport molecule-bomb or Prosense. (E-G) and (H-J) show gross images of and frozen section histology for lung metastases from the mice in (A) and (B) respectively. Scale bars are 200 um. (K) and (L) show quantitative uptake data and fluorescence ratios for the lung metastases shown in (E) and (H) respectively.

Figure 38:
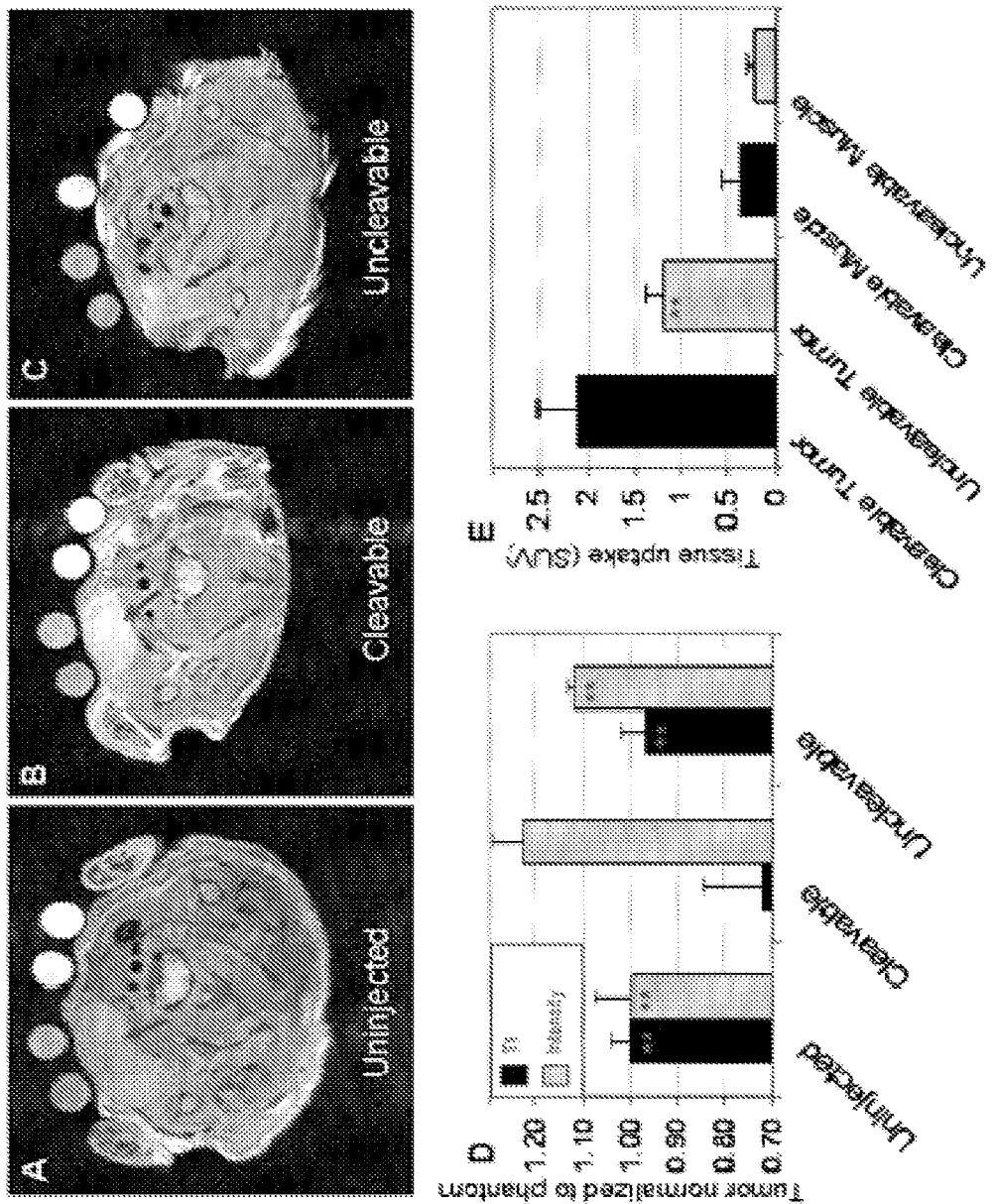

FIG. 38. Selective transport molecules conjugated to dendrimeric nanoparticles loaded with gadolinium allow visualization of protease activity by T1 MRI. (A) Images of animals bearing HT-1080 xenografts 48 hours post injection with no probe (left), (B) Images of animals bearing HT-1080 xenografts 48 hours post injection with an cleavable probe (PLG-C(me)-AG (SEQ ID NO: 3), middle) or (C) Images of animals bearing HT-1080 xenografts 48 hours post injection with an all-d-amino acid control probe (plg-(meC)ag, right). (D) shows measured differences in intensity and T1 for the cleavable and uncleavable probes relative to that of uninfected mice. Both T1 and relaxivity have been normalized to water phantom intensity to account for variability between scans. (E) shows standardized uptake values for gadolinium in tissue from animals injected with either the cleavable or all-d-amino acid control probe. Gadolinium was quantitated using ICPMS.

Figure 39:
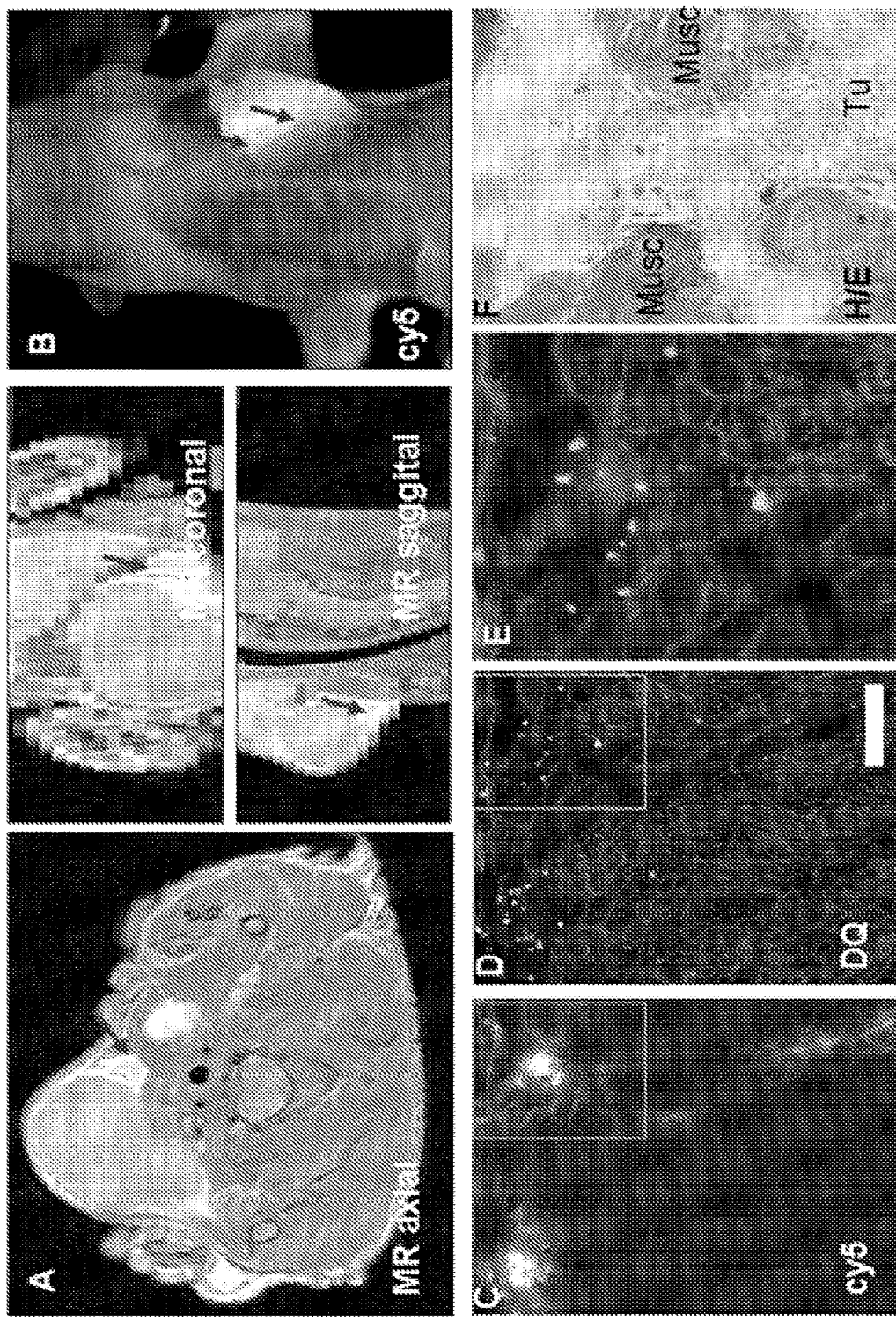

FIG. 39. Regions of tumor with high local gadolinium uptake correlate with macrophage mediated invasion of tumor into muscle. (A) Shows T1 weighted MR images showing infiltration of tumor into surrounding muscle. Axial, coronal and sagittal slices are shown. (B) shows a corresponding optical image. (C-F) (C) shows a histological section of the same tumor, imaged using cy5 fluorescence. (D) shows in situ zymography of the same slice. The scale bar denotes 200 μm. (E) shows a region of cy5 overlaid with the in situ zymography at higher power. (F) shows an H/E image of the region shown in (E) for identification purposes.

Figure 40:
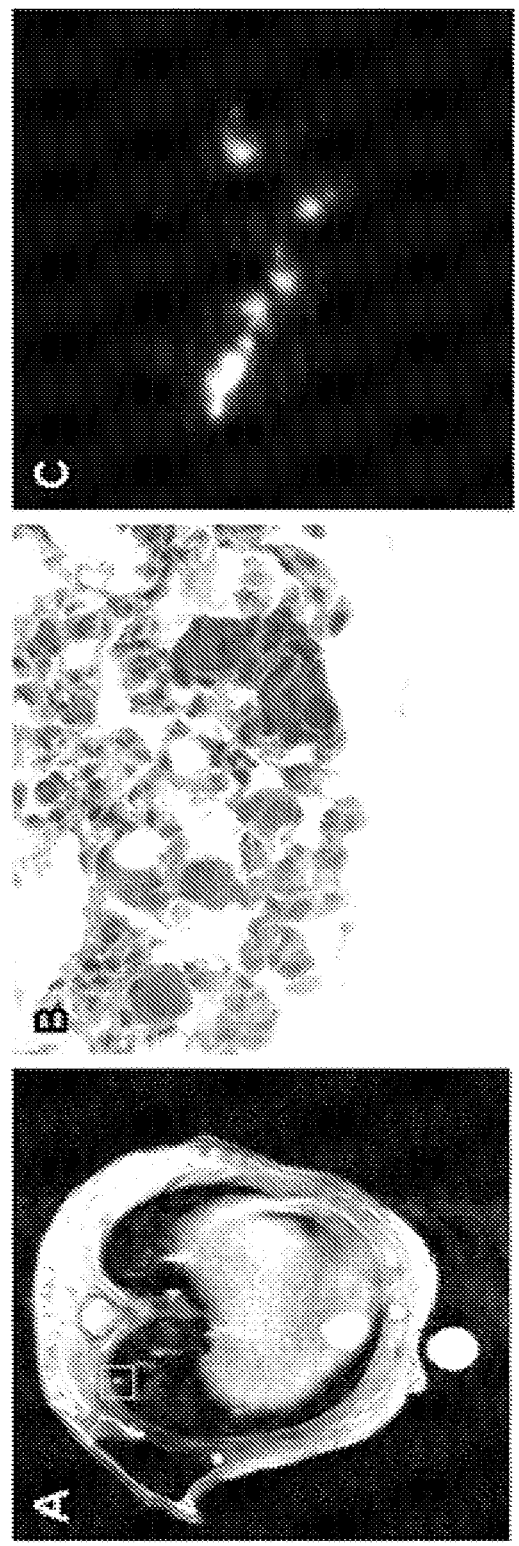

FIG. 40. Visualization of probe in lung using T1 MIII. The identity of the very bright cells is unknown.

DETAILED DESCRIPTION OF THE INVENTION

Selective transport molecules allow the targeted delivery of therapeutic agents and/or imaging agents to specific cells and/or tissues. Selective transport molecules comprise (a) a molecular transport sequence (portion B), (b) a cargo (portion C or D) bound to portion B and (c) an acidic portion A which is effective to inhibit or prevent the uptake into cells. Cleavage of linker X, allowing the separation of portion A from portion B, is effective to allow the uptake of portion B and the attached cargo into cells. However, selective transport molecules may be subject to rapid pharmacokinetic distribution with short plasma half-life, broad distribution, and slow wash out from multiple tissues with specific and non-specific uptake. Thus, there is a need for a selective transport molecule with increased in vivo circulation and modulated extravasation selectivity.

Disclosed herein, in certain embodiments, is a selective transport molecule with increased in vivo circulation.

In some embodiments, a selective transport molecule disclosed herein has the formula (A-X-BC)-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and M is a macromolecular carrier.

In some embodiments, a selective transport molecule disclosed herein has the formula (A-X-B)-D, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and D is a dendrimer. In some embodiments, D comprises a cargo moiety.

Certain Definitions

The following terms have the meanings ascribed to them unless specified otherwise.

The terms cell penetrating peptide (CPP), membrane translocating sequence (MTS) and protein transduction domain are used interchangeably. As used herein, the terms mean a peptide (polypeptide or protein) sequence that is able to translocate across the plasma membrane of a cell. In some embodiments, a CPP facilitates the translocation of an extracellular molecule across the plasma membrane of a cell. In some embodiments, the CPP translocates across the plasma membrane by direct penetration of the plasma membrane, endocytosis-mediated entry, or the formation of a transitory structure.

As used herein, the term "aptamer" refers to a DNA or RNA molecule that has been selected from random pools based on their ability to bind other molecules with high affinity specificity based on non-Watson and Crick interactions with the target molecule (see, e.g., Cox and Ellington, Bioorg. Med. Chem. 9:2525-2531 (2001); Lee et al., Nuc. Acids Res. 32:D95-D100 (2004)). In some embodiments, the aptamer binds nucleic acids, proteins, small organic compounds, vitamins, inorganic compounds, cells, and even entire organisms.

The terms "polypeptide," "peptide" and "protein" are used interchangeably herein to refer to a polymer of amino acid residues. The terms apply to naturally occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds. As used herein, the terms "peptide" refers to a polymer of amino acid residues typically ranging in length from 2 to about 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an α-ester, a β-ester, a thioamide, phosphonamide, carbamate, hydroxylate, and the like (see, e.g., Spatola, (1983) Chem. Biochem. Amino Acids and Proteins 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide-Symposium, ESCOM Science Publishers, The Netherlands, and the like)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be either D amino acids or L amino acids. In peptide sequences throughout the specification, lower case letters indicate the D isomer of the amino acid (conversely, upper case letters indicate the L isomer of the amino acid).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

As used herein, a "linker" is any molecule capable of binding (e.g., covalently) portion A and portion B of a selective transport molecule disclosed herein. Linkers include, but are not limited to, straight or branched chain carbon linkers, heterocyclic carbon linkers, peptide linkers, and polyether linkers. For example, poly(ethylene glycol) linkers are available from Quanta Biodesign, Powell, Ohio. These linkers optionally have amide linkages, sulfhydryl linkages, or heterofunctional linkages.

As used herein, the term "label" refers to any molecule that facilitates the visualization and/or detection of a selective transport molecule disclosed herein. In some embodiments, the label is a fluorescent moiety.

The term "carrier" means an inert molecule that increases (a) plasma half-life and (b) solubility. In some embodiments, a carrier increases plasma half-life and solubility by reducing glomerular filtration. In some embodiments, a carrier increases tumor uptake due to enhanced permeability and retention (EPR) of tumor vasculature.

The terms "individual," "patient," or "subject" are used interchangeably. As used herein, they mean any mammal (i.e. species of any orders, families, and genus within the taxonomic classification animalia: chordata: vertebrata: mammalia). In some embodiments, the mammal is a human. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The terms "administer," "administering", "administration," and the like, as used herein, refer to the methods that may be used to enable delivery of agents or compositions to the desired site of biological action. These methods include, but are not limited to parenteral injection (e.g., intravenous, subcutaneous, intraperitoneal, intramuscular, intravascular, intrathecal, intravitreal, infusion, or local). Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "surgery" as used herein, refers to any methods for that may be used to manipulate, change, or cause an effect by a physical intervention. These methods include, but are not limited to open surgery, endoscopic surgery, laparoscopic surgery, minimally invasive surgery, and robotic surgery.

The following symbols, where used, are used with the indicated meanings: Fl=fluorescein; aca=ahx=X=aminocaproic acid linker (—HN—$(CH_2)_5$—CO—); C=L-cysteine; E=L-glutamate; R=L-arginine; D=L-aspartate; K=L-lysine; A=L-alanine; r=D-arginine; c=D-cysteine; e=D-glutamate; P=L-proline; L=L-leucine; G=glycine; V=valine; I=isoleucine; M=methionine; F=phenylalanine; Y=tyrosine; W=tryptophan; H=histidine; Q=glutamine; N=asparagine; S=serine; and T=threonine.

Selective Transport Molecules

Regulation of transport into and out of a cell is important for its continued viability. For example, cell membranes contain ion channels, pumps, and exchangers capable of facilitating the transmembrane passage of many important substances. However, transmembrane transport is selective: in addition to facilitating the entry of desired substances into a cell, and facilitating the exit of others, a major role of a cell membrane is to prevent uncontrolled entry of substances into the cell interior. This barrier function of the cell membrane makes difficult the delivery of markers, drugs, nucleic acids, and other exogenous material into cells.

Multiple membrane translocation signals (MTS) have been identified. For example, the Tat protein of the human immunodeficiency virus 1 (HIV-1) is able to enter cells from the extracellular environment. A domain from Antennapedia homeobox protein is also able to enter cells.

Molecules comprising a MTS may also be used to carry other molecules into cells along with them. The most important MTS are rich in amino acids such as arginine with positively charged side chains. Molecules transported into cell by such cationic peptides may be termed "cargo" and may be reversibly or irreversibly linked to the cationic peptides.

The uptake facilitated by molecules comprising a MTS is currently without specificity, enhancing uptake into most or all cells. It is desirable to have the ability to target the delivery of cargo to a type of cell, or to a tissue, or to a location or region within the body of an animal. Accordingly, we have identified a need for a selective transport molecule with increased in vivo circulation.

In some embodiments, a selective transport molecule disclosed herein has the formula (A-X-B-C)-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and M is a macromolecular carrier.

In some embodiments, a selective transport molecule disclosed herein has the formula (A-X-B)-D, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and D is a dendrimer. In some embodiments, D comprises a cargo moiety.

In embodiments, a selective transport molecule disclosed herein is a linear molecule. In embodiments, a selective transport molecule disclosed herein is a cyclic molecule, as schematically illustrated in FIG. 1B. In embodiments, a selective transport molecule disclosed herein comprises a cyclic portion and a linear portion.

A selective transport molecule disclosed herein may be of any length. In some embodiments, a selective transport molecule disclosed herein is about 7 to about 40 amino acids in length, not including the length of a linker X and a cargo moiety C. In other embodiments, particularly where multiple non-acidic (in portion A) or non-basic (in portion B) amino acids are included in one or both of portions A and B, portions A and B of a selective transport molecule disclosed herein may together be about 50, or about 60, or about 70 amino acids in length. A cyclic portion of a selective transport molecule disclosed herein may include about 12 to about 60 amino acids, not including the length of a linker X and a cargo moiety C. For example, a linear selective transport molecule disclosed herein may have a basic portion B having between about 5 to about 20 basic amino acids (preferably between about 9 to about 16 basic amino acids) and an acidic portion A having between about 2 to about 20 acidic amino acids (e.g., between about 5 to about 20, preferably between about 5 to about 9 acidic amino acids). In some preferred embodiments, a selective transport molecule disclosed herein may have a basic portion B having between about 9 to about 16 basic amino acids and between about 5 to about 9 acidic amino acids. In some embodiments, A is 8 consecutive glutamates (i.e., EEEEEEEE, $E_9$, eeeeeeee, or e9), B is nine consecutive arginines (i.e., RRRRRRRRR, $R_9$, rrrrrrrrr, or r9), and X is PLGLAG (SEQ ID NO: 1).

In some embodiments, the selective transport molecule has a formula given below. It should be noted that in some instances the peptide sequence is given by the amino acid symbol and a number indicating the number of amino acids (for example, $R_9$ translates to RRRRRRRRR or nine consecutive L-arginines; and r9 translates to nine consecutive D-arginines or rrrrrrrrr).

(SEQ ID NO: 7)

EDDDDKA-aca-$R_9$-aca-C(Fl)-$CONH_2$ (SEQ ID NO: 8)

Fl-aca-CRRRRRRRRR-aca-EEEEEEEEC-$CONH_2$

-continued

F1-aca-CEEEE-aca-RRRRRRRRRC-CONH$_2$ (SEQ ID NO: 9)
H$_2$N-EEEEEDDDDKA-aca-RRRRRRRRR-aca-C(F1)-CONH$_2$ (SEQ ID NO: 10)
H$_2$N-EDDDDKA-aca-RRRRRRRRR-aca-C(F1)-CONH$_2$ (SEQ ID NO: 11)
H$_2$N-EEEEDDDDKARRRRRRRRR-aca-C(F1)-CONH$_2$ (SEQ ID NO: 12)
H$_2$N-EEDDDDKA-aca-rrrrrrrn-aca-C(F1)-CONH$_2$ (SEQ ID NO: 13)
H$_2$N-DDDDDDKARRRRRRRRR-aca-C(F1)-CONH$_2$ (SEQ ID NO: 14)
H$_2$N-EEDDDDKAR-aca-RR-aca-RR-aca-RR-aca-C(F1)-CONH$_2$ H$_2$N-eeeeee-aca-PLGLAG-rrrrrrrr-aca-c(F1)-CONH$_2$ (SEQ ID NO: 15)
EDA-aca-R$_5$-aca-C(F1)-CONH$_2$ (SEQ ID NO: 16)
EDDDDKA-aca-R$_6$-aca-C(DOX)-CONH$_2$ (SEQ ID NO: 17)
EEEDDDEEEDA-aca-R$_9$-aca-Y($^{125}$I)-CONH$_2$ ededdAAeeeDDDDKA-aca-R$_{11}$-aca-C(F1)-CONH$_2$ eddedededDDDDKA-aca-R$_6$-AGA-R$_6$-aca-C(DOX)-CONH$_2$ Ggedgddeeeeeeddeed-aca-PLGLAG-aca-R$_8$-AAA-R$_{12}$-aca-C(F1)-CONH$_2$ eeddeeddKA-aca-R$_7$-aca-C(F1)-CONH$_2$ eDDDDKA-aca-RGRGRRR-aca-C(F1)-CONH$_2$ eddddeeeeee-aca-PLGLAGKA-aca-R$_{10}$-aca-C(F1)-CONH$_2$ eeeeeeeeeeeeeee-aca-DDDDKA-aca-R$_{20}$-aca-C(Fl)-CONH$_2$ eeeeeeeeeddddd-aca-DDDDKA-aca-R$_{17}$-aca-Y($^{125}$l)-CONH$_2$ ddddddddddddddd-aca-PLGLAG-aca-R$_{14}$-aca-C(DOX)-CONH$_2$ NH2-eeeeee-ahx-PLG LAG-rrrrrrrrr-ahx-c(F1)-CONH$_2$, where "ahx" indicates aminohexanoic acid (SEQ ID NO: 18)
EEEEEDDDDKAXRRRRRRRRRXC(F1)

(SEQ ID NO: 19)
EEEEEDDDDKARRRRRRRRRXC(F1)

(SEQ ID NO: 20)
EDDDDKAXRRRRRRRRRXC(F1)

(SEQ ID NO: 21)
EEDDDDKARXRRXRRXRRXRRXC(F1)

(SEQ ID NO: 22)
DDDDDDKARRRRRRRRRXC(F1)

EEDDDDKAXrrrrrrrrrXC(F1)

-continued eeeeeeXPLGLAGrrrrrrrrrXc(F1)

UeeeeeeeeXPLGLAGrrrrrrrrrXk(F1)

eeeeeeXPLGLAGrrrrrrrrrXc(Cy5)

UeeeeeeeXPLGLAGrrrrrrrrrXc(Cy5)

UeeeeeeeeXPLGLAGrrrrrrrrrXk(Cy5.5)

11-kDa PEG]XeeeeeeeeeXPLGLAGrrrrrrrrrXk(Cy5)

[11-kDa PEG]XeeeeeeeeeXLALGPGrrrrrrrrrXk(Cy5)

F1-XrrrrrrrrrXPLGLAGeeeeeeee-βAla

F1-XrrrrrrrrrXSGRSAeeeeeeee-βAla eeeeeeXSGRSAXrrrrrrrrrXc(Cy5)

F1-rrrrrrrrrc-SS-ceeeeee succinyl-e$_8$-XPLGLAG-r$_9$-Xk, where X denotes 6-aminohexanoyl

[11 kDa PEG]-X-e$_9$-XPLGLAG-r$_9$

[11 kDa PEG]-X-e$_9$-XPLGLAG-r$_9$-Xk(Cy5)

H$_2$N-e$_6$-XPLGLAG-r$_9$-Xc(Cy5)-CONH$_2$, where X = aminohexanoic acid

H$_2$N-eeeeee-(ahx)-PLG LAG-rrrrrrrrr-(ahx)-c(Fluor)-CONH$_2$

XeeeeeeeeeXPLGLAGrrrrrrrrrXk eeeeeeeeeXLALGPG-rrrrrrrrrXk(Cy5)

mPEG(11kd)-S-CH$_2$-CONH-ahx-e$_9$-ahx-PLGLAG-r$_9$-ahx-k-CONH$_2$ mPEG-S-CH$_2$CONH-e$_9$-ahx-PLGLAG-r$_9$-K[DOTA(Gd)]-CONH$_2$ (11 KDa-mPEG)-e$_9$-XPLGLAG-r$_9$-[DPK-$^{99m}$Tc(CO)$_3$]

70 KDa-dextran)-e$_9$-XPLGLAG-r$_9$-[DPK-$^{99m}$Tc(CO)$_3$]

(murine serum albumin)-e$_9$-XPLGLAG-r$_9$-[DPK-$^{99m}$Tc(CO)$_3$], (PAMAM generation 5 dendrimer)-e$_9$-XPLGLAX-r$_9$-[DPK-$^{99m}$Tc(CO)$_3$]

(70 KDa dextran)-e$_9$-XPLGLAX-r$_9$-(DOTA-$^{111}$In)

(11-KDa-mPEG)-e$_9$-XPLGLAG-r$_9$-K(DOTA-Gd)

Suc$_9$-(70 KDa dextran)-e$_9$-XPLGLAG-r$_9$-K(DOTA-Gd)

Suc$_9$-(70 KDa dextran)-e$_9$-XPLGLAX-r$_9$-K(DOTA-Gd)

Suc$_9$-(70 KDa dextran)-e$_9$-XPLGLAG-r$_9$-K(DOTA-Gd)

cyclic[succinoyl-PLGLAG-c(11 KDa-mPEG)-e$_9$-XPLGLAG-r$_9$-K]-k(Cy5)

Cy5-X-e$_6$-XPLGLAG-r$_9$-Xk(Cy5)

-continued

Cy7-X-e₆-XPLGLAG-r₉-Xk(Cy5)

11 KDa mPEG-e₉-PLGLAG-r₉

Ac-r₉-k-NH2 mPEG(11kd)-e₉-XPLGLAG-r₉-Xk-NH₂ e₉-XPLGLAG-r₉-Xk-NH₂

TABLE 1

| Cap | Macromolecule | Polyanion | P4 | P3 | P2 | P1 | P1' | P2' | P3'...Pn' | Polycation | Cargo | C-term |
|---|---|---|---|---|---|---|---|---|---|---|---|---|
| Suc9 | Dextran (70 KDa) | e9 | X | P | L | G | L | A | G | r9 | K[DOTA(Gd)] | NH₂ |
| Suc | — | e9 | X | P | L | G | C(Me) | A | X | r9 | DPK | NH₂ |
| Suc | — | e9 | X | P | ThienylAla | G | C(Me) | A | X | r9 | DPK | NH₂ |
| Suc | — | e9 | X | P | F(4---Cl) | G | C(Me) | A | X | r9 | DPK | NH₂ |
| Suc | — | e8 | X | P | L | G | L | A | G | r9 | c[Cy5] | NH₂ |
| Suc | — | e8 | X | P | F(4---Cl) | G | C(Me) | M | X | r9 | c[Cy5] | NH₂ |
| Suc | — | e8 | X | P | F(4---Cl) | G | C(Me) | Y | X | r9 | c[Cy5] | NH₂ |
| Suc | — | e8 | X | P | F(4---Cl) | G | C(Me) | R | X | r9 | c[Cy5] | NH₂ |
| Suc | — | e8 | X | P | F(4---Cl) | G | C(Me) | PhGly | X | r9 | c[Cy5] | NH₂ |
| Suc | — | e8 | X | P | F(4---Cl) | G | C(Me) | C(Me) | X | r9 | c[Cy5] | NH₂ |
| — | Albumin | e9 | X | P | L | G | L | A | X | r9 | DPK | NH₂ |
| Suc | — | e8 | X | P | C(Me) | G | C(Me) | A | X | r9 | c[Cy5] | NH₂ |
| Suc | — | e8 | X | P | ThienylAla | G | C(Me) | A | X | r9 | c[Cy5] | NH₂ |
| Suc | — | e8 | X | P | F(4---Cl) | G | C(Me) | A | X | r9 | c[Cy5] | NH₂ |
| Suc | — | e8 | X | P | K(Dnp) | G | C(Me) | A | X | r9 | c[Cy5] | NH₂ |
| — | Albumin | e9 | X | P | L | G | L | A | X | r9 | DPK | NH₂ |
| Suc | — | e8 | X | P | L | G | C(Me) | M | X | r9 | c[Cy5] | NH₂ |
| Suc | — | e8 | X | P | L | G | C(Me) | Y | X | r9 | c[Cy5] | NH₂ |
| Suc127 | PAMAM-Gen5 | e9 | X | P | L | G | L | A | X | r9 | DPK | NH₂ |
| Suc | — | e8 | X | P | L | G | C(Me) | A | X | r9 | c[Cy5] | NH₂ |
| Suc9 | Dextran (70 KDa) | e9 | X | P | L | G | L | A | G | r9 | K[DOTA(Gd)] | NH₂ |
| Suc127 | PAMAM-Gen5 | e9 | X | P | L | G | L | A | X | r9 | k[Cy5] | NH₂ |
| — | — | — | — | — | — | — | — | — | — | r9 | Xc[Cy5] | NH₂ |
| Ac127 | PAMAM-Gen5 | e9 | X | P | L | G | L | A | X | r9 | k[Cy5] | NH₂ |
| Suc | — | e8 | X | P | L | G | L | F(4---NO2) | A | Xr9 | k[Cy5] | NH₂ |
| Suc127 | PAMAM-Gen5 | e9 | X | P | L | G | L | A | X | r9 | k[Cy5] | NH₂ |
| Suc63 | PAMAM-Gen4 | e9 | X | P | L | G | L | A | X | r9 | k[Cy5] | NH₂ |
| — | Albumin | e9 | X | P | L | G | L | A | G | r9 | DPK | NH₂ |
| Suc136 | Dextran (86 KDa) | e9 | X | P | L | G | L | A | X | r9 | k[Cy5] | NH₂ |
| Suc | — | e8 | X | P | L | G | L | A | X | r9 | k[Cy5] | NH₂ |
| Suc9 | Dextran (70 KDa) | e9 | X | P | L | G | L | A | X | r9 | K[DOTA(Gd)] | NH₂ |
| Suc9 | Dextran (70 KDa) | e9 | X | P | L | G | L | A | X | r9 | K[DOTA(Gd)] | NH₂ |
| Suc9 | Dextran (70 KDa) | e9 | X | P | L | G | L | A | G | r9 | k[Cy5] | NH₂ |
| Suc9 | Dextran (70 KDa) | e9 | X | P | L | G | L | A | G | r9 | DPK | NH₂ |
| Suc | — | e8 | X | p | l | g | l | a | g | r9 | k[Cy5] | NH₂ |
| — | Albumin | e9 | X | p | l | g | l | a | g | r9 | k[Cy5] | NH₂ |
| Suc9 | Dextran | e9 | X | p | l | g | l | a | g | r9 | k[Cy5] | NH₂ |
| Suc97 | Dextran (500 KDa) | e9 | X | P | L | G | L | A | G | r9 | k[Cy5] | NH₂ |
| — | Albumin | e9 | X | P | L | G | L | A | G | r9 | k[Cy5] | NH₂ |
| Suc9 | Dextran (70 KDa) | e9 | X | P | L | G | L | A | G | r9 | k[Cy5] | NH₂ |
| — | Albumin | e9 | X | P | L | G | L | A | G | r9 | k[Cy5] | NH₂ |
| Suc | — | e8 | X | P | L | G | L | A | X | r9 | k[Cy5] | NH₂ |
| Suc9 | Dextran (70 KDa) | e9 | X | P | L | G | L | A | G | r9 | k[Cy5] | NH₂ |
| — | Albumin | e9 | X | P | L | G | L | A | G | r9 | k[Cy5] | NH₂ |
| — | Albumin | e9 | X | P | L | G | L | A | G | r9 | k[Cy5] | NH₂ |
| Suc9 | Dextran (70 KDa) | e9 | X | P | L | G | L | A | G | r9 | k[Cy5] | NH₂ |
| Suc | nonconj. Albumin | e8 | X | P | L | G | L | A | G | r9X | k[Cy5] | NH₂ |
| Suc | — | e8 | X | P | L | G | L | A | G | r9X | k[Cy5] | NH₂ |
| — | Albumin | e9 | X | P | L | G | L | A | G | r9 | k[Cy5] | NH₂ |
| — | mPEG (5 KDa) | e9 | x | p | l | g | l | a | g | r9X | k[Cy5] | NH₂ |
| — | mPEG (11 KDa) | e9 | X | P | L | G | L | A | G | r9 | K[DOTA(Gd)] | NH₂ |
| — | mPEG (11 KDa) | e10 | X | P | L | G | F(4-NO₂) | A | Q | Xr9 | k[Cy5] | NH₂ |

TABLE 1-continued

| Cap | Macromolecule | Polyanion | P4 | P3 | P2 | P1 | P1' | P2' | P3'...Pn' | Polycation | Cargo | C-term |
|---|---|---|---|---|---|---|---|---|---|---|---|---|
| — | mPEG (11 KDa) | e10 | X | P | L | G | C(Me) | W | A | Qr9 | k[Cy5] | $NH_2$ |
| — | mPEG (11 KDa) | e9 | X | P | L | G | C(Me) | W | A | Qr9 | k[Cy5] | $NH_2$ |

Peptide Synthesis

A selective transport molecule disclosed herein is synthesized by any suitable method, such as, for example, solid phase synthesis including solid phase peptide synthesis. An example of peptide synthesis using Fmoc is given as Example 1 below. For example, conventional solid phase methods for synthesizing peptides may start with N-alpha-protected amino acid anhydrides that are prepared in crystallized form or prepared freshly in solution, and are used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1 to 2 reaction cycles are used for the first twelve residue additions, and 2 to 3 reaction cycles for the remaining residues.

After completing the growing peptide chains, the protected peptide resin is treated with a strong acid such as liquid hydrofluoric acid or trifluoroacetic acid to deblock and release the peptides from the support. For preparing an amidated peptide, the resin support used in the synthesis is selected to supply a C-terminal amide, after peptide cleavage from the resin. After removal of the strong acid, the peptide may be extracted into 1M acetic acid solution and lyophilized. The peptide may be isolated by an initial separation by gel filtration, to remove peptide dimers and higher molecular weight polymers, and also to remove undesired salts The partially purified peptide may be further purified by preparative HPLC chromatography, and the purity and identity of the peptide confirmed by amino acid composition analysis, mass spectrometry and by analytical HPLC (e.g., in two different solvent systems).

Polynucleotide Synthesis

Disclosed herein, in certain embodiments is a polynucleotide encoding a selective transport molecule described herein. The term "polynucleotide" refers to a polymeric form of nucleotides of at least 10 bases in length. Nucleotides include ribonucleotides, deoxynucleotides, or modified forms of either type of nucleotide. The term includes single and double stranded forms of DNA. The term therefore includes, for example, a recombinant DNA which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

These polynucleotides include DNA, cDNA, and RNA sequences which encode a selective transport molecule described herein, or portions thereof. In some embodiments, polynucleotides include promoter and other sequences, and may be incorporated into a vector for transfection (which may be stable or transient) in a host cell.

The construction of expression vectors and the expression of genes in transfected cells involves the use of molecular cloning techniques that are well known in the art. See, for example, Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., most recent Supplement). Nucleic acids used to transfect cells with sequences coding for expression of the polypeptide of interest generally will be in the form of an expression vector including expression control sequences operatively linked to a nucleotide sequence coding for expression of the polypeptide. As used herein, "operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. The term "control sequences" is intended to include, at a minimum, components that are able to influence expression, and also include additional components whose presence is advantageous, for example, leader sequences and fusion partner sequences. As used herein, the term "nucleotide sequence coding for expression of" a polypeptide refers to a sequence that, upon transcription and translation of mRNA, produces the polypeptide. This includes sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Any suitable method is used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989). Transformation of a host cell with recombinant DNA may be carried out by conventional techniques as are well known to those skilled in the art.

Where the host is prokaryotic, such as *E. coli*, competent cells (i.e., cell which are capable of DNA uptake) are prepared from cells harvested after exponential growth phase and subsequently treated with $CaCl_2$, $MgCl_2$ or RbCl. In certain instances, transformation is performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. In certain instances, eukaryotic cells are co-transfected with DNA sequences encoding a molecule disclosed herein, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Techniques for the isolation and purification of polypeptides of the invention expressed in prokaryotes or eukaryotes may be by any conventional means such as, for example, preparative chromatographic separations and immunological separations such as those involving the use of monoclonal or polyclonal antibodies or antigen.

Portion A

Disclosed herein, in certain embodiments, is a selective transport molecule with increased in vivo circulation.

In some embodiments, a selective transport molecule disclosed herein has the formula (A-X-B-C)-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and M is a macromolecular carrier.

In some embodiments, a selective transport molecule disclosed herein has the formula (A-X-B)-D, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and D is a dendrimer. In some embodiments, D comprises a cargo moiety.

In some embodiments, a selective transport molecule disclosed herein has the formula $(A-X-B)_n$-D, wherein D comprises at least two cargo moieties; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and n is an integer between 1 and 20.

In some embodiments of molecules having features of the invention, peptide portion A includes between about 2 to about 20, or between about 5 to about 20 acidic amino acids, and may be series of acidic amino acids (e.g., glutamates and aspartates or other acidic amino acids). In some embodiments, A has a sequence comprising 5 to 9 consecutive glutamates.

In some embodiments, portion A comprises 8 consecutive glutamates (i.e., EEEEEEEE or eeeeeeee).

An acidic portion A may include amino acids that are not acidic. Acidic portion A may comprise other moieties, such as negatively charged moieties. In embodiments of a selective transport molecule disclosed herein, an acidic portion A may be a negatively charged portion, preferably having about 2 to about 20 negative charges at physiological pH that does not include an amino acid. In preferred embodiments, the amount of negative charge in portion A is approximately the same as the amount of positive charge in portion B.

Portion A is either L-amino acids or D-amino acids. In embodiments of the invention, D-amino acids are preferred in order to minimize immunogenicity and nonspecific cleavage by background peptidases or proteases. Cellular uptake of oligo-D-arginine sequences is known to be as good as or better than that of oligo-L-arginines.

It will be understood that portion A may include non-standard amino acids, such as, for example, hydroxylysine, desmosine, isodesmosine, or other non-standard amino acids. Portion A may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. Portion A may also include peptide mimetic moieties, including portions linked by non-peptide bonds and amino acids linked by or to non-amino acid portions.

The generic structures A X-B and A X B-C is effective where A is at the amino terminus or where A is at the carboxy terminus, i.e., either orientation of the peptide bonds is permissible.

Portion B (Membrane-Translocating Sequence)

Disclosed herein, in certain embodiments, is a selective transport molecule with increased in vivo circulation.

In some embodiments, a selective transport molecule disclosed herein has the formula (A-X-B-C)-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and M is a macromolecular carrier.

In some embodiments, a selective transport molecule disclosed herein has the formula (A-X-B)-D, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and D is a dendrimer. In some embodiments, D comprises a cargo moiety.

In some embodiments, a selective transport molecule disclosed herein has the formula $(A-X-B)_n$-D, wherein D comprises at least two cargo moieties; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and n is an integer between 1 and 20. In some embodiments, B has a sequence comprising 5 to 12 consecutive arginines. In some embodiments, B has a sequence comprising 9 consecutive arginines.

In some embodiments of molecules having features of the invention, peptide portion B includes between about 5 to about 20, or between about 9 to about 16 basic amino acids, and may be a series of basic amino acids (e.g., arginines, histidines, lysines, or other basic amino acids).

In some embodiments, portion B comprises 9 consecutive arginines (i.e., RRRRRRRRR or rrrrrrrrr).

A basic portion B may include amino acids that are not basic. Basic portion B may comprise other moieties, such as positively charged moieties. In embodiments, a basic portion B may be a positively charged portion, preferably having between about 5 and about 20 positive charges at physiological pH, that does not include an amino acid. In preferred embodiments, the amount of negative charge in portion A is approximately the same as the amount of positive charge in portion B.

Portion B is either L-amino acids or D-amino acids. In embodiments of the invention, D-amino acids are preferred in order to minimize immunogenicity and nonspecific cleavage by background peptidases or proteases. Cellular uptake of oligo-D-arginine sequences is known to be as good as or better than that of oligo-L-arginines.

It will be understood that portion B may include non-standard amino acids, such as, for example, hydroxylysine, desmosine, isodesmosine, or other non-standard amino acids. Portion B may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. Portion B may also include peptide mimetic moieties, including portions linked by non-peptide bonds and amino acids linked by or to non-amino acid portions.

In embodiments where X is a peptide cleavable by a protease, it may be preferable to join the C-terminus of X to the N-terminus of B, so that the new amino terminus created by cleavage of X contributes an additional positive charge that adds to the positive charges already present in B.

Portion X (Linkers)

Disclosed herein, in certain embodiments, is a selective transport molecule with increased in vivo circulation.

In some embodiments, a selective transport molecule disclosed herein has the formula (A-X-B-C)-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and M is a macromolecular carrier.

In some embodiments, a selective transport molecule disclosed herein has the formula (A-X-B)-D, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and D is a dendrimer. In some embodiments, D comprises a cargo moiety.

Cleavage Conditions

In some embodiments, X is a cleavable linker.

In some embodiments, a linker X is designed for cleavage in the presence of particular conditions or in a particular environment. In preferred embodiments, a linker X is cleavable under physiological conditions. Cleavage of such a linker X may, for example, be enhanced or may be affected by particular pathological signals or a particular environment related to cells in which cargo delivery is desired. The design of a linker X for cleavage by specific conditions, such as by a specific enzyme, allows the targeting of cellular uptake to a specific location where such conditions obtain. Thus, one important way that selective transport molecules provide specific targeting of cellular uptake to desired cells, tissues, or regions is by the design of the linker portion X to be cleaved by conditions near such targeted cells, tissues, or regions. After cleavage of a linker X, the portions B C of the molecule are then a simple conjugate of B and C, in some instances retaining a relatively small, inert stub remaining from a residual portion of linker X.

In some embodiments, X is a pH-sensitive linker. In some embodiments, X is cleaved under basic pH conditions. In some embodiments, X is cleaved under acidic pH conditions. In some embodiments, X is cleaved by a protease, a matrix metalloproteinase, or a combination thereof. In some embodiments, X is cleaved by a reducing agent.

One important class of signals is the hydrolytic activity of matrix metalloproteinases (MMPs), which are very important in the invasive migration of metastatic tumor cells. In certain instances, MMPs are found near sites of inflammation. In certain instances, MMPs are found near sites of stroke (i.e., a disorder characterized by brain damage following a decrease in blood flow). In some embodiments, X is cleaved by an MMP. Thus, uptake of molecules having features of the invention are able to direct cellular uptake of cargo C to specific cells, tissues, or regions having active MMPs in the extracellular environment.

In some embodiments, a linker X that includes the amino-acid sequence PLGLAG (SEQ ID NO: 1) is cleaved by the metalloproteinase enzyme MMP-2 (a major MMP in cancer and inflammation). Cleavage of such a linker X occurs between the central G and L residues, causing cell uptake to increase by 10 to 20-fold (see Example 4). In some embodiments, linkers X designed to be cleaved by membrane-anchored MMPs are particularly preferred because their activity remains localized to the outer surface of the expressing cell. In alternative embodiments, linkers X designed to be cleaved by a soluble secreted MMP are preferred where diffusion of cargo C away from the exact location of cleavage may be desired, thereby increasing the spatial distribution of the cargo. Other linkers X cleavable by other MMPs are discussed in Example 9.

In some embodiments, a linker designed so that it is cleaved by proteolytic enzymes or reducing environment, as may be found near cancerous cells. Such an environment, or such enzymes, are typically not found near normal cells.

Hypoxia is an important pathological signal. For example, hypoxia is thought to cause cancer cells to become more resistant to radiation and chemotherapy, and also to initiate angiogenesis. In some embodiments, a linker X suitable for cleavage in or near tissues suffering from hypoxia enables targeting of portion B and C to cancer cells and cancerous tissues, infarct regions, and other hypoxic regions. In some embodiments, a linker X that includes a disulfide bond is preferentially cleaved in hypoxic regions and so targets cargo delivery to cells in such a region. In a hypoxic environment in the presence of, for example, leaky or necrotic cells, free thiols and other reducing agents become available extracellularly, while the 02 that normally keeps the extracellular environment oxidizing is by definition depleted. In some embodiments, this shift in the redox balance promotes reduction and cleavage of a disulfide bond within a linker X. In addition to disulfide linkages which take advantage of thiol-disulfide equilibria, linkages including quinones that fall apart when reduced to hydroquinones are used in a linker X designed to be cleaved in a hypoxic environment.

Necrosis often leads to the release of enzymes or other cell contents that may be used to trigger cleavage of a linker X. In some embodiments, a linker X designed for cleavage in regions of necrosis in the absence of hypoxia, comprises a calpain (or other proteases that are released from necrotic cells). Such cleavage of linkers X by calpains would release the connected portions B-C from portion A, allowing cargo to be taken up by diseased cells and by neighboring cells that had not yet become fully leaky.

Acidosis is also commonly observed in sites of damaged or hypoxic tissue, due to the Warburg shift from oxidative phosphorylation to anaerobic glycolysis and lactic acid production. Such local acidity could be sensed either by making an acid-labile linker X (e.g., by including in X an acetal or vinyl ether linkage). Alternatively, or in addition, acidosis may be used as a trigger of cargo uptake by replacing some of the arginines within B by histidines, which only become cationic below pH 7.

Linkers

In some embodiments, a linker consisting of one or more amino acids is used to join peptide sequence A (i.e., the sequence designed to prevent uptake into cells) and peptide sequence B (i.e., the MTS). Generally the peptide linker will have no specific biological activity other than to join the molecules or to preserve some minimum distance or other spatial relationship between them. However, the constituent amino acids of the linker may be selected to influence some property of the molecule such as the folding, net charge, or hydrophobicity.

In some embodiments, X is a cleavable linker.

In some embodiments, the linker is flexible. In some embodiments, the linker is rigid.

In some embodiments, the linker comprises a linear structure. In some embodiments, the linker comprises a non-linear structure. In some embodiments, the linker comprises a branched structure. In some embodiments, the linker comprises a cyclic structure.

In some embodiments, X is about 5 to about 30 atoms in length. In some embodiments, X is about 6 atoms in length. In some embodiments, X is about 8 atoms in length. In some embodiments, X is about 10 atoms in length. In some embodiments, X is about 12 atoms in length. In some embodiments, X is about 14 atoms in length. In some embodiments, X is about 16 atoms in length. In some embodiments, X is about 18 atoms in length. In some embodiments, X is about 20 atoms in length. In some embodiments, X is about 25 atoms in length. In some embodiments, X is about 30 atoms in length.

In some embodiments, the linker binds peptide portion A (i.e., the peptide sequence which prevents cellular uptake) to peptide portion B (i.e., the MTS sequence) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, X comprises a peptide linkage. The peptide linkage comprises L-amino acids and/or D-amino acids. In embodiments of the invention, D-amino acids are preferred in order to minimize immunogenicity and nonspecific cleavage by background peptidases or proteases. Cellular uptake of oligo-D-arginine sequences is known to be as good as or better than that of oligo-L-arginines.

It will be understood that a linker disclosed herein may include non-standard amino acids, such as, for example, hydroxylysine, desmosine, isodesmosine, or other non-standard amino acids. A linker disclosed herein may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. A linker disclosed herein may also include peptide mimetic moieties, including portions linked by non-peptide bonds and amino acids linked by or to non-amino acid portions.

In some embodiments, X comprises a peptide selected from: PLGLAG (SEQ ID NO: 1), PLGLAX (SEQ ID NO: 2), PLG-C(me)-AG (SEQ ID NO: 3), ESPAYYTA (SEQ ID NO: 4), and RLQLKL (SEQ ID NO: 5), AND RLQLK(AC) (SEQ ID NO: 6).

In some embodiments, X comprises a peptide selected from: PR(S/T)(L/I)(S/T) (SEQ ID NO: 23), where the letters in parentheses indicate that either one of the indicated amino acids may be at that position in the sequence); GGAANLVRGG (SEQ ID NO: 24); SGRIGFLRTA (SEQ ID NO: 25); SGRSA (SEQ ID NO: 26); GFLG (SEQ ID NO: 27); ALAL (SEQ ID NO: 28); FK; PIC(Et)F-F (SEQ ID NO: 29, where C(Et) indicates S-ethylcysteine (a cysteine with an ethyl group attached to the thiol) and the "-" indicates the typical cleavage site in this and subsequent sequences); GGPRGLPG (SEQ ID NO: 30); HSSKLQ (SEQ ID NO: 31); LVLA-SSSFGY (SEQ ID NO: 32); GVSQNY-PIVG (SEQ ID NO: 33); GVVQA-SCRLA (SEQ ID NO: 34); f(Pip)R-S (where "f" indicates D-phenylalanine and "Pip" indicates piperidine-2-carboxylic acid (pipecolinic acid, a proline analog having a six-membered ring); DEVD (SEQ ID NO: 35); GWEHD-G (SEQ ID NO: 36); or a combination thereof.

In some embodiments, X is cleaved under hypoxic conditions. In some embodiments, X comprises a disulfide linkage. In some embodiments, X comprises a quinine.

In some embodiments, X is cleaved under necrotic conditions. In some embodiments, X comprises a molecule cleavable by a calpain.

In some embodiments, X comprises 6-aminohexanoyl, 5-(amino)-3-oxapentanoyl, or a combination thereof. In some embodiments, X comprises a disulfide linkage.

In some embodiments, the linker is an alkyl. In some embodiments, the linker is heteroalkyl.

In some embodiments, the linker is an alkylene. In some embodiments, the linker is an alkenylene. In some embodiments, the linker is an alkynylene. In some embodiments, the linker is a heteroalkylene.

An "alkyl" group refers to an aliphatic hydrocarbon group. The alkyl moiety may be a saturated alkyl or an unsaturated alkyl. Depending on the structure, an alkyl group can be a monoradical or a diradical (i.e., an alkylene group).

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 6 carbon atoms. The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from: methyl, ethyl, propyl, isopropyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, and the like.

In some embodiments, the linker comprises a ring structure (e.g., an aryl). As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyl groups include groups having from 3 to 10 ring atoms. Cycloalkyls include, but are not limited to, cyclopropyl, cyclobutyl, cyclopentyl, cyclohexyl, cycloheptyl, and cyclooctyl.

In some embodiments, the ring is a cycloalkane. In some embodiments, the ring is a cycloalkene.

In some embodiments, the ring is an aromatic ring. The term "aromatic" refers to a planar ring having a delocalized π electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

In some embodiments, the ring is a heterocycle. The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzofused ring systems and ring systems substituted with one or two oxo (=O) moieties such as pyrrolidin-2-one. Depending on the structure, a heterocycle group can be a monoradical or a diradical (i.e., a heterocyclene group).

In some embodiments, the ring is fused. The term "fused" refers to structures in which two or more rings share one or more bonds. In some embodiments, the ring is a dimer. In some embodiments, the ring is a trimer. In some embodiments, the ring is a substituted.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e., a heteroatom). Heterocycle includes heteroaryl and heterocycloalkyl. Carbocycles and heterocycles can be optionally substituted.

In some embodiments, the linker is substituted. The term "optionally substituted" or "substituted" means that the referenced group may be substituted with one or more additional group(s) individually and independently selected from $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_2$-$C_8$acyloxy, nitro, $C_1$-$C_6$haloalkyl, $C_1$-$C_6$fluoroalkyl, and amino, including $C_1$-$C_6$alkylamino, and the protected derivatives thereof. By way of example, an optional substituents may be LsRs, wherein each Ls is independently selected from a bond, —O—, —C(=O)—, —S—, =S(=O)—, —S(=O)$_2$—, —NH—, —NHC(=O)—, —C(=O)NH—, S(=O)$_2$NH—, —NHS(=O)$_2$—, —OC(=O)NH—, —NHC(=O)O—, —($C_1$-$C_6$alkyl)-, or —($C_2$-$C_6$alkenyl)-; and each Rs is independently selected from H, ($C_1$-$C_4$alkyl), ($C_3$-$C_8$cycloalkyl), heteroaryl, aryl, and $C_1$-$C_6$heteroalkyl. Optionally substituted non-aromatic groups may be substituted with one or more oxo (=O). The protecting groups that may form the protective derivatives of the above substituents are known to those of skill in the art.

In some embodiments, a selective transport molecule disclosed herein comprises a single of linker. Use of a single mechanism to mediate uptake of both imaging and therapeutic cargoes is particularly valuable, because imaging with noninjurious tracer quantities can be used to test whether a subsequent therapeutic dose is likely to concentrate correctly in the target tissue.

In some embodiments, a selective transport molecule disclosed herein comprises a plurality of linkers. Where a selective transport molecule disclosed herein includes multiple linkages X, separation of portion A from the other portions of the molecule requires cleavage of all linkages X. Cleavage of multiple linkers X may be simultaneous or sequential. Multiple linkages X may include linkages X having different specificities, so that separation of portion A from the other portions of the molecule requires that more than one condition or environment ("extracellular signals") be encountered by the molecule. Cleavage of multiple linkers X thus serves as a detector of combinations of such extracellular signals. For example, a selective transport molecule may include two linker portions Xa and Xb connecting basic portion B with acidic portion A. Both linkers Xa and Xb must be cleaved before acidic portion A is separated from basic portion B allowing entry of portion B and cargo moiety C (if any) to enter a cell. It will be understood that a linker region may link to either a basic portion B or a cargo moiety C independently of another linker that may be present, and that, where desired, more than two linker regions X may be included.

Combinations of two or more linkers X may be used to further modulate the targeting and delivery of molecules to desired cells, tissue or regions. Combinations of extracellular signals are used to widen or narrow the specificity of the cleavage of linkers X if desired. Where multiple linkers X are linked in parallel, the specificity of cleavage is narrowed, since each linker X must be cleaved before portion A may separate from the remainder of the molecule. Where multiple linkers X are linked in series, the specificity of cleavage is broadened, since cleavage on any one linker X allows separation of portion A from the remainder of the molecule. For example, in order to detect either a protease OR hypoxia (i.e., to cleave X in the presence of either protease or hypoxia), a linker X is designed to place the protease-sensitive and reduction-sensitive sites in tandem, so that cleavage of either would suffice to allow separation of the acidic portion A. Alternatively, in order to detect the presence of both a protease AND hypoxia (i.e., to cleave X in the presence of both protease and hypoxia but not in the presence of only one alone), a linker X is designed to place the protease sensitive site between at least one pair of cysteines that are disulfide-bonded to each other. In that case, both protease cleavage and disulfide reduction are required in order to allow separation of portion A.

Extracellular Cleavage

In healthy cells, the intact compound of structure A X B or A X B-C would not be able to enter the cell because of the presence of portion A. Thus, a strictly intracellular process for cleaving X would be ineffective to cleave X in healthy cells since portion A, preventing uptake into cells, would not be effectively cleaved by intracellular enzymes in healthy cells since it would not be taken up and would not gain access to such intracellular enzymes. However, where a cell is injured or diseased (e.g., cancerous cells, hypoxic cells, ischemic cells, apoptotic cells, necrotic cells) such intracellular enzymes leak out of the cell and cleavage of A would occur, allowing entry of portion B or B C into the cell, effecting targeted delivery of portion B or of cargo moiety C to neighboring cells. In some embodiments, X is cleaved in the extracellular space.

The fact that capillaries are often leaky around tumors and other trauma sites should enhance the ability of high molecular weight molecules (e.g., molecular weight of about 40 kDa or more) to reach the interstitial compartment. Since the cleavage of a linker X is typically extracellular, some bystander labeling is expected, i.e., cells that do not express the relevant protease but that are immediately adjacent to expressing cells are likely to pick up some of the cargo. For tumors, such bystander targeting is considered beneficial because of the heterogeneity of cell phenotypes and the wish to eliminate as high a percentage of suspicious cells.

Macromolecular Carrier

Disclosed herein, in certain embodiments, is a selective transport molecule with increased in vivo circulation. In some embodiments, a selective transport molecule disclosed herein has the formula (A-X-B-C)-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and M is a macromolecular carrier.

The term “carrier” means an inert molecule that increases (a) plasma half-life and (b) solubility.

In some embodiments, a carrier decreases uptake of a selective transport molecule into cartilage. In some embodiments, a carrier decreases uptake of a selective transport molecule into joints. In some embodiments, a carrier decreases uptake of a selective transport molecule into the liver. In some embodiments, a carrier decreases uptake of a selective transport molecule into kidneys.

In some embodiments, a carrier increases plasma half-life and solubility by reducing glomerular filtration. In some embodiments, a carrier increases tumor uptake due to enhanced permeability and retention (EPR) of tumor vasculature. See, Table 2 and Example 8 for comparison of free selective transport molecules vs. selective transport molecules conjugated to a carrier in tissue excision surgery.

TABLE 2

| | | Free Selective Transport Molecules | Dendrimer Selective Transport Molecules |
|---|---|---|---|
| MDA-MB 435 | Tumor | 0.17 ± 0.05 (n = 3) | 1.065 ± 0.55 (n = 3) |
| | Muscle | 0.29 ± 0.068 (n = 3) | 0.238 ± 0.007 (n = 3) |
| | Ratio | 2.45 (p = 0.0004) | 4.46 (p = 0.031) |
| HT1080 | Tumor | 0.42 ± 0.08 (n = 4) | 1.8 ± 0.6 (n = 8) |
| | Muscle | 0.11 ± 0.08 (n = 4) | 0.21 ± 0.07 (n = 8) |
| | Ratio | 3.82 (p = 0.022) | 8.6 (p = 0.0009) |
| 8119 | Tumor | 0.39 ± 0.12 (n = 5) | 2.191 ± 0.743 (n = 3) |
| | Muscle | 0.11 ± 0.06 (n = 5) | 0.166 ± 0.023 (n = 3) |
| | Ratio | 3.5 (p = 0.006) | 13.2 (p = 0.004) |
| B16F10 | Tumor | 0.24 ± 0.06 (n = 4) | 1.069 ± 0.575 (n = 3) |
| | Muscle | 0.10 ± 0.03 (n = 3) | 0.191 ± 0.014 (n = 3) |
| | Ratio | 2.4 (p = 0.014) | 5.6 (p = 0.028) |

In some embodiments, M is bound to A. In some embodiments, M is bound to A at the n-terminal poly glutamate. In some embodiments, M is bound to A (or, the n-terminal poly glutamate) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, M is bound to B. In some embodiments, M is bound to B at the c-terminal polyarginine. In some embodiments, M is bound to B (or, the c-terminal polyarginine) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, M is selected from a protein, a synthetic or natural polymer, or a dendrimer. In some embodiments, M is selected from dextran, a PEG polymer (e.g., PEG 5 kDa and PEG 12 kDa), albumin, or a combination thereof. In some embodiments, M is a PEG polymer.

In some embodiments, the size of the carrier is between 50 and 70 kD. In some embodiments, small amounts of negative charge keep peptides out of the liver while not causing synovial uptake.

In some embodiments, the selective transport molecule is conjugated to albumin. In certain instances, albumin is excluded from the glomerular filtrate under normal physiological conditions. In some embodiments, the selective transport molecule comprises a reactive group such as maleimide that can form a covalent conjugate with albumin. A selective transport molecule comprising albumin results in enhanced accumulation of cleaved selective transport molecules in tumors in a cleavage dependent manner. See, Example 2. In some embodiments, albumin conjugates have good pharmacokinetic properties but are difficult to work with synthetically.

In some embodiments, the selective transport molecule is conjugated to a PEG polymer. In some embodiments, the selective transport molecule is conjugated to a PEG 5 kDa polymer. In some embodiments, the selective transport molecule is conjugated to a PEG 12 kDa polymer. In some embodiments, 5 kD PEG conjugates behaved similarly to free peptides. In some embodiments, 12 kD PEG conjugates had a longer halflife as compared to free peptides. See Example 5 for a detailed analysis of the effects of using a PEG polymer.

In some embodiments, the selective transport molecule is conjugated to a dextran. In some embodiments, the selective transport molecule is conjugated to a 70 kDa dextran. In some embodiments, dextran conjugates, being a mixture of molecular weights, are difficult to synthesize and purify reproducibly. See Example 5 for a detailed analysis of the effects of using a dextran.

In some embodiments, the selective transport molecule is conjugated to streptavidin. See Example 5 for a detailed analysis of the effects of using streptavidin.

In some embodiments, the selective transport molecule is conjugated to a fifth generation PAMAM dendrimer. See Example 5 for a detailed analysis of the effects of using a dendrimer.

For details on changes to plasma half-life and uptake, see Table 3.

TABLE 3

| Peptide Structure | Approx Purity by gel | Dose/Time at Sacrifice | Approx Plasma Halflife | Tumor Uptake (SUV) (mean ± SD) | Liver Uptake (SUV) (mean ± SD) | Kidney Uptake (SUV) (mean ± SD) |
|---|---|---|---|---|---|---|
| 12kD-PEG-$e_9$-XPLGLAG-$r_9$-k(cy5) | >90% | 6 nmol 1 h | 20 m | 0.51 ± 0.13 (n = 7) | 1.58 ± 0.79 (n = 7) | 3.38 ± 1.33 (n = 7) |
| 12kD PEG-$e_9$-Xplglag-$r_9$-k(cy5) | >90% | 6 nmol 1 h | NA | 0.26 ± 0.09 (n = 4) | 2.52 ± 0.65 (n = 4) | 7.10 ± 2.38 (n = 4) |
| 12kD-PEG-$e_9$-XPLGLAG-$r_9$-k(cy5) | >90% | 6 nmol 1 h | NA | 0.68 ± 0.17 (n = 2) | 1.17 ± 0.49 (n = 2) | 5.33 ± 0.64 (n = 2) |
| 12kD PEG-$e_9$-Xplglag-$r_9$-k(cy5) | >90% | 6 nmol 1 h | NA | 0.31 ± 0.18 (n = 2) | 0.71 ± 0.17 (n = 2) | 3.27 ± 0.62 (n = 2) |
| Alb-$e_9$-XPLGLAG-$r_9$-k(cy5) | ~60% | 4.8 nmol 48 h | 3 h | 0.9 ± 0.3 (n = 2) | 8.3 ± 2.9 (n = 2) | 2.8 ± 1.0 (n = 2) |
| Alb-$e_9$-Xplglag-$r_9$-k(cy5) | ~40% | 6 nmol 48 h | NA | 0.2 ± 0.1 (n = 2) | 11.8 ± 1.1 (n = 2) | 5.4 ± 0.2 (n = 2) |
| Dex-$e_9$-XPLGLAG-$r_9$-k(cy5) | Not assessed | 5 nmol 48 h | 6 h | 2.3 ± 2.0 (n = 2) | 14.2 ± 7.1 (n = 2) | 3.3 ± 1.9 (n = 2) |
| Dex-$e_9$-Xplglag-$r_9$-k(cy5) | Not assessed | 6 nmol 48 h | NA | 0.5 ± 0.2 (n = 2) | 11.1 ± 1.5 (n = 2) | 6.1 ± 0.5 (n = 2) |
| Streptavidin-[$e_9$-XPLGLAG-$r_9$-k(cy5)]$_4$ | Not assessed | 4 nmol 48 h | 4 h | 0.4 ± 0.0 (n = 2) | 3.2 ± 0.0 (n = 2) | 3.7 ± 1.0 (n = 2) |
| G5 PAMAM-[$e_9$-XPLGLAX-$r_9$-k(cy5)]$_2$[Succ]$_{126}$ | 60% | 3 nmol 24 h | NA | 1.4 ± 0.4 (n = 2) | 6.6 ± 2.1 (n = 2) | 1.8 ± 0.4 (n = 2) |
| G5-PAMAM[$e_9$-XPLGLAX-$r_9$-k(cy5)]$_2$ [PEG]$_{126}$ | >90% | 3 nmol 24 h | 20 h | 1.2 ± 0.1 (n = 3) | 4.1 ± 0.7 (n = 3) | 2.0 ± 0.2 (n = 3) |
| G5PAMAM-[$e_9$-XPLGLAX-$r_9$-k(cy5)]$_2$ [PEG]$_{126}$ | >90% | 3 nmol 48 h | NA | 1.36 ± 0.13 (n = 3) | 5.89 ± 0.55 (n = 3) | 2.09 ± 0.34 (n = 3) |
| G5PAMAM-[$e_9$-XPLGLAG-$r_9$-k(cy5)] [PEG]$_{127}$ | >90% | 3 nmol 48 h | NA | 0.6 ± 0.1 (0.5, 0.7) n = 2 | 3.5 ± 1.7 (2.3, 4.7) n = 2 | 1.1 ± 0.0 (1.1, 1.1) n = 2 |
| G5PAMAM-[$e_9$-OPLG(MeC)AG-$r_9$-k(cy5)] [PEG]$_{127}$] | >90% | 3 nmol 48 h | | 0.7 ± 0.5 (0.2-1.2) n = 3 | 1.8 ± 0.8 (0.9-2.3) n = 3 | 1.3 ± 0.4 (1.0-1.7) n = 3 |

In some embodiments, a carrier is capped. See Example 1 for methods of capping. In some embodiments, capping a carrier improves the pharmacokinetics and reduces cytotoxicity of a carrier by adding hydrophilicity. In some embodiments, the cap is selected from: Acetyl, succinyl, 3-hydroxypropionyl, 2-sulfobenzoyl, glycidyl, PEG-2, PEG-4, PEG-8 and PEG-12. For a detailed analysis of the effects of capping, see Example 6.

Dendrimers

Disclosed herein, in certain embodiments, is a selective transport molecule. In some embodiments, a selective transport molecule disclosed herein has the formula (A-X-B)$_n$-D, wherein D is a dendrimer; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and n is an integer between 1 and 20; and wherein D is bound to an (A-X-B) moiety by a bond with a B. In some embodiments, D is bound to an (A-X-B) moiety by a bond with a polyarginine terminus. In some embodiments, D comprises at least one cargo moiety. See Example 1 for method of conjugating a peptide to a dendrimer.

As used herein, "dendrimer" means a poly-functional (or, poly-branched) molecule. In some embodiments, a dendrimer is a structure in which a central molecule branches repetitively and repetitiously. In some embodiments, the dendrimer is a nanoparticle.

In some embodiments, D is bound to B (or, the c-terminal polyarginine) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, a plurality of (A-X-B) moieties are attached to D. See, Example 3. In some embodiments, a plurality of cargo moieties are attached to D. In some embodiments, (a) a plurality of (A-X-B) moieties are attached to D; and (b) a plurality of cargo moieties are attached to D.

In some embodiments, the dendrimer comprises a reactive group such as maleimide that can form a covalent conjugate with albumin. In some embodiments, a dendrimer is conjugated to a selective transport molecule via a maleimide linker at the C-terminal end of the selective transport molecule.

In some embodiments, conjugating a selective transport molecule to a dendrimer increases plasma half-life as compared to an unconjugated (or, free) selective transport molecule. In some embodiments, a selective transport molecule conjugated to a dendrimer results in a decrease in acute toxicity as compared to unconjugated selective transport molecules. In some embodiments, a selective transport molecule conjugated to a dendrimer reduces uptake by synovium, cartilage and kidney as compared to unconjugated selective transport molecules.

In some embodiments, a selective transport molecule conjugated to a dendrimeric nanoparticle is used to target tumor associated macrophages. In some embodiments, a selective transport molecule conjugated to a dendrimeric nanoparticle, wherein the nanoparticle further comprises Ricin A, is used to poison subcutaneous macrophages. See Example 7 for a detailed analysis of the effects of using a dendrimeric nanoparticle.

Cargo

Disclosed herein, in certain embodiments, is a selective transport molecule with increased in vivo circulation.

In some embodiments, a selective transport molecule disclosed herein has the formula (A-X-B-C)-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and M is a macromolecular carrier.

In some embodiments, a selective transport molecule disclosed herein has the formula (A-X-B)-D, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and D is a dendrimer. In some embodiments, D comprises a cargo moiety. See Example 1 for methods of attaching a label to a selective transport molecule.

Selective transport molecules disclosed herein are suitable for carrying different cargoes, including different types of cargoes and different species of the same types of cargo, for uptake into cells. For example, different types of cargo may include marker cargoes (e.g., fluorescent or radioactive label moieties) and therapeutic cargoes (e.g., chemotherapeutic molecules such as methotrexate or doxorubicin), or other cargoes. Where destruction of aberrant or diseased cells is therapeutically required, a therapeutic cargo may include a "cytotoxic agent," i.e., a substance that inhibits or prevents the function of cells and/or causes destruction of cells.

Delivery of cargo such as a fluorescent molecule may be used to visualize cells having a certain condition or cells in a region exhibiting a particular condition. For example, thrombosis (clot formation) may be visualized by designing a linker X to be cleaved by any of the many proteases in the blood clot formation cascade for delivery of a cargo including a fluorescent or other marker to the region. Similarly, complement activation may be visualized by designing a linker X to be cleaved by any one or more of the proteases in the complement activation cascades for delivery of a fluorescent or other marker to the region. Thus, fluorescent molecules are one example of a marker that may be delivered to target cells and regions upon release of a portion A upon cleavage of a linker X.

In some embodiments, the cargo moiety is selected from an imaging agent, a therapeutic agent, a lipid, or a combination thereof.

In some embodiments, the cargo portion comprises at least two cargo moieties. In some embodiments, C comprises a marker cargo and a therapeutic cargo. Multiple cargo moieties may allow, for example, delivery of both a radioactive marker and an ultrasound or contrast agent, allowing imaging by different modalities. Alternatively, for example, delivery of radioactive cargo along with an anticancer agent, providing enhanced anticancer activity, or delivery of a radioactive cargo with a fluorescent cargo, allowing multiple means of localizing and identifying cells which have taken up cargo.

Attachment of a Cargo Moiety

The cargo moiety is attached to B in any location or orientation. The cargo moiety need not be located at an opposite end of portion B than a linker X. Any location of attachment of the cargo moiety to B is acceptable as long as that attachment remains after X is cleaved. For example, the cargo moiety may be attached to or near to an end of portion B with linker X attached to an opposite end of portion B as illustrated in FIGS. 2A and 2B. The cargo moiety may also be attached to or near to an end of portion B with linker X attached to or near to the same end of portion B.

Wherein the molecule comprises a dendrimer, the cargo is attached directly to D. By way of non-limiting example, the cargo is attached as follows:

(A-X-B)-D-cargo.

In some embodiments, a cargo moiety is bound to B (or, the c-terminal polyarginine) or D by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

Imaging Agents as Cargo In some embodiments, a cargo moiety is a fluorescent molecule such as fluorescein. Fluorescent cargo moieties enable easy measurement by fluorescence microscopy or flow cytometry in unfixed cultured cells.

In some embodiments, a cargo moiety is labeled with a positron-emitting isotope (e.g. $^{18}$F) for positron emission tomography (PET), gamma-ray isotope (e.g., $^{99m}$Tc) for single photon emission computed tomography (SPECT), a paramagnetic molecule or nanoparticle (e.g., Gd$^{3+}$ chelate or coated magnetite nanoparticle) for magnetic resonance imaging (MRI), a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound.

In some embodiments, a cargo moiety is a radioactive moiety, for example a radioactive isotope such as $^{211}$At, $^{131}$I, $^{125}$I, $^{90}$Y, $^{186}$Re, $^{188}$Re, $^{153}$Sm, $^{212}$Bi, $^{32}$P, radioactive isotopes of Lu, and others.

In some embodiments, a cargo moiety is a fluorescent moiety, such as a fluorescent protein, peptide, or fluorescent dye molecule. Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. Nos. 4,452,720, 5,227,487, and 5,543,295.

In some embodiments, a cargo moiety is a fluorescein dye. Typical fluorescein dyes include, but are not limited to, 5-carboxyfluorescein, fluorescein-5-isothiocyanate and 6-carboxyfluorescein; examples of other fluorescein dyes can be found, for example, in U.S. Pat. Nos. 6,008,379, 5,750,409, 5,066,580, and 4,439,356. A cargo moiety C may include a rhodamine dye, such as, for example, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®), and other rhodamine dyes. Other rhodamine dyes can be found, for example, in U.S. Pat. Nos. 6,080,852, 6,025,505, 5,936,087, 5,750,409. A cargo moiety C may include a cyanine dye, such as, for example, Cy3, Cy3B, Cy3.5, Cy5, Cy5.5, Cy 7.

Some of the above compounds or their derivatives will produce phosphorescence in addition to fluorescence, or will only phosphoresce. Some phosphorescent compounds include porphyrins, phthalocyanines, polyaromatic compounds such as pyrenes, anthracenes and acenaphthenes, and so forth, and may be, or may be included in, a cargo moiety. A cargo moiety may also be or include a fluorescence quencher, such as, for example, a (4-dimethylamino-phenylazo)benzoic acid (DABCYL) group.

In some embodiments, a cargo moiety is a fluorescent label. In some embodiments, a cargo moiety is indocarbocyanine dye, Cy5, Cy5.5, Cy7, IRDYE 800CW, ALEXA647, or a combination thereof. In some embodiments, a cargo moiety is a MRI contrast agent. In some embodiments, a cargo moiety is Gd complex of [4,7,10-tris (carboxymethyl)-1,4,7,10-tetraazacyclododec-1-yl]acetyl.

In some embodiments, a cargo moiety is all or part of a molecular beacon. As used herein, "molecular beacon" means a pair of connected compounds having complementary regions with a fluorophore and a fluorescent quencher so that the fluorescence of the fluorophore is quenched by the quencher. One or both of the complementary regions may be part of the cargo moiety. Where only one of the complementary regions (e.g., the fluorescent moiety) is part of the cargo moiety, and where the quencher moiety is part of the linker X or the acidic portion A, then cleavage of the linker X will allow fluorescence of the fluorescent portion and detection of the cleavage. Upon cellular uptake, the fluorescent portion of a molecular beacon will allow detection of the cell. For example, a quencher Q may be attached to an acidic portion A to form a selective transport molecule having features of the invention Q-A-X-B-C where cargo is fluorescent and is quenched by Q. The quenching of the cargo moiety by Q is relieved upon cleavage of X, allowing fluorescent marking of a cell taking up portion B-C. The combination of fluorescence dequenching and selective uptake should increase contrast between tissues able to cleave X compared to those that cannot cleave X.

Therapeutic Agents as Cargo

In some embodiments, a cargo moiety is a therapeutic agent, such as a chemical compound useful in the treatment of cancer, ischemic tissue, or necrotic tissue.

For therapeutic purposes, for example, suitable classes of cargo include but are not limited to: a) chemotherapeutic agents; b) radiation sensitizing agents; or c) peptides or proteins that modulate apoptosis, the cell cycle, or other crucial signaling cascades.

In some embodiments, a cargo moiety is an agent that modulates cell death (e.g., via apoptosis or necrosis). In some embodiments, a cargo moiety is a pro-apoptotic agent. In some embodiments, the drug is an anti-apoptotic agent. In some embodiments, the drug is selected from: minocycline; SB-203580 (4-(4-Fluorophenyl)-2-(4-methylsulfinyl phenyl)-5-(4-pyridyl) 1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (5-(2-Amino-4-pyrimidinyl)-4-(4-fluorophenyl)-1-(4-piperidinyl)imidazole); D-JNKI-1 ((D)-hJIP175-157-DPro-DPro-(D)-HIV-TAT57-48); AM-111 (Auris); SP600125 (anthra[1,9-cd]pyrazol-6(2H)-one); JNK Inhibitor I ((L)-HIV-TAT48-57-PP-JBD20); JNK Inhibitor III ((L)-HIV-TAT47-57-gaba-c-Junδ33-57); AS601245 (1,3-benzothiazol-2-yl (2-[12-(3-pyridinyl) ethyl]amino]-4 pyrimidinyl) acetonitrile); JNK Inhibitor VI (H2N-RPKRPTTLNLF-NH2 (SEQ ID NO: 37)); JNK Inhibitor VIII (N-(4-Amino-5-cyano-6-ethoxypyridin-2-yl)-2-(2,5-dimethoxyphenyl)acetamide); JNK Inhibitor IX (N-(3-Cyano-4,5,6,7-tetrahydro-1-benzothien-2-yl)-1-naphthamide); dicumarol (3,3'-Methylenebis(4-hydroxycoumarin)); SC-236 (445-(4-chlorophenyl)-3-(trifluoromethyl)-1H-pyrazol-1-yl]benzene-sulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel blocker ((±)-1-(3,6-Dibromocarbazol-9-yl)-3-piperazin-1-yl-propan-2-01); Bax inhibiting peptide P5 (also known as Bax inhibitor peptide P5); Kp7-6; FAIM(S) (Fas apoptosis inhibitory molecule-short); FAIM (L) (Fas apoptosis inhibitory molecule-long); Fas:Fc; FAP- 1; NOK2; F2051; F1926; F2928; ZB4; Fas M3 mAb; EGF; 740 Y-P; SC 3036 (KKHTDDGYMPMSPGVA (SEQ ID NO: 38)); PI 3-kinase Activator (Santa Cruz Biotechnology, Inc.); Pam3Cys ((S)-(2,3-bis(palmitoyloxy)-(2RS)-propyl)-N-palmitoyl-(R)-Cys-(S)-Ser(S)-Lys4-OH, trihydrochloride); Act1 (NF-kB activator 1); an anti-IkB antibody; Acetyl-11-keto-b-Boswellic Acid; Andrographolide; Caffeic Acid Phenethyl Ester (CAPE); Gliotoxin; Isohelenin; NEMO-Binding Domain Binding Peptide (DRQIKIWFQNRRMKWKKTALDWSWLQTE (SEQ ID NO: 39)); NF-kB Activation Inhibitor (6-Amino-4-(4-phenoxyphenylethylamino)quinazoline); NF-kB Activation Inhibitor II (4-Methyl-N1-(3-phenylpropyl)benzene-1,2-diamine); NF-kB Activation Inhibitor III (3-Chloro-4-nitro-N-(5-nitro-2-thiazolyl)-benzamide); NF-kB Activation Inhibitor IV ((E)-2-Fluoro-4'-methoxystilbene); NF-kB Activation Inhibitor V (5-Hydroxy-(2,6-diisopropylphenyl)-1H-isoindole-1,3-dione); NF-kB SN50 (AAVALLPAVLLALLAPVQRKRQKLMP (SEQ ID NO: 40)); Oridonin; Parthenolide; PPM-18 (2-Benzoylamino-1,4-naphthoquinone); Ro106-9920; Sulfasalazine; TIRAP Inhibitor Peptide (RQIKIWFNRRMKWKKLQLRDAAPGGAIVS (SEQ ID NO: 41)); Withaferin A; Wogonin; BAY 11-7082 ((E)3 [4(4-Methylphenyl)sulfonyl]-2-propenenitrile); BAY 11-7085 ((E)3-[(4-t-Butylphenyl)sulfonyl]-2-propenenitrile); (E)-Capsaicin; Aurothiomalate (ATM or AuTM); Evodiamine; Hypoestoxide; IKK Inhibitor III (BMS-345541); IKK Inhibitor VII; IKK Inhibitor X; IKK Inhibitor II; IKK-2 Inhibitor IV; IKK-2 Inhibitor V; IKK-2 Inhibitor VI; IKK-2 Inhibitor (SC-514); IkB Kinase Inhibitor Peptide; IKK-3 Inhibitor IX; ARRY-797 (Array BioPharma); SB-220025 (5-(2-Amino-4-pyrimidinyl)-4-(4-fluorophenyl)-1-(4-piperidinlypimidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl)1H-imidazole); JX-401 (-[42-Methoxy-4-(methylthio)benzoyl]-4-(phenylmethyl) piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo[2,1-b]thiazole dihydrochloride); SB-200646 (N-(1-Methyl-1H-indol-5-yl)-N'-3-pyridinylurea); CMPD-1 (2'-Fluoro-N-(4-hydroxyphenyl)-[1,1'-biphenyl]-4-butanamide); EO-1428 ((2-Methylphenyl)-[4-[(2-amino-4-bromophenyl)amino]-2-chlorophenyl]methanone); SB-253080 (4-[5-(4-Fluorophenyl)-2-[4-(methylsulfonyl)phenyl]-1H-imidazol-4-yl]pyridine); SD-169 (1H-Indole-5-carboxamide); SB-203580 (4-(4-Fluorophenyl)-2-(4-methylsulfinylphenyl)-5-(4-pyridyl) 1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1,1'-biphenyl)-4-yl) methyl)-1H-1-benzazepin-3-yl)-, (R)-); EP1572 (Aib-DTrp-DgTrp-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; piperine; hemin; brazilin; z-VAD-FMK (Benzyloxycarbonyl-Val-Ala-Asp(OMe)-fluoromethylketone); z-LEHD-FMK (SEQ ID NO: 42) (benzyloxycarbonyl-Leu-Glu(OMe)-His-Asp(OMe)-fluoromethylketone); B-D-FMK (boc-aspartyl(Ome)-fluoromethylketone); Ac-LEHD-CHO (SEQ ID NO: 43) (N-acetyl-Leu-Glu-His-Asp-CHO); Ac-IETD-CHO (SEQ ID NO: 44) (N-acetyl-Ile-Glu-Thr-Asp-CHO); z-IETD-FMK (SEQ ID NO: 45) (benzyloxycarbonyl-Ile-Glu(OMe)-Thr-Asp(OMe)-fluoromethylketone); FAM-LEHD-FMK (SEQ ID NO: 46) (benzyloxycarbonyl Leu-Glu-His-Asp-fluoromethyl ketone); FAM-LETD-FMK (SEQ ID NO: 47) (benzyloxycarbonyl Leu-Glu-Thr-Asp-fluoromethyl ketone); Q-VD-OPH (Quinoline-Val-Asp-CH2-O-Ph); XIAP; cIAP-1; cIAP-2; ML-IAP; ILP-2; NAIP; Survivin; Bruce; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-[(phenylmethoxy)carbonyl]-L-leucyl-N-[(IS)-1-formyl-3-methylbutyl] L-leucinamide); MYODUR; BN 82270 (Ipsen); BN 2204 (Ipsen); AHLi-11 (Quark Pharmaceuticals), an mdm2 protein, pifithrin-α(1-(4-Methylphenyl)-2-(4,5,6,7-tetrahydro-2-imino-3(2H)-benzothiazolyl)ethanone); trans-stilbene; cisstilbene; resveratrol; piceatannol; rhapontin; deoxyrhapontin; butein; chalcon; isoliquirtigen; butein; 4,2',4'-trihydroxychalcone; 3,4,2',4',6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.H2O); Ambroxol (trans-4-(2-Amino-3,5-dibromobenzylamino)cyclohexane-HCL; and U-83836E ((−)-2-((4-(2,6-di-1-Pyrrolidinyl-4-pyrimidinyl)-1-piperazinyl) methyl)-3,4-dihydro-2,5,7,8-tetramethyl-2H-1-benzopyran-6-ol.2HCl); β-1'-5-methyl-nicotinamide-2'-deoxyribose; β-D-1'-5-methyl-nico-tinamide-2'-deoxyribofuranoside; β1'-4,5-dimethyl-nicotinamide-2'-deoxyribose; β-D-1'-4,5-dimethyl-nicotinamide-2'-deoxyribofuranoside; 1-Naphthyl PP1 (1-(1,1-Dimethylethyl)-3-(1-naphthalenyl)-1H-pyrazolo[3, 4-d]pyrimidin-4-amine); Lavendustin A (5-[[(2,5-Dihydroxyphenyl)methyl][(2-hydroxyphenyl)methyl] amino]-2-hydroxybenzoic acid); MNS (3,4-Methylenedioxy-b-nitrostyrene); PP1 (1-(1,1-Dimethylethyl)-1-(4-methylphenyl)-1H-pyrazolo[3,4-d] pyrimidin-4-amine); PP2 (3-(4-chlorophenyl) 1-(1,1-dimethylethyl)-1H-pyrazolo[3,4-d]pyrimidin-4-amine); KX-004 (Kinex); KX-005 (Kinex); KX-136 (Kinex); KX-174 (Kinex); KX-141 (Kinex); KX2-328 (Kinex); KX-306 (Kinex); KX-329 (Kinex); KX2-391 (Kinex); KX2-377 (Kinex); ZD4190 (Astra Zeneca; N-(4-bromo-2-fluorophenyl)-6-methoxy-7-(2-(1H-1,2,3-triazol-1-yl)ethoxy)quinazolin-4-amine); AP22408 (Ariad Pharmaceuticals); AP23236 (Ariad Pharmaceuticals); AP23451 (Ariad Pharmaceuticals); AP23464 (Ariad Pharmaceuticals); AZD0530 (Astra Zeneca); AZM475271 (M475271; Astra Zeneca); Dasatinib (N-(2-chloro-6-methylphenyl)-2-(6-(4-(2-hydroxyethyl)-piperazin-1-yl)-2-methylpyrimidin-4-ylamino) thiazole-5-carboxamide); GN963 (trans-4-(6,7-dimethoxyquinoxalin-2ylamino)cyclohexanol sulfate); Bosutinib (4-((2,4-dichloro-5-methoxyphenyl)amino)-6-methoxy-7-(3-(4-methyl-1-piperazinyl)propoxy)-3-quinolinecarbonitrile); or combinations thereof.

In some embodiments, a cargo moiety is a cytotoxic agent. In some embodiments, a cargo moiety is maytansine, methotrexate (RHEUMATREX®, Amethopterin); cyclophosphamide (CYTOXAN®); thalidomide (THALIDOMID®)); paclitaxel; pemetrexed; pentostatin; pipobroman; pixantrone; plicamycin; procarbazine; proteasome inhibitors (e.g.; bortezomib); raltitrexed; rebeccamycin; rubitecan; SN-38; salinosporamide A; satraplatin; streptozotocin; swainsonine; tariquidar; taxane; tegafururacil; temozolomide; testolactone; thioTEPA; tioguanine; topotecan; trabectedin; tretinoin; triplatin tetranitrate; tris(2-chloroethyl) amine; troxacitabine; uracil mustard; valrubicin; vinblastine; vincristine; vinorelbine; vorinostat; zosuquidar; or a combination thereof.

Lipids as Cargo

Disclosed herein, in certain embodiments, is a selective transport molecule. In some embodiments, a selective transport molecule disclosed herein has the formula $(A-X-B)_n$-L, wherein L is a lipid; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X is a linker. See Example 4 for a detailed analysis of the effects of using a lipid encapsulated therapeutic agent as cargo.

In some embodiments, L is bound to B (or, the c-terminal polyarginine) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond. In some embodiments, L is bound to B by a non-covalent interaction.

In some embodiments, a plurality of (A-X-B) moieties are attached to L. See, Example 3. In some embodiments, a plurality of cargo moieties are encapsulated by L. In some embodiments, (a) a plurality of (A-X-B) moieties are attached to L; and (b) a plurality of cargo moieties are encapsulated by L.

In some embodiments, the lipid entraps a hydrophobic molecule. In some embodiments, the lipid entraps at least one agent selected from the group consisting of a therapeutic moiety or an imaging moiety. In some embodiments, the agent is doxorubicin. In some embodiments, the agent is paclitaxel. In some embodiments, the agent is tamoxifen. In some embodiments, the agent is selected from: aloxiprin, acebutolol, acetazolamide, acetohexamide, acrivastine, albendazole, allopurinol, alprazolam, alprenolol, amiloride, aminoglutethimide, amiodarone HCl, amlodipine, amodiaquine, amoxapine, amphetamine, amphotericin, amrinone, amsacrine, amyl nitrate, amylobarbitone, astemizole, atenolol, atropine, auranofin, azapropazone, azathioprine, barbitone, beclamide, beclomethasone, bendrofluazide, benidipine, benorylate, bentazepam, benzhexol HCl, benznidazole, bephenium hydroxynaphthoate, betacarotene, betamethasone, bezafibrate, biperiden, bisacodyl, bromazepam, bromocriptine mesylate, bromperidol, brotizolam, budesonide, bumetanide, busulphan, butobarbitone, butoconazole nitrate, cambendazole, carbamazepine, carbimazole, carbromal, chlorambucil, chlordiazepoxide, chlormethiazole, chloroquine, chlorothiazide, chlorproguanil HCL, chlorpromazine, chlorpropamide, chlorthalidone, cimetidine, cinnarizine, cinoxacin, ciprofloxacin HCl, cisapride, clarithromycin, clioquinol, clobazam, clofazimine, clofibrate, clomiphene citrate, clonazepam, clotiazepam, clotrimazole, cloxacillin, clozapine, codeine, conjugated oestrogens, cortisone acetate, cyclizine, cyclosporin, cyproheptadine HCl, dacarbazine, danazol, darodipine, decoquinate, demeclocycline, desoxymethasone, dexamethasone, dexamphetamine, dexfenfluramine, dextropropyoxyphene, diamorphine, diazepam, diazoxide, dichlorophen, dicoumarol, diflunisal, digitoxin, digoxin, dihydrocodeine, dihydroergotamine mesylate, diiodohydroxyquinoline, diltazem HCl, diloxanide furoate, dimenhydrinate, dinitolmide, diphenoxylate HCl, dipyridamole, disopyramide, domperidone, doxycycline, droperidol, econazole nitrate, enoximone, ergotamine tartrate, erythromycin, estradiol, estramustine, ethacrynic acid, ethinamate, ethinyl estradiol, ethionamide, ethopropazine HCl, ethotoin, etodolac, etoposide, famotidine, felodipine, fenbufen, fenfluramine, fenofibrate, fenoprofen calcim, flecainide acetate, fluconazole, flucortolone, flucytosine, fludrocortisone acetate, flunanisone, flunarizine HCl, flunisolide, flunitrazepam, fluoprmazine, flupenthixol decanoate, fluphenazine decanoate, flurazepam, flurbiprofen, fluticasone propionate, frusemide, furzolidone, gemfibrozil, glibenclamide, gliclazide, glipizide, glyceryl trinitrate, griseofulvin, guanabenz acetate, halofantrine HCl, haloperidol, hydrocortisone, hyoscyamine, ibuprofen, imipenem, indomethacin, isosorbide dinitrate, isosorbide mononitrate, isradipine, itraconazole, ivermectin, ketoconazole, ketoprofen, labetalol, lanatoside C, lomustine, loperamide, loratadine, lorazepam, lormetazepam, lysuride maleate, maprotiline HCl, mazindol, mebendazole, meclofenamic acid, meclozine HCl, medazepam, medigoxin, medroxyprogesterone acetate, mefenamic acid, mefloquine HCl, melphalan, mepenzolate bromide, meprobamate, meptazinol, mercaptopurine, mesalazine, mestranol, methadone, methaqualone, methoin, methotrexate, methsuximide, methylphenobarbitone, methylprednisolone, methyltestosterone, methysergide maleate, metolazone, metoprolol, metronidazole, mianserin HCL, miconazole, midazolam, minoxidil, mitomycin, mitotane, mitozantrone, morphine, nabumetone, nadolol, nalbuphine, nalidixic acid, naproxen, natamycin, nicardipine HCl, nicoumalone, nifedipine, nimodipine, nimorazole, nitrazepam, nitrofurantoin, nitrofurazone, nizatidine, norethisterone, norgestrel, nortriptyline HCl, nystatin, omeprazole, ondansetron HCL, ornidazole, oxamniquine, oxantel embonate, oxatomide, oxazepam, oxcarbazepine, oxfendazole, oxprenolol, oxyphenbutazone, oxyphencylcimine HCl, paclitaxel, paramethadione, pentaerythritol tetranitrate, pentazocine, pentobarbitone, perphenazine pimozide, phenacemide, phenindione, phenobarbitone, phenoxybenzamine HCl, phensuximide, phenylbutazone, phenytoin, pindolol, piroxicam, pizotifen maleate, praziquantel, prazosin HCL, prednisolone, prednisone, primidone, probenecid, probucol, procarbazine HCl, prochlorperazine, progesterone, proguanil HCl, propranolol, propylthiouracil, pyrantel embonate, pyrimethamine, quinidine sulphate. Anti-bacterial agents: benethamine penicillin, quinine sulphate, ranitidine HCl, reserpine, rifampicin, spiramycin, spironolactone, stanozolol, stibestrol, sulconazole nitrate, sulindac, sulphabenzamide, sulphacetamide, sulphadiazine, sulphadoxine, sulphafurazole, sulphamerazine, sulphamethoxazole, sulphapyridine, sulphasalazine, sulphin-pyrazone, sulpiride, sulthiame, sumatriptan succinate, tamoxifen citrate, temazepam, terazosin HCL, terbinafine HCl, terconazole, terfenadine, testolactone, testosterone, tetracycline, thiabendazole, thioridazine, tibolone, tinidazole, tioconazole, tolazamide, tolbutamide, trazodone HCL, triamcinolone, triamterene, triazolam, trimethoprim, trimipramine maleate, tropicamide, undecenoic acid, valproic acid, vitamin A, vitamin B 2, vitamin D, vitamin E, vitamin K, zopiclone, or a combination thereof.

In some embodiments, the lipid is PEGylated. In some embodiments, the lipid is PEG(2K)-phosphatidylethanolamine.

Methods of Use

Labeling Tissues

Disclosed herein, in certain embodiments, are methods of labeling a tissue (e.g., to define the surgical margins for a tumor resection) by administering to a patient in need there of a selective transport molecule described herein. In some embodiments, the tissue is a tumor. In some embodiments, the tissue is ischemic tissue. In some embodiments, the tissue is hypoxic tissue. In some embodiments, the tissue is necrotic tissue. In some embodiments, the tissue is acidotic tissue. In some embodiments, the tissue is diseased tissue (e.g., tissue infected by an infectious agent, tissue contacted with a poisonous agent, tissue subject to a autoimmune disorder, tissue that is inflamed).

In some embodiments, the tissue is labeled for identification and removal during surgery. In some embodiments, the method of imaging the surgical margins for a tumor or tissue resection in a subject, comprises imaging the surgical margins after the subject has been administered a selective transport molecule disclosed herein. In some embodiments, the method of imaging a tumor in a subject comprises imaging the tumor after the subject has been administered a selective transport molecule disclosed herein. In some embodiments, the method of removing a tumor in a subject comprises removing the tumor after the subject has been administered a selective transport molecule disclosed herein.

In some embodiments, the method comprises administering a selective transport molecule described herein to a subject that will undergo surgery. In some embodiments, the method comprises administering a selective transport molecule described herein to a subject that is undergoing surgery. In some embodiments, a selective transport molecule described herein is administered to a patient systemically. In some embodiments, a selective transport molecule described herein is administered to a patient locally.

In some embodiments, a selective transport molecule disclosed herein is utilized at multiple stages in the evaluation and treatment of cancer. In some embodiments, a dual modality (MR and fluorescence) selective transport molecule allows pre-operative staging by oncologists and radiologists, particularly for cancers such as prostate where invasion of a capsule is important, preventing surgery on patients who are non-operative candidates. In some embodiments, the anatomical and biochemical information given by the dual label selective transport molecule are useful for surgeons in planning complex surgical procedures. In some embodiments, tight binding of selective transport molecules to the site of cleavage provides localized information regarding tumor biology that not only allows the surgeon to focus on the most invasive areas of tumor growth with intraoperative fluorescence imaging but also allows the pathologist to do the same with intraoperative histology. Following surgery, in some embodiments, the dual probe allows further evaluation for completeness of tumor removal with a second MRI.

Drug Delivery

Disclosed herein, in certain embodiments, are methods of targeted drug delivery. In some embodiments, a selective transport molecule described herein delivers a drug to a specific target (e.g., a cell or a plurality of cells). In some embodiments, a selective transport molecule described herein delivers a drug to a tumor. In some embodiments, a selective transport molecule described herein delivers a drug to ischemic tissue. In some embodiments, a selective transport molecule disclosed herein delivers a drug to hypoxic tissue. In some embodiments, a selective transport molecule described herein delivers a drug to necrotic tissue. In some embodiments, a selective transport molecule described herein delivers a drug to acidotic tissue. In some embodiments, a selective transport molecule described herein delivers a drug to diseased tissue (e.g., tissue infected by an infectious agent, tissue contacted with a poisonous agent, tissue subject to a autoimmune disorder, tissue that is inflamed).

In some embodiments, the drug is an agent that modulates death (e.g., via apoptosis or necrosis) of a cell. In some embodiments, the drug is a cytotoxic agent. In some embodiments, the drug is maytansine, methotrexate (RHEUMATREX®, Amethopterin); cyclophosphamide (CYTOXAN®); thalidomide (THALIDOMID®); paclitaxel; pemetrexed; pentostatin; pipobroman; pixantrone; plicamycin; procarbazine; proteasome inhibitors (e.g.; bortezomib); raltitrexed; rebeccamycin; rubitecan; SN-38; salinosporamide A; satraplatin; streptozotocin; swainsonine; tariquidar; taxane; tegafururacil; temozolomide; testolactone; thio-TEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; or a combination thereof. In some embodiments, the drug is a pro-apoptotic agent. In some embodiments, the drug is an anti-apoptotic agent. In some embodiments, the drug is selected from: minocycline; SB-203580 (4-(4-Fluorophenyl)-2-(4-methylsulfinyl phenyl)-5-(4-pyridyl) 1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-01); SB 220025 (5-2-Amino-4-pyrimidinyl)-4-(4-fluorophenyl)-1-(4-piperidinyl) imidazole); D-JNKI-1 ((D)-hJIP175-157-DPro-DPro-(D)-HIV-TAT57-48); AM-111 (Auris); SP600125 (anthra[1,9-cd]pyrazol-6(2H)-one); JNK Inhibitor I ((L)-HIV-TAT48-57-PP-JBD20); JNK Inhibitor III ((L)-HIV-TAT47-57-gaba-c-Junδ33-57); AS601245 (1,3-benzothiazol-2-yl (2-[[2-(3-pyridinyl) ethyl] amino]-4 pyrimidinyl) acetonitrile); JNK Inhibitor VI (H2N-RPKRPTTLNLF-NH2 (SEQ ID NO: 37)); JNK Inhibitor VIII (N-(4-Amino-5-cyano-6-ethoxypyridin-2-yl)-2-(2,5-dimethoxyphenyl)acetamide); JNK Inhibitor IX (N-(3-Cyano-4,5,6,7-tetrahydro-1-benzothien-2-yl)-1-naphthamide); dicumarol (3,3'-Methylenebis(4-hydroxycoumarin)); SC-236 (4-[5-(4-chlorophenyl)-3-(trifluoromethyl)-1H-pyrazol-1-yl[benzene-sulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel blocker ((±)-1-(3,6-Dibromocarbazol-9-yl)-3-piperazin-1-yl-propan-2-ol); Bax inhibiting peptide P5 (also known as Bax inhibitor peptide P5); Kp7-6; FAIM(S) (Fas apoptosis inhibitory molecule-short); FAIM (L) (Fas apoptosis inhibitory molecule-long); Fas:Fc; FAP-1; NOK2; F2051; F1926; F2928; ZB4; Fas M3 mAb; EGF; 740 Y-P; SC 3036 (KKHTDDGYMPMSPGVA (SEQ ID NO: 38)); PI 3-kinase Activator (Santa Cruz Biotechnology, Inc.); Pam3Cys ((S)-(2,3-bis(palmitoyloxy)-(2RS)-propyl)-N-palmitoyl-(R)-Cys-(S)-Ser(S)-Lys4-OH, trihydrochloride); Act1 (NF-kB activator 1); an anti-IkB antibody; Acetyl-11-keto-b-Boswellic Acid; Andrographolide; Caffeic Acid Phenethyl Ester (CAPE); Gliotoxin; Isohelenin; NEMO-Binding Domain Binding Peptide (DRQIKIWFQNRRMKWKKTALDWSWLQTE (SEQ ID NO: 39)); NF-kB Activation Inhibitor (6-Amino-4-(4-phenoxyphenylethylamino)quinazoline); NF-kB Activation Inhibitor II (4-Methyl-N1-(3-phenylpropyl)benzene-1,2-diamine); NF-kB Activation Inhibitor III (3-Chloro-4-nitro-N-(5-nitro-2-thiazolyl)-benzamide); NF-kB Activation Inhibitor IV ((E)-2-Fluoro-4'-methoxystilbene); NF-kB Activation Inhibitor V (5-Hydroxy-(2,6-diisopropylphenyl)-1H-isoindole-1,3-dione); NF-kB SN50 (AAVALLPAVLLALLAPVQRKRQKLMP (SEQ ID NO: 40)); Oridonin; Parthenolide; PPM-18 (2-Benzoylamino-1,4-naphthoquinone); Ro106-9920; Sulfasalazine; TIRAP Inhibitor Peptide (RQIKIWFNRRMKWKKLQLRDAAPGGAIVS (SEQ ID NO: 41)); Withaferin A; Wogonin; BAY 11-7082 ((E)3-[(4-Methylphenyl)sulfonyl]-2-propenenitrile); BAY 11-7085 ((E)3-[(4-t-Butylphenyl) psulfonyl]-2-propenenitrile); (E)-Capsaicin; Aurothiomalate (ATM or AuTM); Evodiamine; Hypoestoxide; IKK Inhibitor III (BMS-345541); IKK Inhibitor VII; IKK Inhibitor X; IKK Inhibitor II; IKK-2 Inhibitor IV; IKK-2 Inhibitor V; IKK-2 Inhibitor VI; IKK-2 Inhibitor (SC-514); IkB Kinase Inhibitor Peptide; IKK-3 Inhibitor IX; ARRY-797 (Array BioPharma); SB-220025 (5-(2-Amino-4-pyrimidinyl)-4-(4-fluorophenyl)-1-(4-piperidinyl)imidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl)1H-imidazole); JX-401 (-[2-Methoxy-4-(methylthio)benzoyl]-4-(phenylmethyl) piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo[2,1-b]thiazole dihydrochloride); SB-200646 (N-(1-Methyl-1H-indol-5-yl)-N-3-pyridinylurea); CMPD-1 (2'-Fluoro-N-(4-hydroxyphenyl)-[1,1'-biphenyl]-4-butanamide); EO-1428 ((2-Methylphenyl)-[4-[(2-amino-4-bromophenylamino]-2-chlorophenyl]methanone); SB-253080 (4-[5-(4-Fluorophenyl)-2-[4-(methylsulfonyl)phenyl]-1H-imidazol-4-yl]pyridine); SD-169 (1H-Indole-5-carboxamide); SB-203580 (4-(4-Fluorophenyl)-2-(4-methylsulfinyl phenyl)-5-(4-pyridyl) 1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1,1'-biphenyl)-4-yl) methyl)-1H-1-benzazepin-3-yl)-, (R)-); EP1572 (Aib-DTrp-DgTrp-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; piperine; hemin; brazilin; z-VAD-FMK (Benzyloxycarbonyl-Val-Ala-Asp(OMe)-fluoromethylketone); z-LEHD-FMK (SEQ ID NO: 42) (benzyloxycarbonyl-Leu-Glu(OMe)-His-Asp(OMe)-fluoromethylketone); B-D-FMK (boc-aspartyl(Ome)-fluoromethylketone); Ac-LEHD-CHO (SEQ ID NO: 43) (N-acetyl-Leu-Glu-His-Asp-CHO); Ac-IETD-CHO (SEQ ID NO: 44) (N-acetyl-Ile-Glu-Thr-Asp-CHO); z-IETD-FMK (SEQ ID NO: 45) (benzyloxycarbonyl-Ile-Glu(OMe)-Thr-Asp(OMe)-fluoromethylketone); FAM-LEHD-FMK (SEQ ID NO: 46) (benzyloxycarbonyl Leu-Glu-His-Asp-fluoromethyl ketone); FAM-LETD-FMK (SEQ ID NO: 47) (benzyloxycarbonyl LeuGlu-Thr-Asp-fluoromethyl ketone); Q-VD-OPH (Quinoline-Val-Asp-CH2-O-Ph); XIAP; cIAP1; cIAP-2; ML-IAP; ILP-2; NAIP; Survivin; Bruce; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-[(phenylmethoxy)carbonyl]-L-leucyl-N-[(1S)-1-formyl-3-methylbutyl]-L-leucinamide); MYODUR; BN 82270 (Ipsen); BN 2204 (Ipsen); AHLi-11 (Quark Pharmaceuticals), an mdm2 protein, pifithrin-a (1-(4-Methylphenyl)-2-(4,5,6,7-tetrahydro-2-imino-3(2H)-benzothiazolyl)ethanone); trans-stilbene; cisstilbene; resveratrol; piceatannol; rhapontin; deoxyrhapontin; butein; chalcon; isoliquirtigen; butein; 4,2',4'-trihydroxychalcone; 3,4,2',4',6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.H2O); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperazinyl) methyl)-3,4-dihydro-2,5,7,8-tetramethyl-2H-1-benzopyran-6-ol.2HCl); β-1'-5-methyl-nicotinamide-2'-deoxyribose; (3-D-1'-5-methyl-nico-tinamide-2'-deoxyribofuranoside; β-1'-4,5-dimethyl-nicotinamide-2'-deoxyribose; β-D-1'-4,5-dimethyl-nicotinamide-2'-deoxyribofuranoside; 1-Naphthyl PP1 (1-(1,1-Dimethylethyl)-3-(1-naphthalenyl)-1H-pyrazolo[3, 4-d]pyrimidin-4-amine); Lavendustin A (5-[[(2,5-Dihydroxyphenyl)methyl][(2-hydroxyphenyl)methyl] amino]-2-hydroxybenzoic acid); MNS (3,4-Methylenedioxy-b-nitrostyrene); PP1 (1-(1,1-Dimethylethyl)-1-(4-methylphenyl)-1H-pyrazolo[3, 4-d]pyrimidin-4-amine); PP2 (3-(4-chlorophenyl) 1-(1,1-dimethylethyl)-1H-pyrazolo[3,4-d] pyrimidin-4-amine); KX-004 (Kinex); KX-005 (Kinex); KX-136 (Kinex); KX-174 (Kinex); KX-141 (Kinex); KX2-328 (Kinex); KX-306 (Kinex); KX-329 (Kinex); KX2-391 (Kinex); KX2-377 (Kinex); ZD4190 (Astra Zeneca; N-(4-bromo-2-fluorophenyl)-6-methoxy-7-(2-(1H-1,2,3-triazol-1-yl)ethoxy)quinazolin-4-amine); AP22408 (Ariad Pharmaceuticals); AP23236 (Ariad Pharmaceuticals); AP23451 (Ariad Pharmaceuticals); AP23464 (Ariad Pharmaceuticals); AZD0530 (Astra Zeneca); AZM475271 (M475271; Astra Zeneca); Dasatinib (N-(2-chloro-6-methylphenyl)-2-(6-(4-(2-hydroxyethyl)-piperazin-1-yl)-2-methylpyrimidin-4-ylamino) thiazole-5-carboxamide); GN963 (trans-4-(6,7-dimethoxyquinoxalin-2ylamino)cyclohexanol sulfate); Bosutinib (4-((2,4-dichloro-5-methoxyphenyl)amino)-6-methoxy-7-(3-(4-methyl-1-piperazinyl)propoxy)-3-quinolinecarbonitrile); or combinations thereof.

Miscellaneous Uses

In some embodiments, a selective transport molecule wherein the cargo moiety is an imaging agent and gadolinium is used to image metastases. In some embodiments, a selective transport molecule wherein the cargo moiety is an imaging agent and gadolinium is used in longitudinal experiments to determine whether inflammation comes before overt metastasis or shortly thereafter (FIG. 40). In some embodiments, a selective transport molecule wherein the cargo moiety is an imaging agent and gadolinium is used to image a disorder where MMP's play an important role and where visualizing MMP's and inflammation is useful for improving understanding of the disease process (e.g., bowel disease, rheumatoid arthritis, or multiple sclerosis). See Example 40 for a detailed analysis of the effects of conjugating a selective transport molecule to a dendrimeric nanoparticle, wherein the nanoparticle is also conjugated to gadolinium.

In some embodiments, a selective transport molecule conjugated to a dendrimeric nanoparticle is used to target tumor associated macrophages. In some embodiments, a selective transport molecule conjugated to a dendrimeric nanoparticle, wherein the nanoparticle further comprises Ricin A, is used to poison subcutaneous macrophages.

Pharmaceutical Compositions

Disclosed herein, in certain embodiments, are pharmaceutical compositions comprising a selective transport molecule disclosed herein. Pharmaceutical compositions herein are formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

In certain embodiments, a pharmaceutical composition disclosed herein further comprises a pharmaceutically acceptable diluent(s), excipient(s), or carrier(s). In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

In certain embodiments, a pharmaceutical composition disclosed herein is administered to a subject by any suitable administration route, including but not limited to, parenteral (intravenous, subcutaneous, intraperitoneal, intramuscular, intravascular, intrathecal, intravitreal, infusion, or local) administration.

Formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent is optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

In some embodiments, the pharmaceutical composition described herein is in unit dosage forms suitable for single administration of precise dosages. In unit dosage form, the formulation is divided into unit doses containing appropriate quantities of an active agent disclosed herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

EXAMPLES

Example 1: Peptide Synthesis

A number of peptides whose cell uptake could be modulated were synthesized. The following symbols, where used, are used with the indicated meanings: Fl=fluorescein; aca=ahx=X=aminocaproic acid linker (—HN—(CH$_2$)$_5$—CO—), C=L-cysteine, E=L-glutamate, R=L-arginine, D=L-aspartate, K=L-lysine, A=L-alanine, r=D-arginine, c=D-cysteine, e=D-glutamate, P=L-proline, L=L-leucine, G=glycine, V=valine, I=isoleucine, M=methionine, F=phenylalanine, Y=tyrosine, W=tryptophan, H=histidine, Q=glutamine, N=asparagine, S=serine, and T=threonine.

In sequences discussed below, lower case letters indicate the D isomer of the amino acid.

Peptides were synthesized on a peptide synthesizer (Pioneer Peptide Synthesis System by Applied Biosystems) using solid phase synthesis method and commercial available Fmoc amino acids, resins, and the other reagents. The peptides were cleaved with TFA/thioanisole/triisopropylsilane or TFA/thioanisole/triisopropylsilane/ethanedithiol.

Peptides were labeled with 5-(and-6)carboxyfluorescein succinimidyl ester on the amino group on the peptide or with 5-iodoacetamidofluorescein on the thiol group on the peptide.

The crude peptide was purified on HPLC and lyophilized overnight.

Each peptide composition was confirmed by mass spectrometry.

Synthesis of a Selective Transport Molecule (Hereinafter, Peptide 1)

Suc-$e_8$-(Aop)-PLGC9Me)AG-$r_9$-c-$NH_2$ was synthesized via standard Fmoc solid phase peptide synthesis. The N-terminal succinyl group was added to the peptide by reaction with succinic anhydride while still on resin. The peptide was cleaved from the resin in a standard cocktail (trifluoroacetic acid with 2% each of thioanisole, triisopropylsilane and ethanedithiol) overnight at room temperature. Most of the trifluoroacetic acid was remove by rotary evaporator, 50% hexanes in diethyl ether was added and the peptide was collected by centrifugation. The collected solid was washed with 50% hexanes in ether three times and vacuum dried overnight. The peptide was purified on HPLC using 15%-30% acetonitrile in water and 0.05% TFA, giving a 30% yield from the crude peptide. The correct purified product was confirmed by electrospray mass spectroscopy: calculated 3271.5 Da, found 3271.8 Da.

Synthesis of Peptide-Labeled Dendrimer 2

25 mg of peptide 1 was dissolved in 2 mL DMSO under N2 and was reacted with 2.3 mg 2-nitro-4-sulfophenyl 6-maleimidohexanoate sodium salt and 20 μL, N-methylmorpholine. After stirring at room temperature for three hours, LC-MS analysis of the reaction mixture indicated over 90% completion. The reaction mixture was cooled to 0°, 150 mg PAMAM dendrimer and 2 mL 1 M Hepes buffer (pH 7.8) were added and stirred at 5° for 2 days (hereinafter, reaction mixture 2).

Synthesis of Cy5- and Peptide-Labeled Dendrimer 3.

1.2 mg Cy5 mono(N-hydroxysuccinimide) was added to reaction mixture 2 and stirred at 5° overnight (hereinafter, reaction mixture 3).

Synthesis of Capped Cy5- and Peptide-Labeled Dendrimer 4.

66 mg of $MeO(CH_2CH_2O)_3CH_2CH_2CO$—(N-hydroxysuccinimide)ester was added to reaction mixture 3 at 5° and stirred at that temperature for 3 days. The crude product was diluted with 10 mL of water, and low molecular weight contaminants were removed by filtration 8 times through a membrane with a 10 kDa cutoff. HPLC using a size-exclusion column indicated 99% purity, 72% yield. An average of 3 fluorophores per dendrimer was determined by dissolving a known weight of purified final product in water and measuring Cy5 absorbance at 650 nm, assuming an extinction coefficient of $250,000 M^{-1} cm^{-1}$. Static multiangle light-scattering at 785 nm indicated an apparent molecule weight of 72.9 kDa. Dynamic light scattering at 785 nm indicated a hydrodynamic radius of 4.6 nm.

Synthesis of DOTA-, Cy5- and Peptide-Labeled Dendrimer 5

30 equivalents of DOTA mono-N-hydroxysuccinimide ester in HEPES buffer were reacted with reaction mixture 3 and stirred at 5° overnight (hereinafter, reaction mixture 5).

Synthesis of Capped DOTA-, Cy5- and Peptide-Labeled Dendrimer 6.

Reaction mixture 5 was reacted with 950 equivalents mPEG4 NHS and stirred at 5° for three days. The crude product was purified as described for capped Cy5- and peptide-labeled dendrimer 4, then lyophilized. The yield was 78%.

Gd Loading of Capped DOTA-, Cy5- and Peptide-Labeled Dendrimer 6

5 mg of capped DOTA-, Cy5- and peptide-labeled dendrimer 6 was dissolved in 1 mL 0.5M ammonium acetate and 1 mL water. The reaction mixture was mixed with 100 μL 0.5 $GdCl_3$ and stirred at room temperature for 3 days shielded from light. Small molecules were eliminated by 5 aqueous washes. Excess water was removed by centrifugation through a membrane filter with a 10 kDa cutoff. Finally, the Gd loaded product 7 was lyophilized overnight to give a blue fluffy solid. The pure product was weighed and redissolved in water to give a 200 uM solution. A measured small aliquot was mixed with 0.5 mL concentrated nitric acid for 2 hours. Gd quantitation was determined by inductively coupled plasma mass spectroscopy, which indicated an average of 15 Gd per dendrimer. The number of Cy5 labels per dendrimer was confirmed to be 3 based on 650 nm absorbance.

Example 2: Albumin Conjugated Selective Transport Molecules

Synthesis of Peptides

Peptides were synthesized by solid phase synthesis with free n-termini and c-terminal cysteine. Peptide sequence $e_9$-oPLGC(me)AG-$r_9$-c-$NH_2$ was synthesized for the cleavable peptide (o is 5-amino-3-oxapentanoyl linker and C(me) is S-methylcysteine) and $e_9$-(Peg2)2-$r_9$-c was synthesized for the uncleavable peptide. After cleavage and purification by HPLC the peptide was reacted in excess with Cy5-monomaleimide in DMF with NMM. After the reaction went to completion, the peptide was further reacted with maleimidopropionic acid-PFP ester under the same conditions as the previous reaction. Reactions were monitored by HPLC mass spectrometry and purified by HPLC. For DOTA labeled peptides the peptide was made by adding a (Peg4) to the n-terminus of the peptide and a k(Dota) between the arginine and the cysteine on the c-terminal end of the peptide during solid phase synthesis. The sequence for these two dual labeled peptides is Mal-Peg4-$e_9$oPLG(Cme)AG-$r_9$-k(DOTA)-c(Cy5) for the cleavable peptide and mal-Peg4-$e_9$-Peg4-$r_9$-k(DOTA)-c(Cy5) for the uncleavable peptide.

Reaction with Albumin and Enzyme Cleavage Assay

Maleimide peptides were initially reacted with mouse serum albumin (Sigma) at 40 mg/mL or fresh frozen mouse plasma for one hour. Samples were run on a tricine buffered 10-20% polyacrylamide gel and imaged for Cy5 fluorescence on a UVP gel imager. For the enzyme cleavage assay, Cy5-monomalaimide and the cleavable maleimide peptides were reacted as 2 nmol with mouse serum albumin at 40 mg/mL in 25 mM hepes buffer. The stock was then diluted 1:10 to 5 mM with 50 nM of recombinant MMP-9 (EMD Biosciences) and digested for 20 minutes and 4 hours then run on a tricine gel and imaged by Cy5.

Animals

Figure 8:
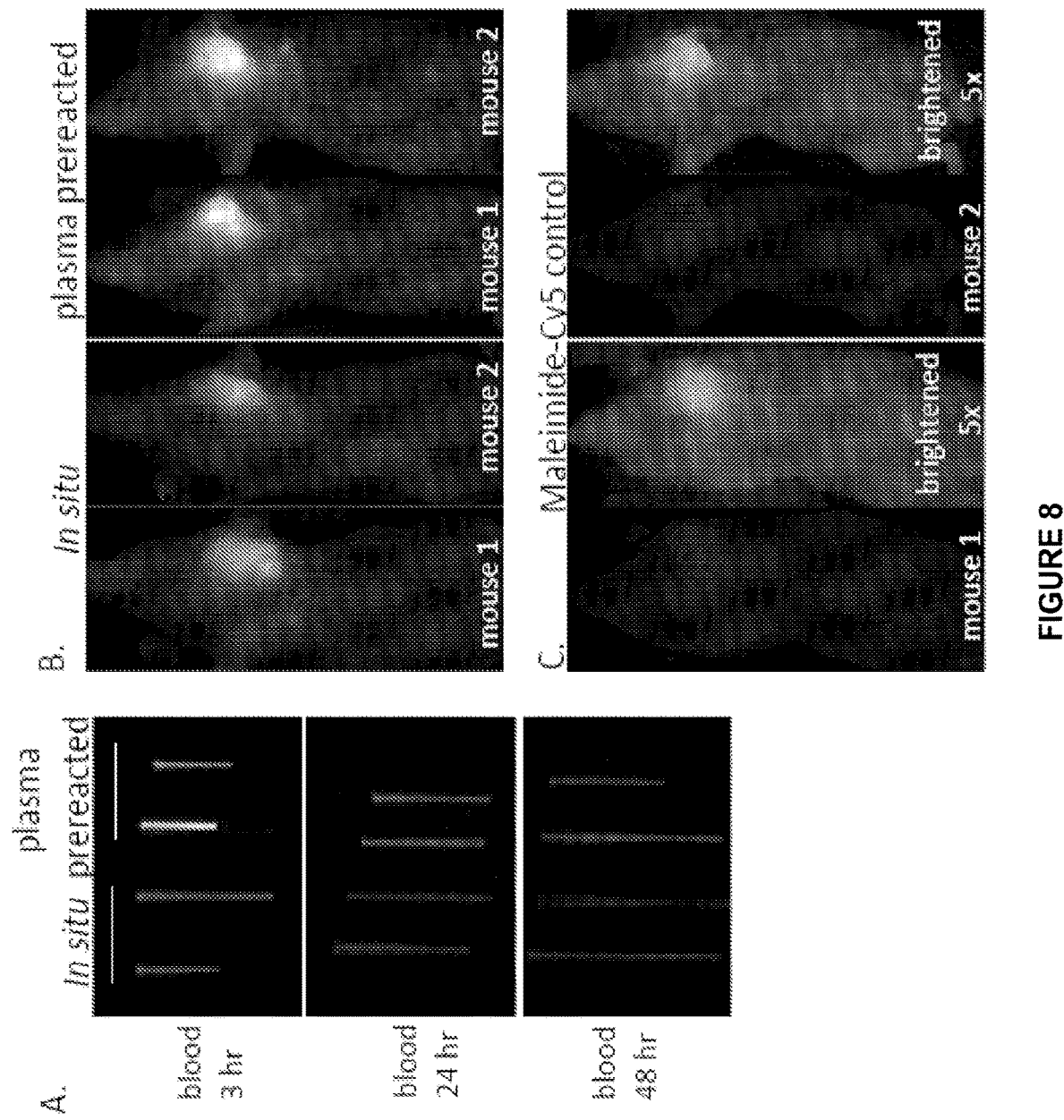
FIG. 8. Pre-reacting selective transport molecule to plasma significantly increases the half-life and the tumor uptake. (A) Pre-reacting the selective transport molecule with fresh frozen plasma for 30 minutes before injection into 4T1.2 tumor bearing mice significantly increased the blood levels at 3, 24 and 48 hours after injection compared to unreacted peptide. These fluorescent images show capillary tubes of blood drawn at these different time points after IV injection if two mice each with unreacted albumin reactive selective transport molecule and plasma pre-reacted selective transport molecule. (B) Fluorescence images of 4T1.2 tumors 48 hours after injection with unreacted and pre-reacted albumin reactive selective transport molecules. There were two mice for each treatment injected at the same time. (C) Cy5-maleimide control leads to less accumulation in the tumor than the selective transport molecule peptides. Images were brightened 5x.
Figure 9:
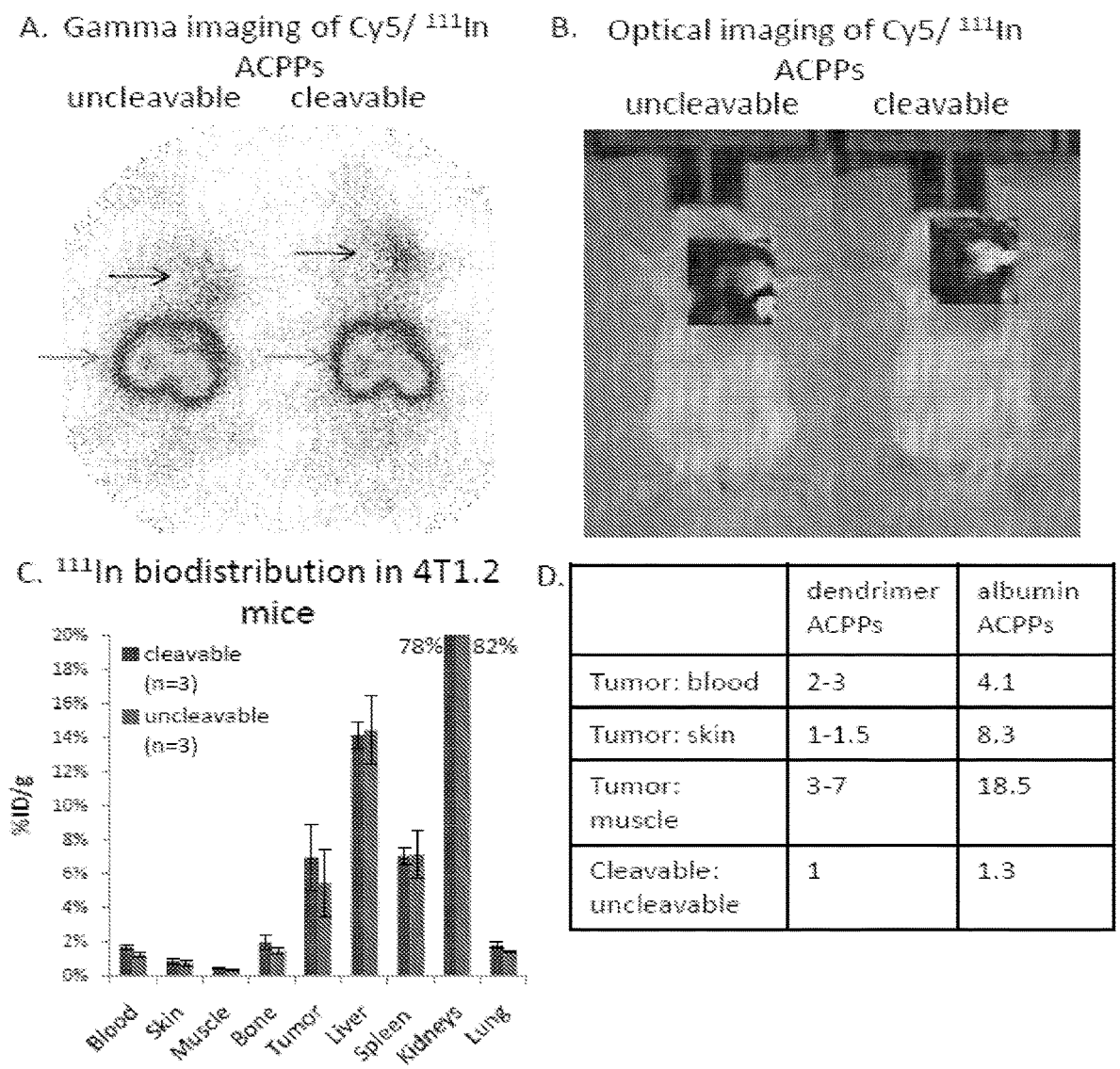
FIG. 9. Clinical contrast can be attained with $^{111}$In labeled albumin reactive selective transport molecules. (A) Planar gamma images of mice injected with 0.3 nmols of cleavable and uncleavable albumin reactive selective transport molecules. Black arrows show that the tumor develops nice contrast 48 hours after injection. The blue arrows show that when the peptide was cleared through the kidneys much of the peptide was retained and cleared slowly. (B) Fluorescence images of tumor from $^{111}$In and Cy5 dual labeled albumin binding peptides imaged 48 hours after injection. Tumor fluorescence was able to be detected with a 10 fold lower dose than the standard optical dose. (C) Biodistribution in % Dig of multiple tissues showing that there was a slight difference between the cleavable and uncleavable peptide. There was only greater peptide distribution found in liver and kidney. (D) A table showing that there was greater tissue contrast with the albumin reactive selective transport molecules compared to the dendrimer based selective transport molecules tested in previous studies.

Nude mice were injected with $2X^{06}$HT1080 human fibrosarcoma cells in the left #2 mammary fat pad. Experiments were performed 5-7 days post injection. Polyoma Middle T mice (PyMT) were provided by Lesley Ellies and they were injected with peptide IV between 9-12 wks of age when medium to large sized tumors were present in each mammary fat pad. One million mouse mammary adenocarcinoma 4T1.2 cells (from Robyn Anderson, University of Melbourne) were injected into the left mammary fat pad of nude mice (FIGS. 4 and 7) and Balb/c mice (FIGS. 8 and 9) and 5-20 days later were injected with peptide and imaged.

Optical Imaging and Tissue Processing

When tumors were of sufficient size 5-20 days after injection of tumor cells the peptide was injected IV and imaged on the Maestro small animal imager (CRI). Animals were sacrificed by overdose with Isoflurane and dissected. To examine lung metastases, the lungs were inflated with OCT cryoprotectant and imaged on the small animal imager. Blood measurements were taken by bleeding the tail vein at a specified time point and collected in a capillary tube. The tubes were then imaged for presence of the Cy5 fluorescent peptide using the small animal imager. For processing of tissues for gels, 30 mg of tissue was homogenized in a 1% SDS Tris buffer then heated at 80° C. for 10 min and centrifuged. The supernatant was then diluted 1:10 and run on a tricine gel and imaged by fluorescence.

Fluorescence Histology

Tumors and lung from each mouse were frozen in cryo molds in OCT media and then cryosectioned at 10 μm slices. Tissues were then imaged by Cy5 fluorescence on a fluorescence dissecting microscope. The same section or serial sections were then stained with hematoxylin and eosin (H&E).

$^{111}$In Radioisotope Experiments 3.6 nmols of cleavable and uncleavable maleimide selective transport molecules were reacted with 1.2 mCi$^{111}$ in for 1 hour at 40° C. in 10 mM NaOAc pH 7.0. After reaction, 100 nmol of cold InCl$_3$ was spiked in and incubated for another hour to be chelated by unreacted DOTA. After incubation the peptide stock reactions were centrifuged through a 5 kDa amicon column to wash out unreacted cold and hot In. A gel of the reaction mixture was run and exposed using a phosphor imager to verify that all the 111 In was reacted with the peptide. After column filtration one third of the radioactivity was recovered. Three mice were then injected with 0.3 nmol of peptide with about 50μ·Ci IV. The mice were then imaged by planar gamma imaging and optical imaging (Optix, GE healthcare) for up to 48 hours and were then euthanized. Mouse tissues harvested, placed into scintillation vials, weighed and counted to determine the % ID/g. For comparison, the ratios of % ID/g was calculated and compared to the range from previous comparable experiments conducted with dendrimers done by collaborator Edmund Wong.

Synthesis of Albumin Reactive Maleimide Selective Transport Molecules

Synthesis of albumin reactive selective transport molecules requires a one step reaction and purification beyond standard free peptide synthesis. Peptide is synthesized as NH$_2$-e$_9$-cleavagesite-r$_9$-c(Cy5)-NH$_2$ as opposed to a succinyl capped e$_8$ N-terminus. Next a heterobifunctional linker can be reacted to the free amine on the N-terminus in the form of maleimide and NHS ester. The linker could contain a short hydrophilic peg chain or a more hydrophobic carbon chain. Upon initial synthesis a maleimidopropionic acid PFP ester, a maleimide Peg8 succinimidyl ester, and maleimide Peg24 succinimidyl ester were all made. The PFP ester had a significantly faster reaction time and higher yield compared to the classic Peg succinimidyl esters. It was difficult to purify the Peg8 and Peg24 and the reaction was inefficient so we focused on the propionic acid linker. Schematic and peptide structure are show in FIGS. 1A and 1B resulting in a final sequence of, mal-e$_9$-oPLG(Cme)AG-r$_9$-c(cy5). The peptide was made with the cleavage site of oPLG(Cme)AG because it is more hydrophilic and has worked better on carriers than xPLGLAG.53.

Figure 1:
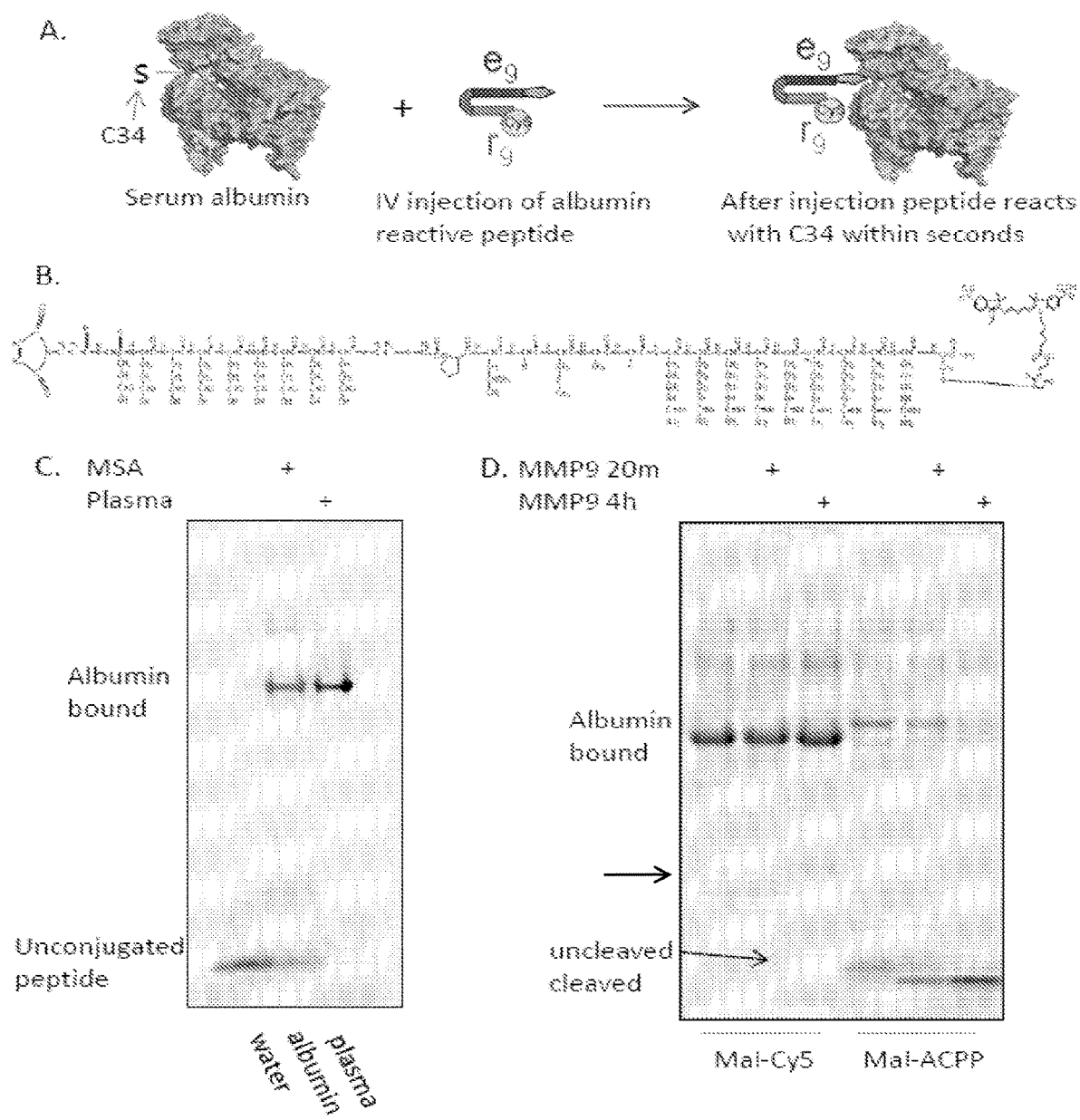
FIG. 1. Albumin reactive selective transport molecules create a robust reaction with native albumin and the selective transport molecule can be cleaved off by MMP9. (A) Schematic of free peptide selective transport molecules that have a thiol reactive group that can react with C34 of albumin in mice or humans. (B) Chemical structure of the albumin reactive selective transport molecules which have a c-terminal maleimide group followed by $e_9$-(MMP cleavage substrate)-$r_9$c(payload) sequence, in this case oPLG(Cme)AG (SEQ ID NO: 3) is the substrate and Cy5 is the far-red tag. (C) The albumin reactive peptide reacts to both aqueous purified mouse serum albumin and fresh frozen mouse plasma in one hour. The plasma reacted to near completion in a 15:1 ratio of albumin to peptide (50 uL of 40 mg/mL MSA with 2 nmol of peptide). (D) Reacted selective transport molecule is cleaved off of the albumin to near completion in less than 4 hours. The gel shows albumin bound, uncleaved peptide, and cleaved peptide when it was treated with 50 nM MMP-9 enzyme for 20 minutes and 4 hours.

Validation of Maleimide Selective Transport Molecules and Enzyme Cleavage in Test Tube Malemide selective transport molecule was reacted mouse serum albumin and plasma in aqueous conditions to determine that peptide reacts with albumin in a test tube. These data show that within an hour of mixing the peptide with the albumin most of the peptide reacted with MSA or plasma albumin (FIG. 1C), based upon polyacrylamide gel electrophoresis (PAGE). Plasma seemed to give somewhat more complete reaction. After prereaction of maleimide Cy5 and maleimide selective transport molecule to albumin the conjugates were treated with MMP-9 to verify that the r9-c(Cy5) peptide was efficiently cleaved off of the albumin suggesting that not only does the selective transport molecule react with albumin in physiological conditions it can be cleaved by MMPs (FIG. 1D).

Injection of Maleimide-Selective Transport Molecule into Tumor Bearing Mice Reveals Superior Contrast than Uncleavable Peptide and Free Peptide in HT1080 Mice.

Figure 2:
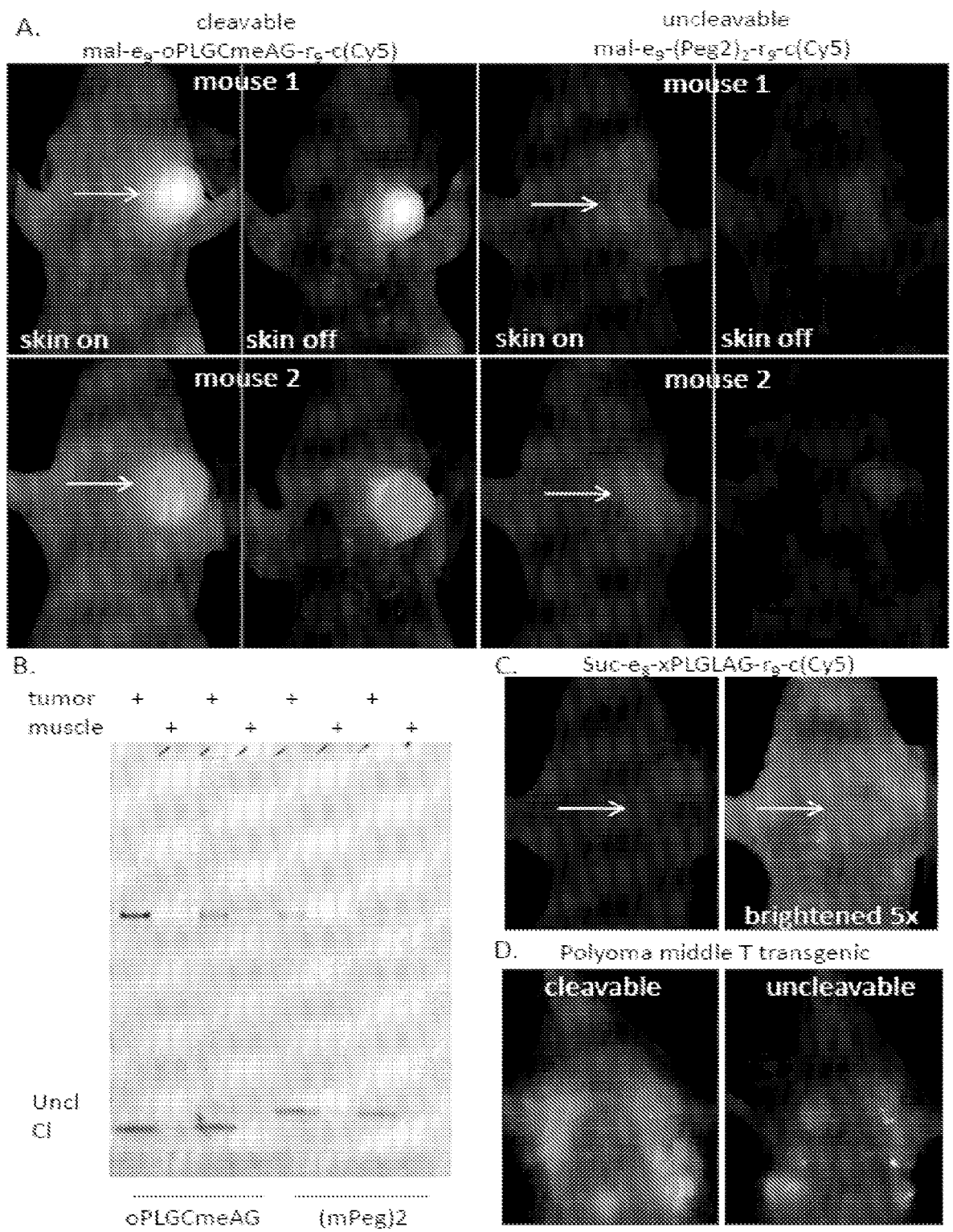
FIG. 2. Albumin reactive peptide creates significant contrast in HT1080 tumor bearing mice and in polyoma tumors. (A) HT1080 mice were injected IV with 3 nmols of albumin reactive peptide on the same day with cleavable and uncleavable selective transport molecules. Mice were imaged and sacrificed 24 hours later. Fluorescence images of 2 mice per peptide with the skin on and skin off are shown with arrows pointing to the tumors. (B) Tumors and muscles were homogenized from the above mice and supernatant was run on a gel revealing that there was both cleaved and uncleaved albumin bound peptide in the tumor. (C) When HT1080 mice were injected with the same dose of free peptide and imaged at 24 hours the uptake and contrast was negligible compared to the albumin reactive peptide (white arrow points to tumor). (D) The albumin reactive peptide can also be injected into polyoma middle T spontaneous tumors and there is difference between the cleavable and uncleavable peptides.

With the in vitro mechanism validated, the peptides were injected into HT1080 human fibrosarcoma tumor bearing mice to determine whether there was superior tumor targeting compared with previous versions of selective transport molecule. Because the maleimide peptides are analogous in structure to the free selective transport molecule, a dose of 10 nmols was used for initial experiments. This peptide was found to have a much longer half-life and to have much greater uptake in animals compared to free peptide so the dose was decreased to 3 nmoles (data not shown). Two mice each were injected with the cleavable maleimide peptide and two mice were injected with uncleavable selective transport molecule Mal-e$_9$-(Peg2)2-r$_9$-c(Cy5). The mice were imaged for up to 24 hours, and images of the two mice for each peptide with skin on and after the skin was removed are shown in FIG. 2A. The uptake was much greater with the cleavable peptide compared to the uncleavable peptide. The tumors and muscle were then homogenized and their supernatants were run on gels to determine if the peptide was cleaved, uncleaved, or uncleaved bound to albumin (FIG. 2.B). As expected there was cleaved and albumin bound peptide in the tumors of mice injected with the cleavable peptide and there was uncleaved free peptide and albumin bound peptide in the mice injected with the uncleavable peptide. There was no detectable peptide in the muscle. This level of uptake as an albumin reacting free peptide at a low dose was significantly greater than the free peptide. When an animal was injected with 3 nmols of Suc-e$_8$-xPLGLAG-r$_9$-c(Cy5) the tumor uptake was difficult to detect 24 hours after injection (FIG. 2C). When two PyMT transgenic mice were injected with both the cleavable and uncleavable peptide the uptake was significant and differential though this was only in two mice since availability of the PyMT mice is limited (FIG. 2D).

The HT1080 tumors were collected from the mice that were injected with the cleavable and uncleavable maleimide peptides and processed for fluorescence histology. Frozen sections were imaged for Cy5 fluorescence and serial sections were H&E stained to get a better sense of the differential nature of uptake at the microscopic level. As seen before with the HT1080 tumors there was very little uptake in the avascular core of the tumor, but rather the peptide was taken up around the periphery at the tumor stroma boundary with a little bit of enhanced uptake deeper into the tissues (FIG. 3A). This distribution of uptake is very similar to that which has been seen with the free peptides. The uncleavable peptide did not have nearly as much uptake at the edges or deeper inside the tumor parenchyma as was seen with the cleavable peptide (FIG. 3B).

In Metastatic Syngeneic Mammary Adenocarcinoma Tumors there was Differential Uptake in Large and Small Tumors with a Similar Distribution as in HT1080s.

Figure 4:
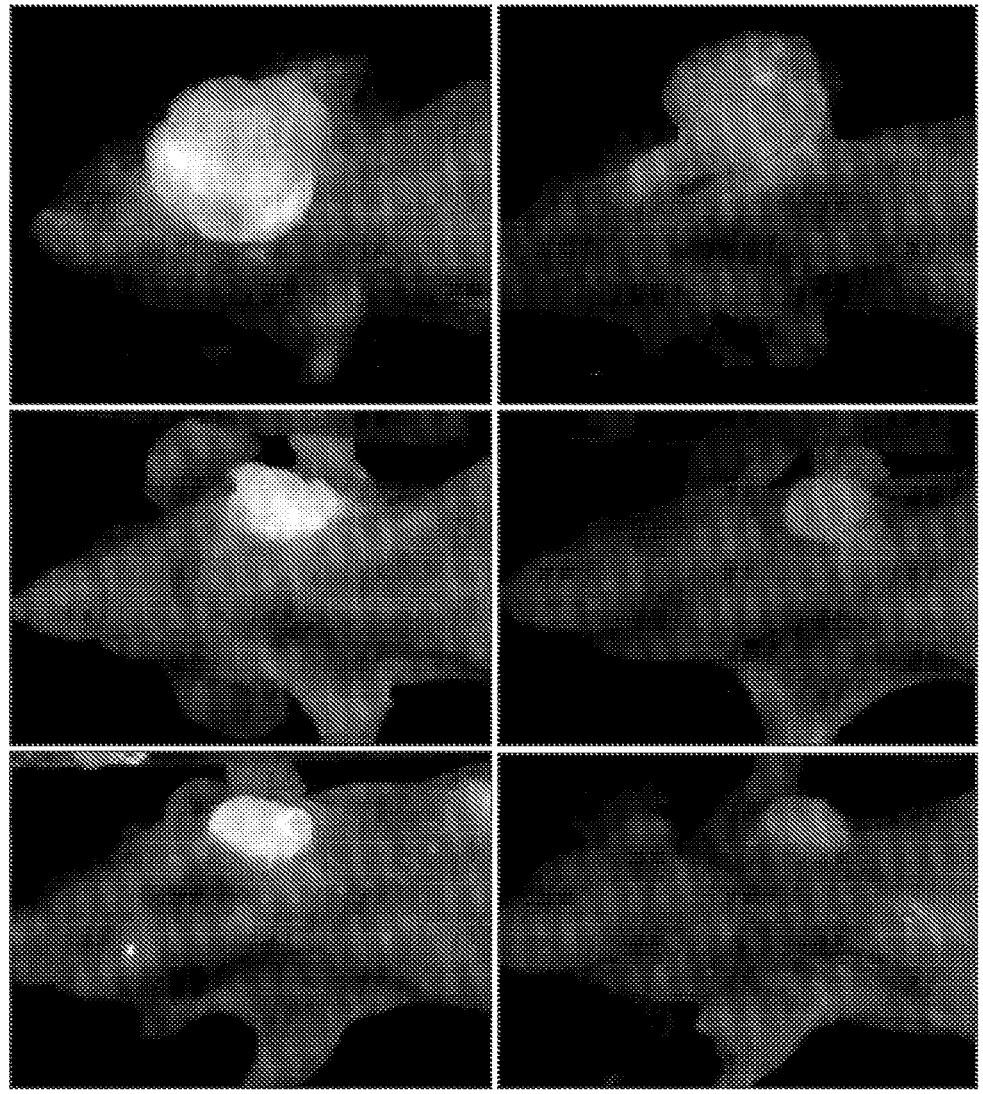
FIG. 4. Albumin reactive selective transport molecules yield significant contrast in 4T1.2 mouse mammary adenocarcinoma grafts. Six mice were injected with 3 nmoles of albumin reacting selective transport molecule. Three mice with cleavable peptide and three with uncleavable peptide. Mice were sacrificed after 24 hours, skin was removed, and the mice were imaged. Once set of mice were allowed to progress to very large tumors in order to try to detect metastases in the lungs.
Figure 5:
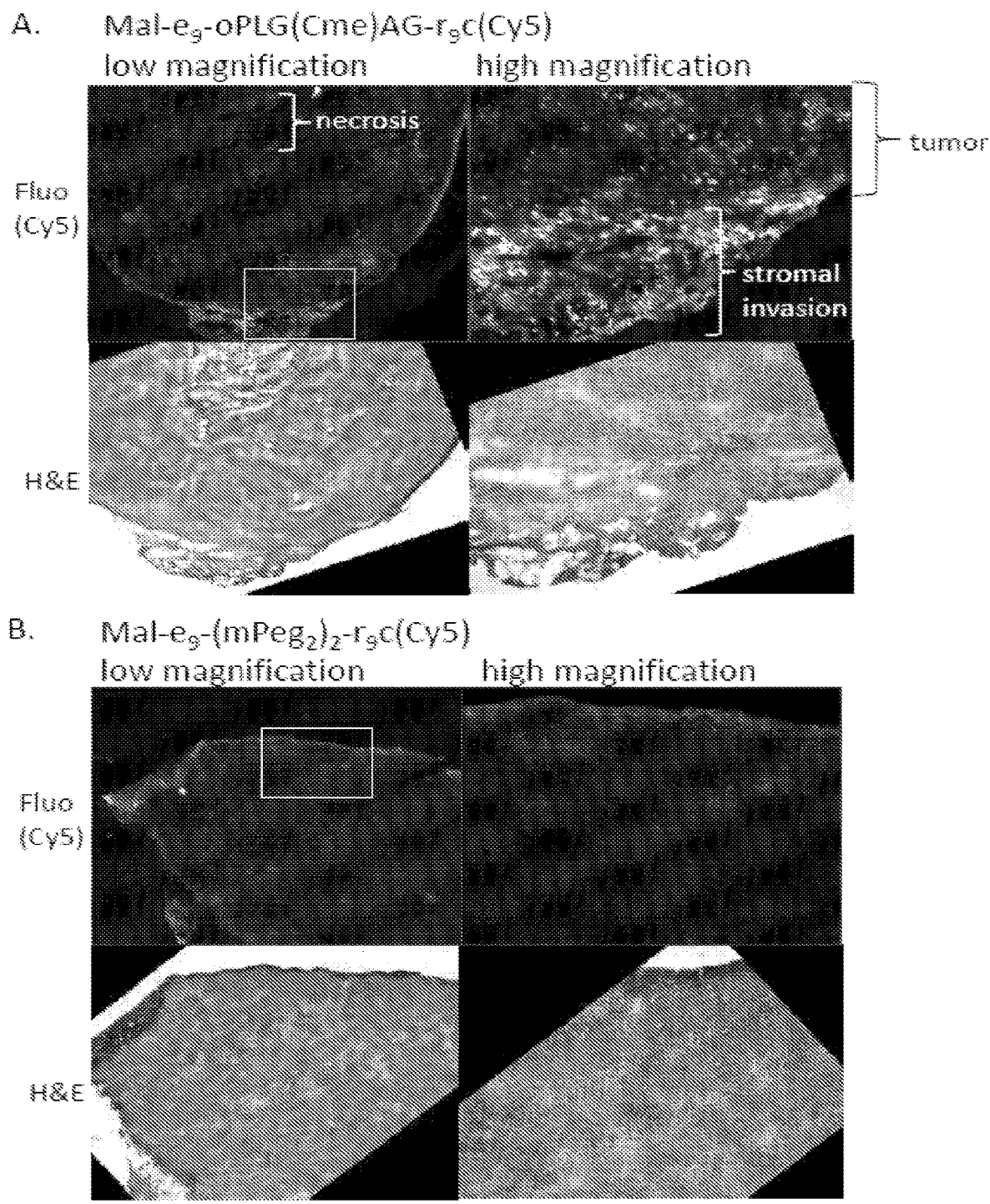
FIG. 5. Tumor histology of albumin reactive selective transport molecules in 4T1.2 mice. (A) Shows low and high magnification images of fluorescence histology and H&E of 4T1.2 tumor which reveal significant uptake in the tumor parenchyma and even greater in areas of stromal invasion of the cleavable albumin reactive peptide. Areas of necrosis did not have significant uptake as seen with free peptide injections in previous work. (B) Shows fluorescence and H&E of tumor from a mouse injected with uncleavable peptide with less uptake.

Albumin reactive peptides were then injected into the 4T1.2 syngeneic mammary adenocarcinoma tumor model. This tumor model is advantageous for a number of reasons including that fact that the 4T1.2 cells naturally metastasize to distant tissues including the lung and the bone, which is potentially useful for determining how well Selective transport molecules target metastases. Three mice mere initially injected with 3 nmols of the cleavable and three mice were injected with uncleavable peptide. Experiments were carried out on one set of mice when the tumors were much larger so as to determine if the contrast remains with large tumors and if we could detect metastases in the lungs or elsewhere. After 24 hours the mice were sacrificed and there was an obvious difference between the cleavable and uncleavable tumor fluorescence (FIG. 4). The tumors were frozen sectioned as done with the HT1080 tumors in FIG. 3 to reveal that the differences were even greater in this 4T1.2 model. In the mice injected with the cleavable peptide there was bright fluorescence uptake throughout the tumor unlike with the HT1080s and even brighter uptake in areas of stromal invasion (FIG. 5A). Unlike with the free peptides there was much less uptake in necrotic tumor cells as labeled in the lower magnification image this is different than the classic free peptides. In the tumors with the uncleavable peptide there was diffuse uptake that was lower than and not as distinct as with the cleavable peptide (7.5B).

Figure 3:
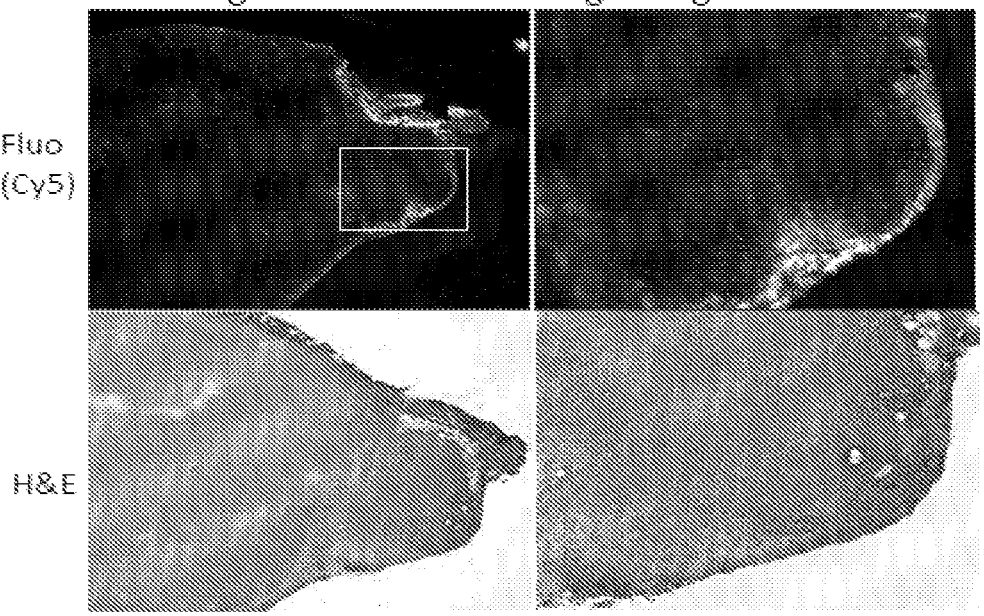
FIG. 3. Histology of HT1080 tumors shows that most of the uptake was at the tumor stroma border. (A) Both low and high magnification of fluorescence histology and H&E stains of HT1080 tumors which reveal the significant uptake is near the capsule of the tumor at the tumor stroma boundary with the cleavable peptide. (B) The uncleavable peptide had less uptake compared to the cleavable tumors.
Figure 3:
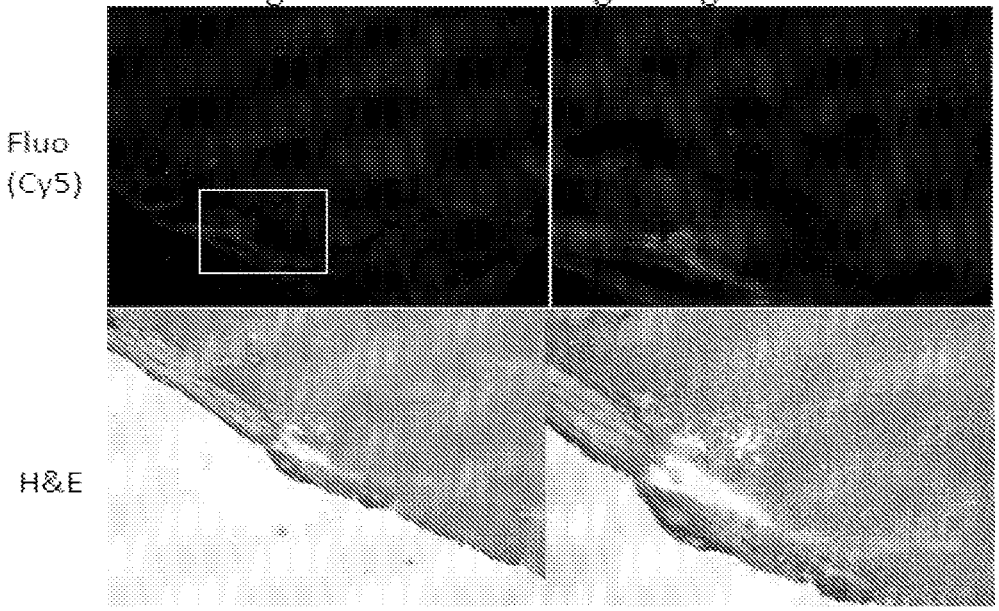
Figure 6:
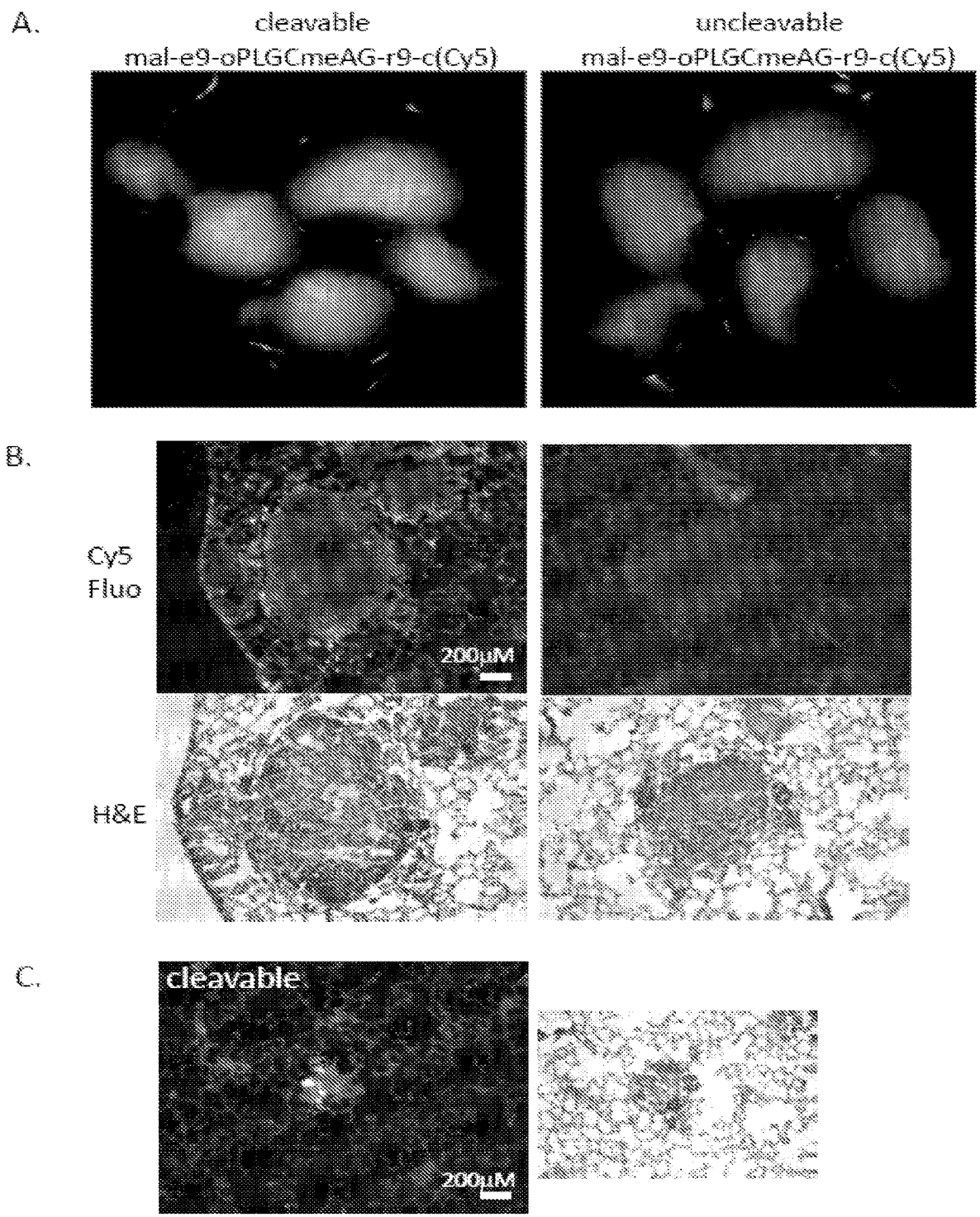
FIG. 6. Albumin reactive selective transport molecules are taken up by lung metastases in a specific way. (A) Gross images of lungs from mice with large 4T1.2 tumors showing brightly fluorescent speckles throughout the lungs. The signal is brighter in the speckles and parenchyma of mice injected with the cleavable peptide compared to the uncleavable peptide. (B) Fluorescence histology and H&E of the lungs confirm the presence of metastases. (C) Small metastases stained brightly with the cleavable selective transport molecule peptide.

The lungs were dissected from mice with the large tumors shown in FIG. 3. There seemed to be small metastases throughout the lungs as seen by fluorescence imaging of the lung lobes (FIG. 6A). The lungs were then frozen sectioned and imaged by fluorescence to detect the Cy5 peptide. This imaging revealed an increased uptake of selective transport molecule in metastases of mice injected with the cleavable peptide compared to the uncleavable peptide (FIG. 6B). The uptake was more at the edge of the metastasis and it did not seem to penetrated deep into the foci as it had with free peptides. However, when smaller micro metastases were identified there seemed to be greater selective transport molecule uptake, suggesting that perhaps the albumin peptides were better at labeling the exposed edges and smaller metastases than the dense core (FIG. 6C).

The lungs were dissected from mice with the large tumors shown in FIG. 3. There seemed to be small metastases throughout the lungs as seen by fluorescence imaging of the lung lobes (FIG. 6A). The lungs were then frozen sectioned and imaged by fluorescence to detect the Cy5 peptide. This imaging revealed an increased uptake of selective transport molecule in metastases of mice injected with the cleavable peptide compared to the uncleavable peptide (FIG. 6B). The uptake was more at the edge of the metastasis and it did not seem to penetrated deep into the foci as it had with free peptides. However, when smaller micro metastases were identified there seemed to be greater selective transport molecule uptake, suggesting that perhaps the albumin peptides were better at labeling the exposed edges and smaller metastases than the dense core (FIG. 6C).

Figure 7:
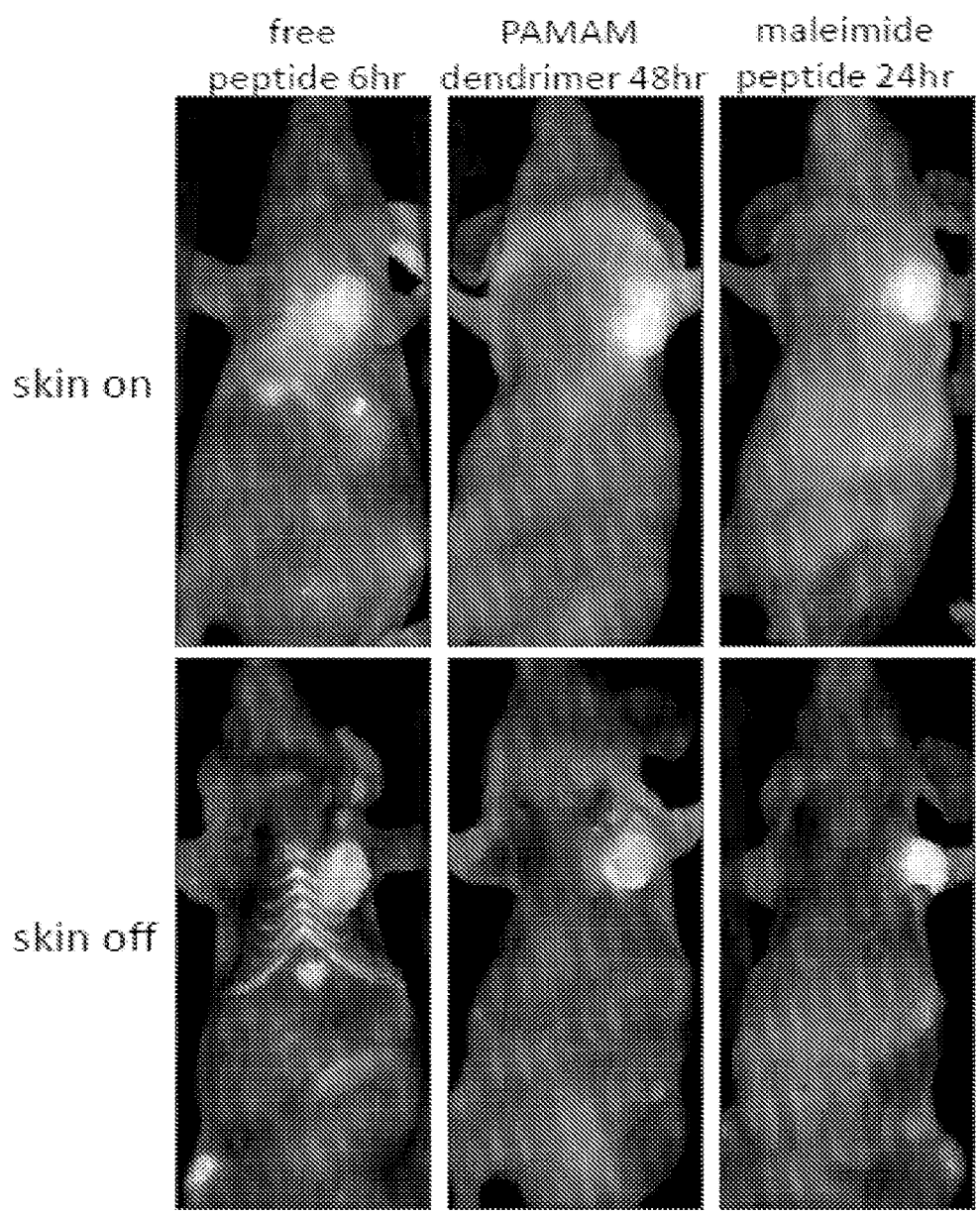
FIG. 7. Comparison of the three main types of selective transport molecules reveal that the albumin reactive selective transport molecules are comparable if not an improvement on other configurations. Three 4T1.2 tumor bearing mice shown here were used to test three different selective transport molecule designs to determine which provides the best tumor contrast and lower in specific uptake in background tissues. The left panels show the free peptide 6 hours after injection when it has optimal contrast, then the PAMAM dendrimers are shown after 48 hours in the middle, and the right panel shows the albumin reactive peptide 24 hours after injection.

Albumin Reactive Selective Transport Molecules are as Good if not Better in Creating Contrast in Tumors as the Other Selective Transport In order to determine whether the albumin reactive peptides were as good or better than previously described designs of selective transport molecules, a set of mice were tested side by side at their optimal times and doses. 4T1.2 cells were injected into nude mice and when the tumors were about 6 mm in size, animals were injected with the Suc-$e_8$-xPLGLAG-$r_9$-c(Cy5) free peptide (10 nmols), G5-PAMAM (selective transport molecule)6(Cy5)3 dendrimer (2 nmols), 53-, and Mal-$e_9$-oPLG(Cme)AG-$r_9$-c(Cy5) (3 nmols). The free peptide injected mouse was imaged and euthanized after 6 hours, the dendrimers at 48 hours, and the maleimide at 24 hours. Images with the skin on and the skin off for each mouse were scaled to maximum brightness as is shown in FIG. 7 revealing the relative contrast and background uptake in various tissues. These data reveal that both the albumin reactive and maleimide peptides work particularly well whereas the free peptide is good, but has significant uptake in other tissues.

Further Optimization of Maleimide Peptides and Distribution Characteristics

When looking at biodistribution of the maleimide peptides, it was revealed that most of the peptide went to the kidney after injecting, when injecting them as a free peptide for in situ reaction with plasma. Thinking that pre-reaction would increase the plasma half-life and possibly the tumor uptake, we initially tried pre-reacting with mouse serum albumin. Counter intuitively this was found to cause a shorter plasma half-life and lower tumor uptake. We hypothesized that commercial mouse serum albumin might contain oligomers as was evidenced by gel electrophoresis in some chemical state with regard to other molecules bound that it was being cleared more rapidly from the mouse blood. After observing that fresh frozen mouse plasma reacted with peptide faster than the mouse serum albumin did (FIG. 1C) we decided to inject peptide prereacted with fresh frozen plasma. Two mice were injected with each of the unreacted or plasma prereacted peptide and blood was drawn after 3, 24 and 48 hours. Surprisingly there was greater plasma level of peptide at all time points in the mice injected with the prereacted peptide than in mice injected with the maleimide (FIG. 8A). When the animals were imaged and sacrificed after 48 hours there was clearly a greater amount of uptake in the tumors of the prereacted mice (FIG. 8B). For this set of experiments we injected Cy5-monomaleimide as a control for fluorescent non-selective transport molecule albumin. Upon fluorescent imaging of the mice the tumors had significantly less fluorescence suggesting that the contrast was not due only to EPR effect but the presence of selective transport molecules (FIG. 8C).

Dota($^{111}$In) Selective Transport Molecule Peptides Become Clinically Relevant with Sufficient Tumor Targeted Biodistribution for Robust Contrast.

To determine if the level of contrast attained with the albumin reactive selective transport molecules was sufficient for clinical imaging, DOTA labeled maleimide peptides were synthesized so that the peptide could chelate $^{111}$In. Peptides contained both a Cy5 and DOTA to be able to do dual modality imaging. Peptide was labeled with $^{111}$In under aqueous conditions and 50 µCi of peptide was injected into each animal at a dose of 0.3 nmols not prereacted to plasma (10 times less peptide than used for optical imaging). Then mice were imaged with a planar gamma camera and an optical imager to detect both radioactivity and fluorescence at various time points up to 48 hours later. FIG. 9A is two mice injected with the cleavable and uncleavable peptide after 48 hrs. The black arrows point to the tumor, which showed up with notable contrast and the blue arrows point to the kidneys, the organ with the most amount of uptake. On optical imaging the only organ that was detectable was the tumor, the kidney and liver were not visible in the intact mouse because of the limit of penetration of the fluorescence (FIG. 9B). Biodistribution of excised tissues from the 3 mice per treatment is shown in FIG. 9C showing that there was up to 8% ID/g of the selective transport molecule delivered to the tumor with the cleavable peptide. Unexpectedly the uncleavable peptide was not statistically lower in uptake than the cleavable but there was a difference. To get a sense of how good the tumor contrast is compared to other selective transport molecule constructs tested in the past we calculated the contrast uptake rations of tumor compared to important nearby tissues for these albumin reactive Selective transport molecules and the PAMAM dendrimers. Tumor to blood, skin, and muscle ratios of the albumin reactive maleimide peptides is superior to all the dendrimers we have tested in the past via radiolabeling (FIG. 9D). However the cleavable to uncleavable contrast rations are not very impressive. Much of this could be due to the EPR effect for both the maleimide and dendrimer configurations.

Example 3: Dendrimer Conjugated Selective Transport Molecules

Podophyllotoxin Animal Experiments

A selective transport molecule-Podophyllotoxin (selective transport molecule-podo) conjugate by reacting podo-ss-pyridine with Suc-$e_8$-xPLGLAG-$r_9$-c, purified by HPLC and confirmed by mass spectrometry. The peptide was stored as a TFA salt and the yield was determined by mass. For animal experiments, athymic nude mice were injected with $1 \times 0^6$HT1080 human fibrosarcoma cells in the mammary fat pad. After one week when tumors were 30-50 mm$^3$ mice were injected IP once every other day for a total of three times with 10 μmol/kg of either podophyllotoxin, selective transport molecule alone, or selective transport molecule-podo. There were 3 mice per treatment group that were weighed and had tumors measured regularly. The mice were euthanized after 10 days due to significant weight loss in the selective transport molecule and selective transport molecule-podo treatment groups.

Doxorubicin PAMAM Dendrimer Quality Control

Figure 11:
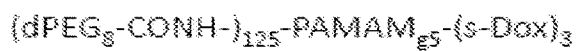
FIG. 11. Structure and quality control of doxorubicin conjugated dendrimers. (A) Structure of the four doxorubicin containing dendrimers that were screened for anti-tumor activity. The thioether is a stable thiol conjugate. The aromatic, urea, and Peg are different doxorubicin acid labile hydrazone linkers tested. (B) Gels of different dendrimers treated at pH 7.4 and pH 5 for 18 hours determine which linker is the most acid responsive. The thioether had nearly undetectable free doxorubicin contaminant and much was attached to the dendrimer. The aromatic and urea hydrazone linkers were not very acid responsive and there was a lot of free drug contaminant. The Peg linker had a much more favorable hydrolysis capacity.
Figure 11:
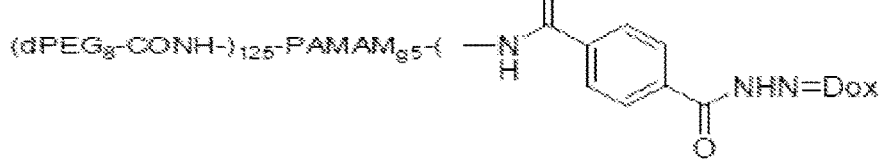
Figure 11:
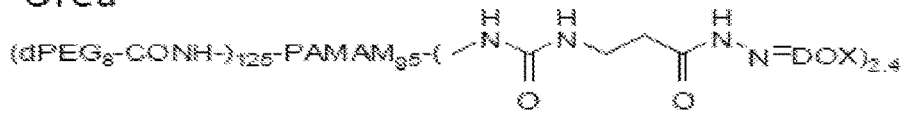
Figure 11:
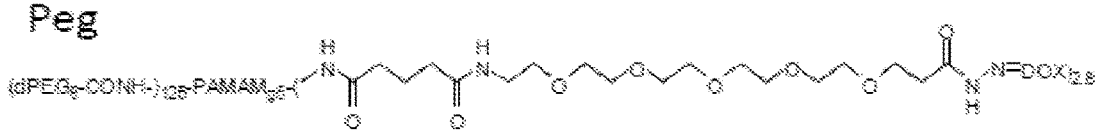
Figure 11:
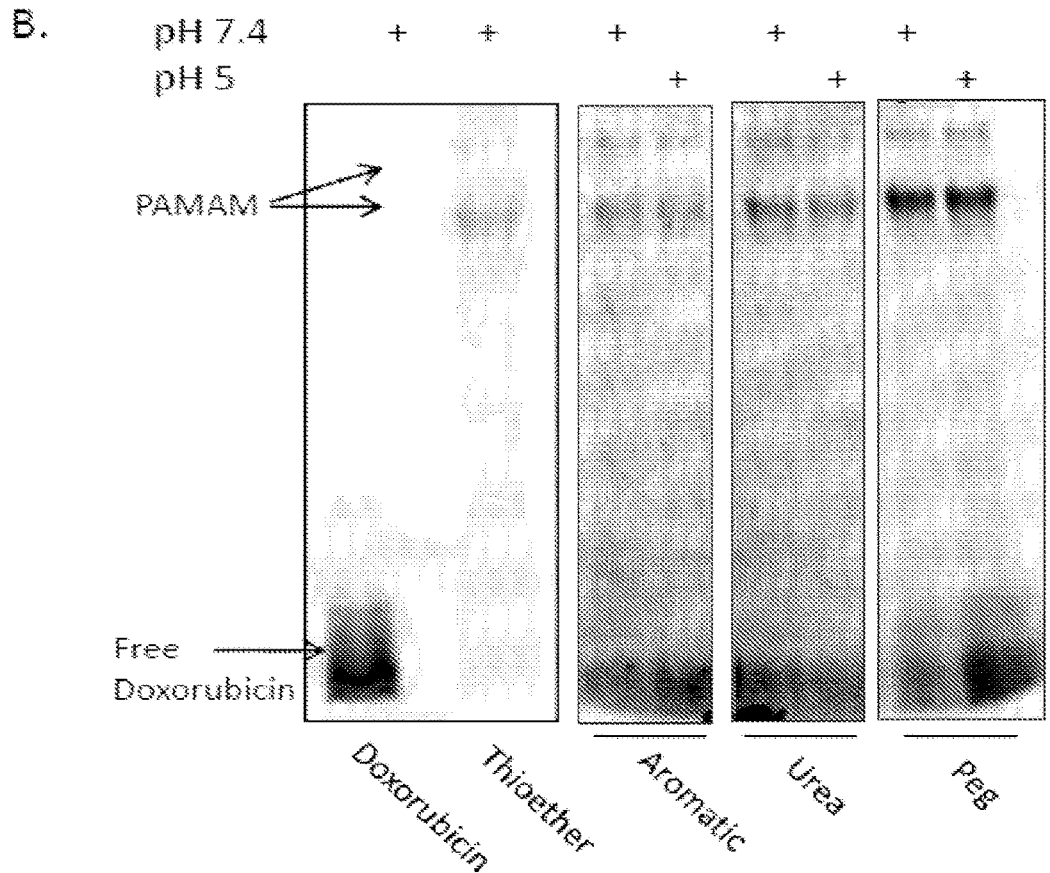
Figure 14:
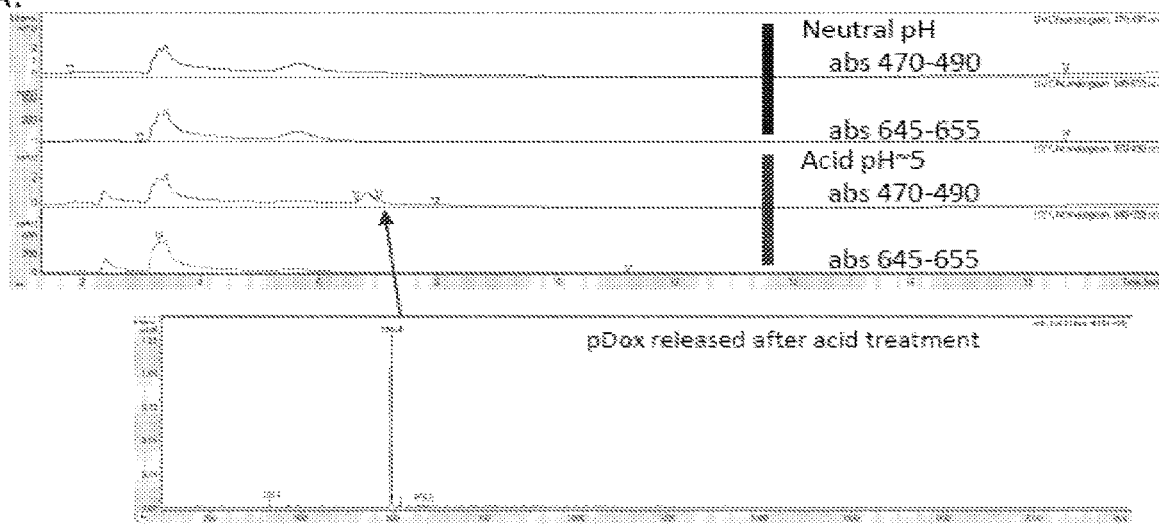
FIG. 14. Verification of pDox conjugated Cy5 Dendrimer. (A) HPLC traces of the pDox Cy5 PAMAM dendrimer treated in neutral pH or pH 5 overnight. Both the 470-490 nm and 645-655 nm absorbance traces are shown to assist in identification of pDox and Cy5 labeled dendrimers respectively. After incubation at pH 5 there was a new peak that arose in the 470-490 channel that had the exact mass for pDox. (B) Shows Cy5 absorbance and pDox fluorescence HPLC traces on a different HPLC used for sensitive fluorescence detection and quantitation of pDox conjugated and hydrolyzed off of the dendrimer. (C) It was found that there were multiple degradation peaks of pDox calibration standard.
Figure 14:
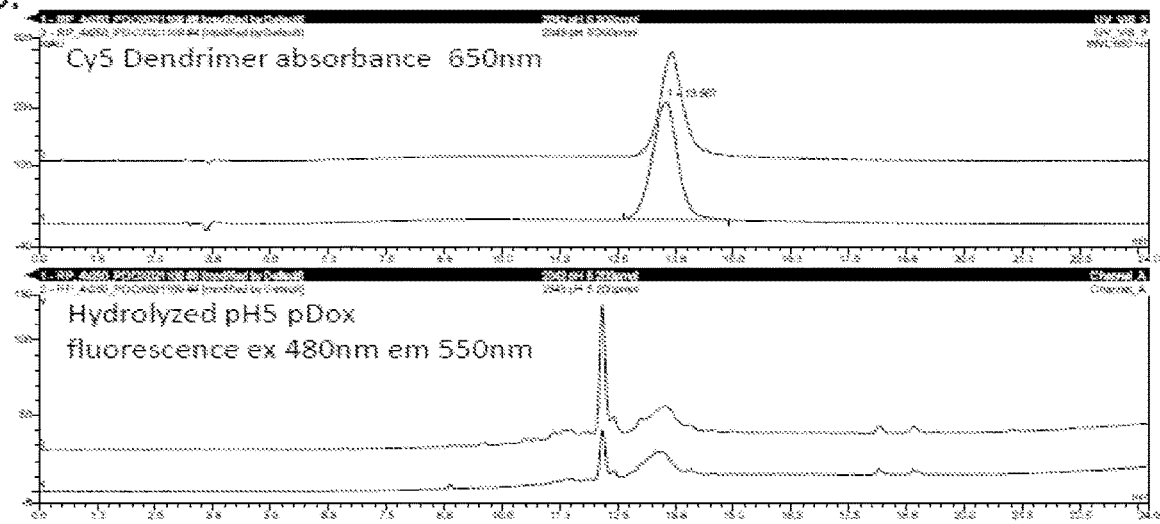
Figure 14:
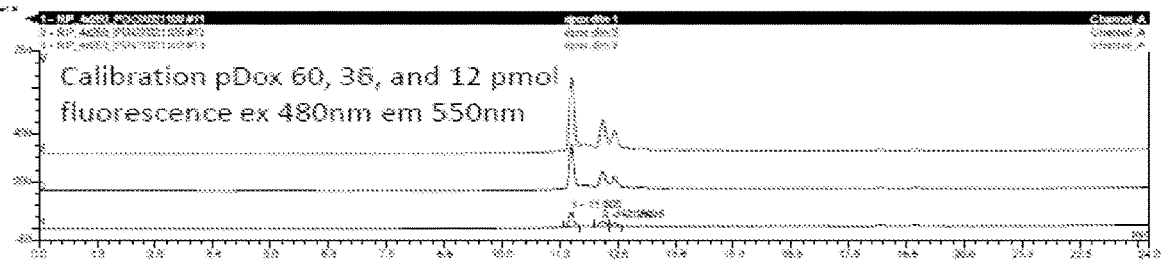

PAMAM dendrimers with doxorubicin conjugated on the surface were utilized. Briefly, linkers were synthesized and reacted to the surface of G5 PAMAM dendrimers. Lastly, doxorubicin was reacted to the dendrimers and purified by Amicon centrifugation columns. Yield was determined by weight and doxorubicin concentration calculated using 11,500/(M*cm) as the extinction coefficient. The thioether and the 3 different hydrazone dendrimer linkers are shown in FIG. 11, labeled as thioether, aromatic, urea, or Peg linkers. All dendrimers that were tested for hydrolysis of doxorubicin from the dendrimer were diluted into PBS pH 7.4 or 50 mM sodium acetate pH 5 for 18-22 hours and run on a tricine buffered SDS gel. Gels were imaged afterward on a UVP imager with 488 nm excitation and 600 nm emission. Selective transport molecule doxorubicin dendrimers were synthesized with 6 doxorubicin and 6 selective transport molecules per dendrimer. The selective transport molecule structure was Suc-$e^8$-oPLGC(me)AG-$r_9$-c as this is a faster cleaving MMP substrate and was reacted with the dendrimer through the thiol. For further purification dendrimers was resuspended after being lyophilized in 50% propylene glycol and 50% 20 mM Tris buffer. The dendrimers were centrifuged through a 0.2 μm nylon filter to clear any aggregates. Both filtered and unfiltered samples were run on a gel to confirm purification and surprisingly there was a greater amount of free doxorubicin and high molecular weight aggregate removed by this purification.

pDox dendrimers were synthesized with the intent to coat the dendrimers with one pDox and three Cy5s thus making the dendrimers brightly fluorescent in the far-red. The pDox dendrimer samples that were incubated overnight in pH 7.4 and pH 5 buffer as described previously were injected on HPLC/mass spec. HPLC was run using 30-60% Acetonitrile in water with 0.5% TFA gradient on a reverse phased column. Doxorubicin (470-490) and Cy5 (645-655) absorbance peaks were monitored to reveal a new doxorubicin peak in the pH 5 sample. This peak was proven to be free pDox based upon the mass spec. For quantitation, dendrimers were run on another HPLC using a different C18 reverse phase column with a 10-90% ACN gradient column with 0.14% TFA which has a fluorescence detector. The dendrimers ran differently between the two columns, which we attribute to different columns and different conditions. To quantify the amount of pDox that was hydrolyzed off the dendrimer, 200 pmols of sample was injected and compared to a standard curve of 12, 36, and 60 pmols of pDox alone. However, it became clear in this experiment that the pDox standard degraded as seen in FIG. 14.

Animal Experiments with Doxorubicin Dendrimers

In multiple experiments, HT1080 bearing nude mice were injected with a single specific dose of doxorubicin dendrimer. Injections, doses, number of doxorubicin/dendrimer and treated/control % are shown in Table 4 for each of these experiments. Mouse weights and tumor volumes were measured regularly. For the urea and the Peg hydrazone dendrimers, mice were imaged spectrally 7 days after injection. Using the Maestro (CRI) spectral deconvolution system and software, doxorubicin fluorescence (red) was separated out from autofluorescence (green). Tumors were removed and imaged by spectral deconvolution and brightfield. For aromatic and thioether dendrimers there were 4 mice for each treatment group but only 2 mice for the urea and Peg hydrazone dendrimers because of limited dendrimer synthesis yields. For the selective transport molecule dendrimer experiment 4 mice per treatment group were injected with 2 mg/kg of doxorubicin as a single dose into each mouse. Each mouse had two tumors for these experiments for a total of 8 tumors per treatment group. For the pDox-dendrimer experiments, 3 mice per treatment were injected with a single dose and each mouse had 2 tumors. The pDox dendrimer mice were imaged in the maestro small animal imager at 11 days post injection to detect Cy5 label in the dendrimers, revealing that there was a substantial amount of fluorescence remaining in the mouse. The mice had so much Cy5 distributed throughout, that the skin turned visibly blue.

Figure 10:
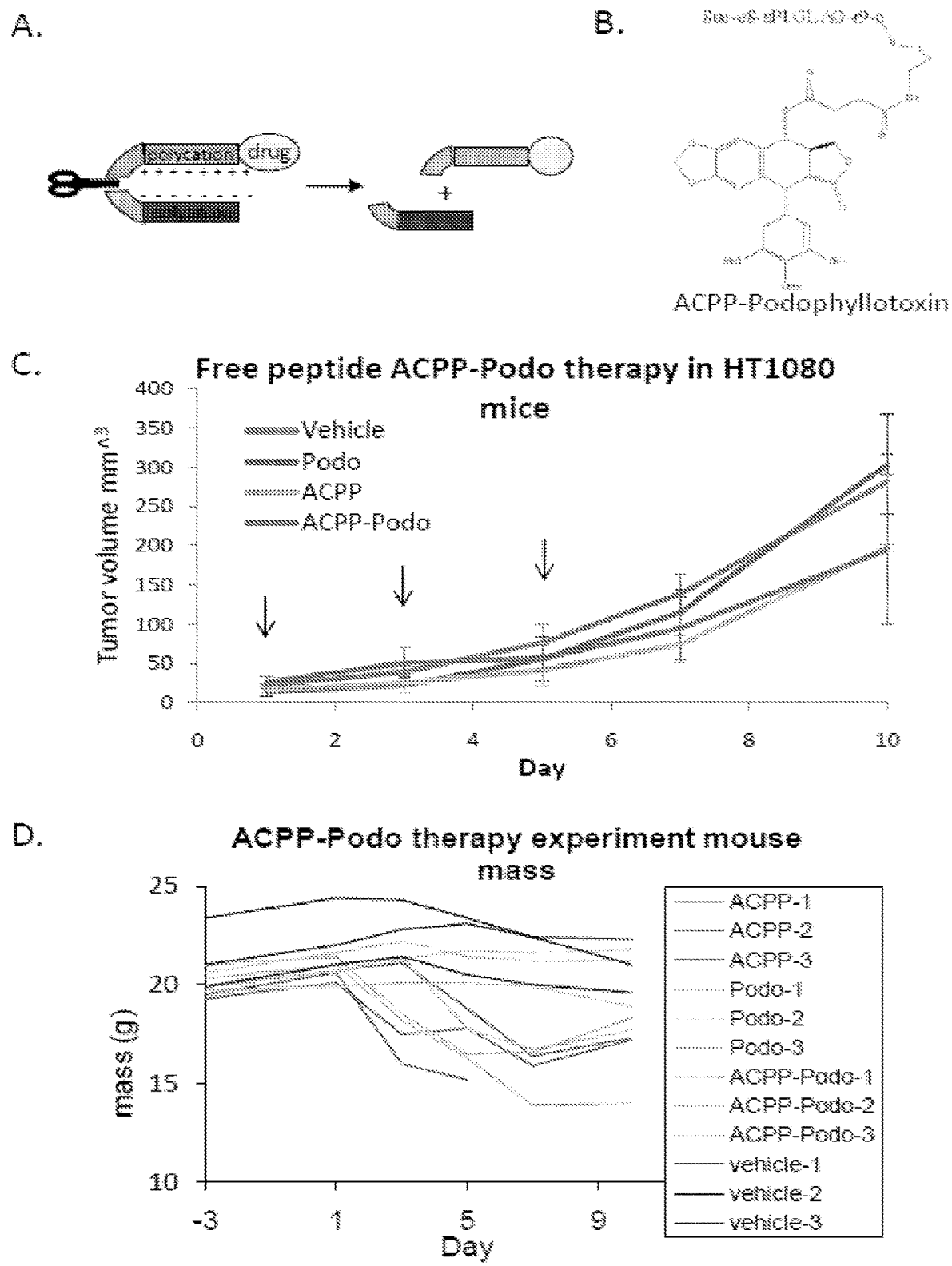
FIG. 10. Free peptide drugs had significant toxicity and little therapeutic activity. (A) Schematic of free peptide selective transport molecule based drug conjugation. Upon proteolysis the polyarginine-drug is released enabling cell uptake and therapeutic activity. (B) Structure of the Suc-$e_8$-xPLGLAG-$r_9$-c(ss-Podophyllotoxin) (selective transport molecule-Podo). (C) HT1080 xenografts were treated with IP injection of selective transport molecule-Podo drug conjugated and the vehicle, selective transport molecule, and Podo controls with 3 injections of 10 µmol/kg (arrow=injection day). The therapeutic activity of free peptide Podo had to do with toxicity of selective transport molecule treatment causing weight loss and morbidity after 3 doses. Podo alone had no therapeutic activity or toxicity. (D) Mouse mass throughout the duration of the experiment shows that selective transport molecule and selective transport molecule-Podo treatments lead to significant toxicity as conveyed by loss of body mass.

Free Selective Transport Molecule-Podophyllotoxin Conjugate Revealed More Activity Due to Peptide than Drug Although the probability of a successful free peptide drug conjugates was slim, we decided it was worth exploring at least one conjugate. Therefore we synthesized Suc-$e_8$-xPLGLAG-$r_9$-c(ss-podophyllotoxin) to test in cell culture. Since the peptide was found to have submicromolar toxicity on cells, we decided it was worth trying in animals, since the peptide synthesis was not very difficult. Therefore the selective transport molecule was synthesized as depicted in FIG. 10A and the final structure is shown in FIG. 10B. In order to decide upon a starting dose, we tested podophyllotoxin by itself to determine the effective dose for shrinking tumors. We found that 3 injections at 44 μmol/kg every other day was sufficient to significantly slow tumor growth but not provide a cure. There were no obvious signs of toxicity due to the podophyllotoxin (data not shown). These results were similar to those in the literature where minimal toxicity was found with 48-100 μmol/kg podophyllotoxin after multiple doses. For the initial selective transport molecule experiments we decided to try a dose of 44 μmol/kg selective transport molecule-podo, but found that this dose was acutely toxic. It was determined that there was significant toxicity due to just the selective transport molecule at these doses (as discussed in chapter 4). We therefore had to decrease the dose to a dose that was not toxic to the mice.

Due to repeated toxicity issues the dose was decreased to 10 μmol/kg of the selective transport molecule-podo administered as an IP injection to HT1080 tumor bearing mice. Three mice in each treatment group were injected with 3 doses, one dose every other day. Treatment groups were podophyllotoxin (podo) alone, selective transport molecule-podo, selective transport molecule alone, and H$_2$O vehicle. It was found that this treatment dose of podophyllotoxin was not efficacious, though both selective transport molecule peptides caused a modest slowing of growth (I0.1C). Based upon these results it appeared that the slowed tumor growth was not associated with the podophyllotoxin, but rather had to do with the presence of the selective transport molecule, which we knew was administered IP at a maximum tolerated IV dose. In addition to tumor growth curves it was found that both the selective transport molecule and the selective transport molecule-Podo injected mice lost significant weight during the experiment, suggesting that there was systemic toxicity due to the peptide (FIG. 10D). These data further suggest that due to selective transport molecule toxicity, drug conjugates such as podophyllotoxin cannot be considered in the free peptide form. Finally we did try the selective transport molecule -GFLG-Doxorubicin peptide and we were not able to see any therapeutic activity at a safe dose either (data not shown).

Conjugating Doxorubicin Via Hydrazone Linkage to PAMAM Dendrimers Reveal Anti-Tumor Effects.

The selective transport molecule configuration for therapeutic delivery that we felt had the most promise was the conjugation of drug directly to G5 PAMAM dendrimers. Because of the challenges of r$_9$-drug conjugates and hints that hydrazine could work, we decided to initially focus on conjugates with a stable thioether linker or various acid labile hydrazone linkers attached to doxorubicin. This allowed us to determine if there was therapeutic activity in animals with these types of conjugates. The benefit of the hydrazone linker as discussed earlier is that the native drug is release upon hydrolysis of the linker. The structures of the four linkers that were synthesized are shown in FIG. 11A with the stable thioether linker and the following three hydrazone linkers. These linkers were reacted with G5 PAMAM dendrimers and as a final step doxorubicin was reacted to the linkers. To test purity and acid sensitivity the dendrimer conjugates were incubated in either sodium acetate pH 5 or phosphate buffered saline pH 7.4 for defined time points. Though these experiments were not done at the same time, the qualitative differences are notable revealing that the peg linker was the most sensitive to hydrolysis. The urea and aromatic linkers were not very sensitive to acid treatment, with the urea linker possibly being slightly more stable. The thioether was clearly the most stable and had the least amount of free doxorubicin contaminant (FIG. 11B). Unfortunately we were unable to get any of these molecules completely free of free doxorubicin contaminant, but since it was a small percentage we continued testing these molecules in mice.

Figure 12:
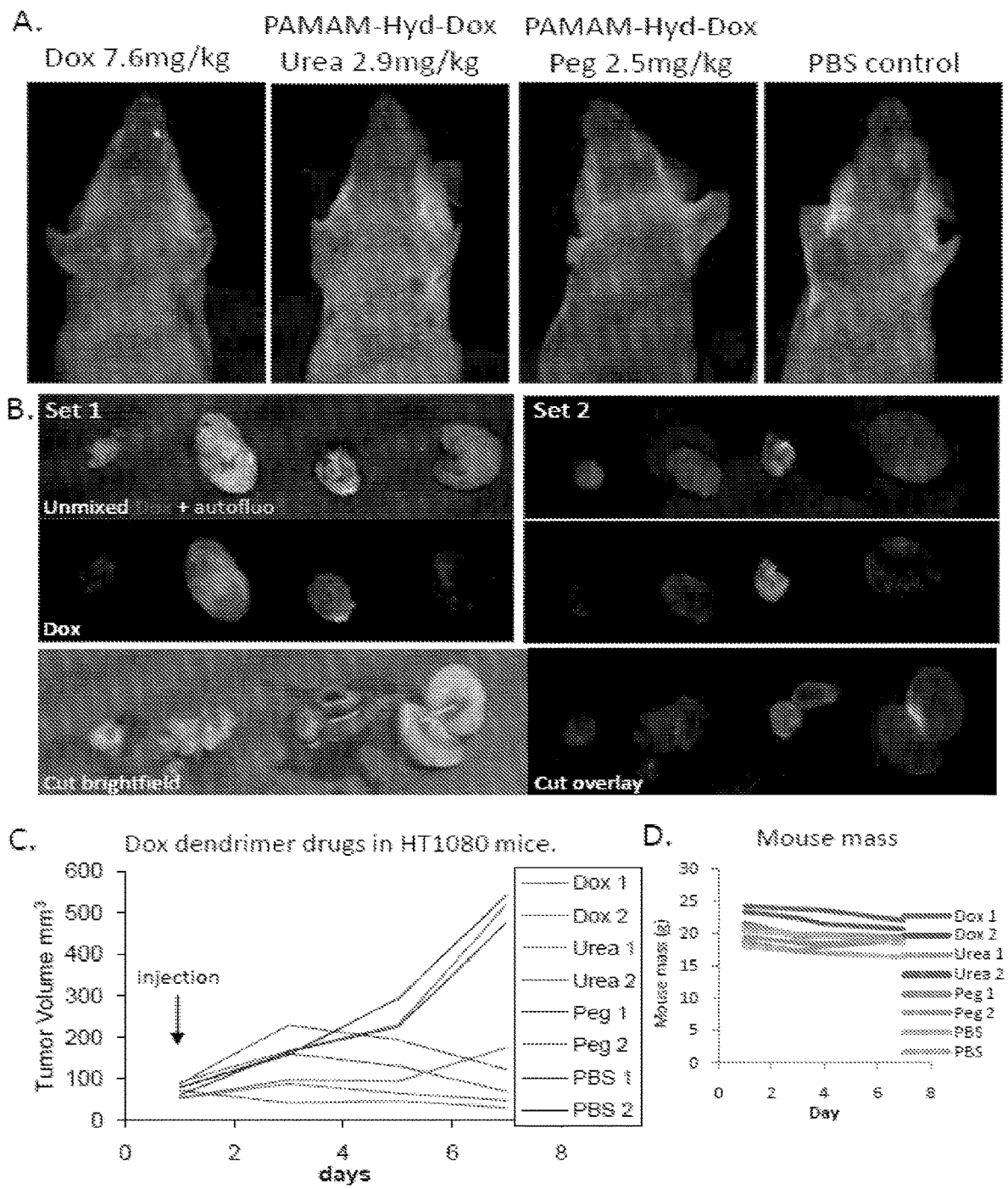
FIG. 12. Animal testing of the Urea and the Peg doxorubicin hydrazone linkers enabled imaging and therapeutic activity. (A) Images of mice treated with doxorubicin, Urea PAMAM hydrazone-Dox, the Peg PAMAM hydrazone-Dox, and a PBS control. The animals were excited with 467/47 excitation light and a spectral cube was collected. The doxorubicin fluorescence was the deconvolved from the images and overlayed on the autofluorescence. (B) The tumors of both sets of mice were imaged in the same way as the mice were after dissection; the deconvolved fluorescence is shown in grey scale below the overlay. The four treatment groups are in the same order as in (A) showing both sets of tumors from the experiment. Lower panel is a brightfield image and a spectrally deconvolved image of the one of the sets of tumors cut in half revealing the significant bloody necrotic core of the Peg dox dendrimer. (C) Tumor growth curves of all 8 mice in the Urea and Peg linker test experiment with injections done on day 1. (D) There was no significant change in body mass throughout the duration of the experiment.

All four doxorubicin conjugated dendrimers were tested in HT1080 tumor bearing mice as single dose injections and the results are summarized in Table 4. The table records the % mass of the treated compared to the control at the end of the experiment, showing how much anti-tumor activity the drugs had. It was found that peg linked dendrimers which had the greatest acid sensitivity yielded the best results by having a tumor mass to vehicle control as being 27% compared to 62% and 65% for the other two hydrazone dendrimers and no difference from the thioether linker. FIG. 12A-D shows images of mice, tumor growth curve, and change in mouse mass for the urea and peg hydrazone linkers. Surprisingly both these peg and urea linker dox derimers could be detected by fluorescence imaging using spectral deconvolution seven days after injection (FIG. 12A, B). When tumor growth curves were plotted it was revealed that the peg-hydrazone tumors had a significant tumor size regression during the course after injection (FIG. 12C). These two mice had significant anti-tumor effects after only a 2.5 (mouse 1) and 6.5 mg/kg (mouse 2) doxorubicin injection. There was no sign of toxicity from these experiments (FIG. 12D). This experiment revealed that the peg linker was superior to all other doxorubicin dendrimers tested, with a significant amount of tumor growth inhibition. However, in all of the experiments the control drugs doxorubicin and liposomal doxorubicin (Doxil) continually beat the dendrimers in anti-tumor activity. This could be due to the fact that a higher dose of these controls was used and also because they are very effective drugs. These data cannot determine if the dendrimer drug conjugates are better than controls until there is more data with more mice using escalating doses to determine the toxicity and thus the therapeutic index.

TABLE 4

| Molecule | Schedule | Vehicle | Dose of doxorubicin | Treated/ Control (%) |
|---|---|---|---|---|
| G5 PAMAM(Dox-hydrazone)$_3$ (aromatic) stable hydrazone | Single iv | PBS | 8.3 mg/kg | 62 |
| G5 PAMAM(Dox-hydrazone)$_{2.4}$ (urea) stable hydrazone | Single iv | PBS | 3 mg/kg | 65 |
| G5 PAMAM(Dox-hydrazone)$_{2.8}$ (Peg) most acid labile | Single iv | PBS | 4.5 mg/kg | 27 |
| G5 PAMAM -(thioether-Dox)$_3$ stable covalent linker | Single iv | PBS | 5 mg/kg | 100 |

Figure 13:
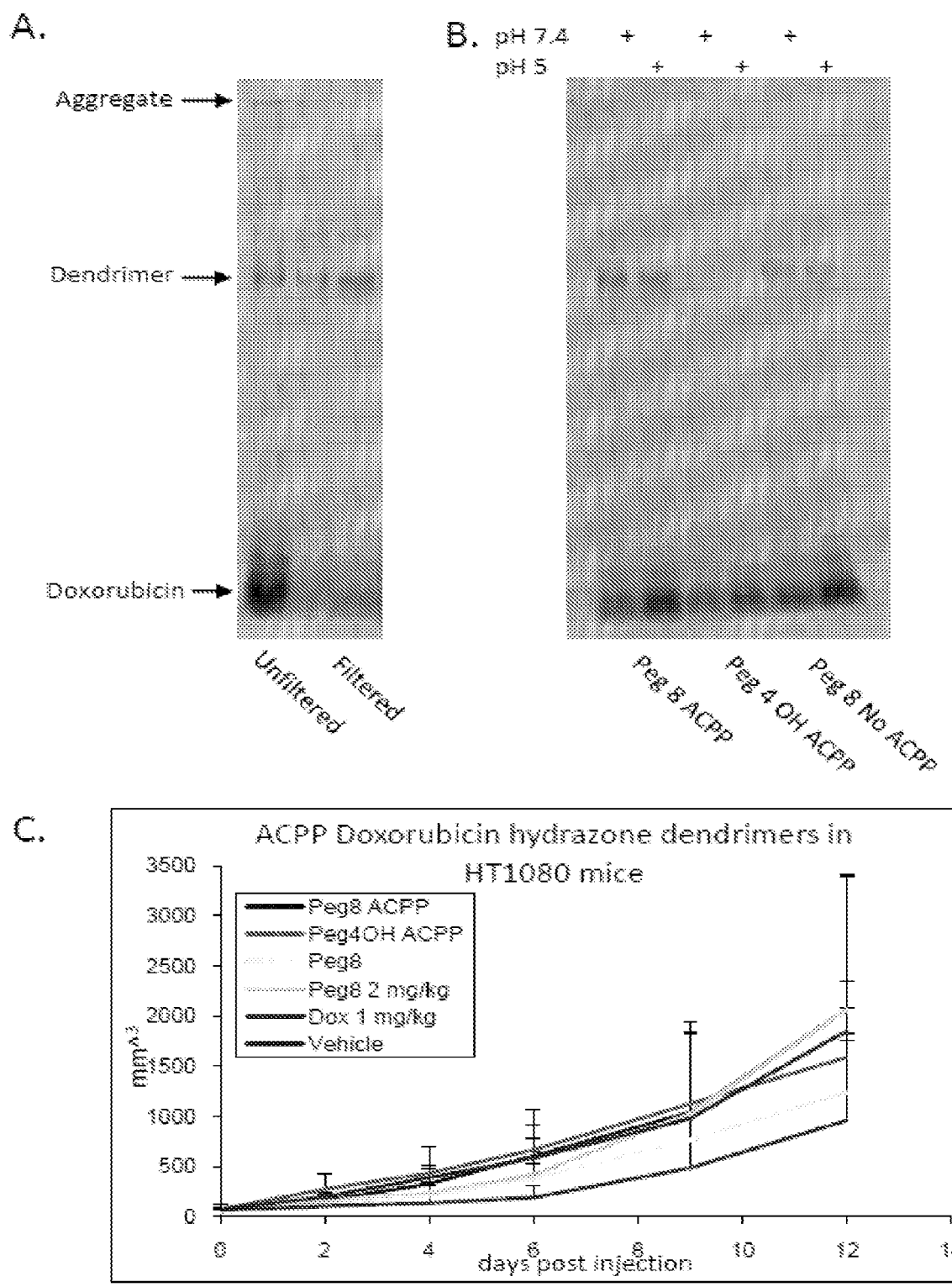
FIG. 13. Quality control and mouse experiments of selective transport molecule conjugated doxorubicin dendrimer. (A) Gel of resuspended doxorubicin dendrimer before and after column filtration revealing that much of the large molecular weight aggregate and free doxorubicin was cleared by this method of purification. (B) A gel of the 3 dendrimers that were synthesized and showing the capacity for doxorubicin to be hydrolyzed under acidic conditions. The gel shows the Peg 8 capped selective transport molecule G5 PAMAM dendrimer, the Peg4-OH capped selective transport molecule dendrimers, and the Peg8 capped doxorubicin dendrimers with no selective transport molecule. (C) Tumor growth curves of HT1080 xenograft mice injected with 1 mg/kg selective transport molecule containing dendrimers revealing that the low dose of doxorubicin alone and doxorubicin coated dendrimers was not sufficient to significantly inhibit tumor growth.

Adding Selective Transport Molecules to the Doxorubicin Conjugated Dendrimers Significantly Decreased the Solubility After screening for hydrazone linkers that worked best on the dendrimers we synthesized a new batch of dendrimers with selective transport molecules conjugated to the surface. We synthesized G5 PAMAM dendrimers with 6 selective transport molecules and 6 doxorubicin, expecting these modest numbers would not lead to solubility issues as we had in the past with Cy5 containing dendrimers. In principle more than 100 drugs could be loaded on the surface, but we avoided these options anticipating significant solubility problems as seen with dendrimers that had 30 Gadolinium molecules for MRI studies. We synthesized 2 different dendrimers with either Peg8 or Peg4-OH caps to cap all the unreacted amino groups on the PAMAM dendrimers to further enhance solubility, which was also different than optical and MrII dendrimers that used Peg4 as a capping reagent. Lower aggregation was determined with Peg8 and Peg4-OH compared to Peg4 in other studies (data not shown). Initially the dendrimers were suspended in propylene glycol after being lyophilized. The fractions had a significant amount of free doxorubicin and aggregates so they were filtered through a 0.2 μm filter and both the aggregates and free doxorubicin decreased though not completely (10.4A). We then treated each dendrimer, the Peg8 dox dendrimers alone, the Peg8 selective transport molecule dox dendrimer, and the Peg4-OH selective transport molecule dox dendrimer by incubating them in pH 5 and pH 7.4 overnight to detect hydrolysis of doxorubicin. Each of these dendrimers had an increase in doxorubicin hydrolysis when at low pH but these data were not dramatic (10.4B). We think that we lost a lot of the doxorubicin during resuspension in propylene glycol before addition of Tris buffer because it was found that the conditions were very acidic. Though we were rather discouraged we decided to inject 1 mg/kg of doxorubicin equivalents into mice because of limited supply and solubility. These dendrimers were found to have no significant effect on tumor growth probably because of the low doses which are not very effective as free doxorubicin (FIG. 13C).

More Potent 2-Pyrrolino Doxorubicin Enhanced Selective Transport Molecule Dendrimer Potency, but the Drug was Unstable The solubility and aggregation problems with selective transport molecule coated dendrimers were realized to be major problems. There are multiple variables that might cause aggregation, the two most important are likely the number of selective transport molecules on the surface and the number of drugs conjugated. We therefore decided to decrease the number of Selective transport molecules to approximately four per dendrimer. In addition, we decided to move away from doxorubicin and use 2-pyrrolino doxorubicin (pDox) which is 500 times more potent. These conjugates would decrease the amount of dendrimer necessary to inject for therapeutic activity, which would enable coating dendrimers with fewer drugs or not needing such high concentrations, ultimately reducing the solubility issues. Lastly, we found that the negatively charged Cy5 on the surface of the dendrimers helped by decreasing aggregation of the dendrimers, so we added Cy5 to the pDox dendrimers. Therefore, we made a G5 dendrimer with three Cy5's, one pDox, and in the presence or absence of four selective transport molecules.

Figure 15:
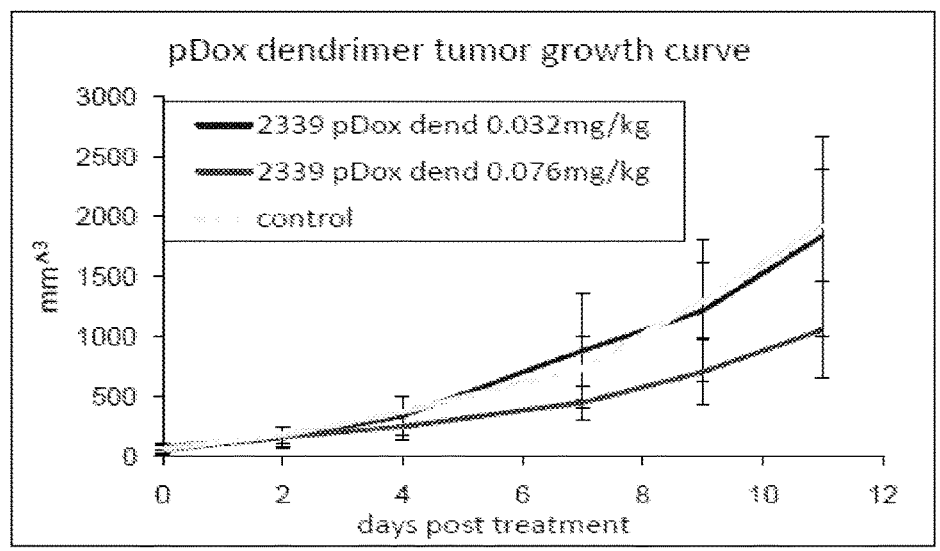
FIG. 15. pDox dendrimers slow tumor growth and the Cy5 dendrimer fluorescence can be detected 11 days after injection. (A) Tumor growth curves of HT1080 xenografts showing that the higher dose of pDox dendrimer did slow tumor growth greater than the vehicle and the lower dose. (B) Upon sacrifice and dissection of pDox dendrimer treated mice fluorescence images were taken demonstrating that even after 11 days a substantial amount of dendrimers remained throughout the mouse.
Figure 15:

Before testing these dendrimers we found that the maximum tolerated dose of pDox in HT1080 bearing mice was 0.1 mg/kg which is a dose that significantly slowed tumor growth. Two mice each died within 24 hours after being injected with 0.3 and 1 mg/kg of pDox. This dose was about 50-100 times lower than the maximum tolerated dose of doxorubicin in these mice.

pDox was synthesized and reacted with the dendrimer via hydrazone linker as done with doxorubicin dendrimers discussed earlier. IT was difficult to confirm that the pDox reacted with the dendrimers. The labeling was so low that the absorbance was undetectable by UV Spectroscopy. It was only by fluorescence spectra measured on a plate reader that it was clear pDox was conjugated to the dendrimers but this was not able to be quantified. The dendrimers were next incubated in pH 5 buffer and we tried to detect pDox by LC/MS. After hydrolysis the absorbance of the pDox was detectable with the HPLC absorbance detector and the peak was confirmed by mass spec (FIG. 14A). However, we were unable to confirm the concentration. We next determined the concentration of pDox by using HPLC with a fluorescence detector and comparing with a fluorescence standard (FIG. 14B). These data gave us confidence to quantify the pDox within a fold difference, but because of degradation problems these measurements may not be very accurate. Using sensitive analytical HPLC and mass spectra we discovered that the pDox had severe stability problems, breaking down into multiple peaks (FIG. 14C). The stability was likely a big enough issue that the labeling yield was less than 1 pDox per dendrimer. However, a few mice were injected with the no selective transport molecule coated dendrimer to determine if there was at least some level of anti-tumor activity. These experiments demonstrated substantial antitumor effects with a dose less than 0.1 mg/kg of pDox dendrimers, but the experiments were abandoned because of the pDox stability and low labeling efficiency (FIG. 15A). Upon imaging the mice 11 days after the injection, there was a substantial amount of pDox Cy5 dendrimer in the tumors demonstrating that this approach still has substantial promise if the right stable dendrimer drug combinations were synthesized (FIG. 15B). The selective transport molecule containing pDox dendrimer was never tested because of the low labeling efficiency and because it was nearly impossible to reliably inject the same dose of pDox dendrimer as selective transport molecule pDox dendrimer.

Example 4: Selective Transport Molecules Conjugated to Liposomes

Selective Transport Molecule Peptide Synthesis for Nanoparticles

To react selective transport molecule to Abraxane the following peptide was synthesized c-$e_9$-oPLG(Cme)AG-$r_9$-k by solid phase synthesis as described in earlier chapters. Crude peptide was then reacted with Cy5-monomaleimide to the n-terminal cysteine in DMF and NMM. The peptide was purified by HPLC and reacted with maleimido propionic acid PFP ester in DMF and NMM. After purification the final peptide structure was c(Cy5)-$e_9$-oPLG(Cme)AG-$r_9$-k(CO(CH$_2$)$_2$-maleimide). For the DSPE-selective transport molecule-Cy5 e9-oPLG(Cme)AG-r9-c and $e_9$-(Peg$_2$)$_2$-$r_9$-c peptides were synthesized by solid phase chemistry and purified by HPLC. The peptide was reacted with 1,2-distearoyl-sn-glycero-3-phosphoethanolamine-N-[maleimide(polyethylene glycol)-2000] (DSPE-Peg(2000)-maleimide) (Avanti Polar Lipids) in DMF and NMM, then reaction was monitored by HPLC. When near complete, Cy5-NHS ester was added to the reaction and that reaction was monitored by HPLC. After completion of synthesis the DSPE-selective transport molecule-Cy5 was purified by HPLC.

Reaction of Selective Transport Molecule to Abraxane and Cleavage of Peptide

Cy5-selective transport molecule-Maleimide peptide was mixed at 1 and 10% molar percent to albumin, in resuspended Abraxane in normal saline. Reaction tubes were either sonicated for 30 seconds 3× in a bath sonicator or left at untouched at room temperature for 30 minutes or 24 hours. At the final time point, the reaction was stopped by the addition of tricine sample buffer and heating to 90 C for 10 minutes. Samples were then run on a 10-20% tricine buffered gel and imaged for Cy5 fluorescence on the UVP gel imager. For the enzyme cleavage assay, the selective transport molecule liposomes and Abraxane were incubated with 50 nM recombinant MMP-9 (EMD) in 20 mM Tris 150 mM NaCl for specific time points, quenched by adding tricine sample buffer and heated at 90° C. for 10 min. Samples were then run on a 10-20% tricine buffered gel and imaged by fluorescence on the UVP gel imager.

Characterization of Selective Transport Molecule Nanoparticles by Dynamic Light Scattering Prepared samples of liposomes and Abraxane were diluted 1-100 from synthesized concentrate into a 300 mM sucrose solution buffered with 2 mg/mL of histidine pH 6.5. The samples were then measured by dynamic light scattering on the Zetasizer (Malvern). 2-3 measurements were taken from an average of 10 runs to determine the size as a function of intensity and volume. The results were then plotted by volume % and size in nm to show that the samples were either a monodispersed Gaussian distribution in size or aggregated.

Synthesis of Selective Transport Molecule Containing Liposomes

Liposomes were synthesized by making a lipid cake with 11:7:1 proportions of hydrogenated soy phosphatidyl choline: cholesterol: 1,2-distearoyl-sn-glycero-3-phosphoethanolamine-N[methoxy(polyethylene glycol)-2000] (DSPE-Peg(2000) (Avanti Polar lipids) at a total of 30 µmols of lipid similar to previous studies. For selective transport molecule containing liposomes, different mole ratio of DSPE-selective transport molecule-Cy5 to DSPE-Peg(2000) were mixed in before cake formation. The lipid cake was hydrated with heat and bath sonication with 250 mM ammonium sulfate and 50 mM Sucrose histidine buffer 0.33 mg/mL. Multilamellar vesicles were heated to 60° C. and were sonicated using a probe sonicator for 2 minutes to make small unilamellar vesicles (SUV). The SUVs were then extruded 20 times through a 0.2 and then a 0.1 µm membrane filter (Whatman) at 60° C. on a heat block mini-extruder (Avanti Polar Lipids). After extrusion liposomes were buffer exchanged into 300 mM sucrose 2 mg/mL sucrose buffer at pH 6.5 using a sephadex G25 (Sigma-Aldrich) column to clear all the extraliposomal ammonium sulfate. The liposomes were then incubated with 15 mgs of doxorubicin for 1 hour at 60° C. and then filtered through a Sepharose CL-4B column (Sigma-Aldrich) and stored at 4° C. For concentration measurements liposomes were disrupted with 1.5% trition-X solution, sonicated in a bath sonicator and the total doxorubicin concentration measured by absorbance using 11,500 $M^{-1}$ $cm^{-1}$ as the extinction coefficient.

Cell Imaging of Doxorubicin in Selective Transport Molecule Doxorubicin Liposomes HT1080 cells were plated in a 96 well coverslip bottom plate and treated with various liposome formulations for 25 minutes in serum free conditions. The cells were then washed 3× over 30 minutes and imaged for doxorubicin fluorescence by confocal microscopy (Zeiss, LSM 5 Live) using 488 nm laser and 550 LP emission filters. After treatment cells were imaged for up to 72 hours while being in normal growth media and incubator between imaging.

Animal Studies for Testing Selective Transport Molecule Liposomes

Figure 20:
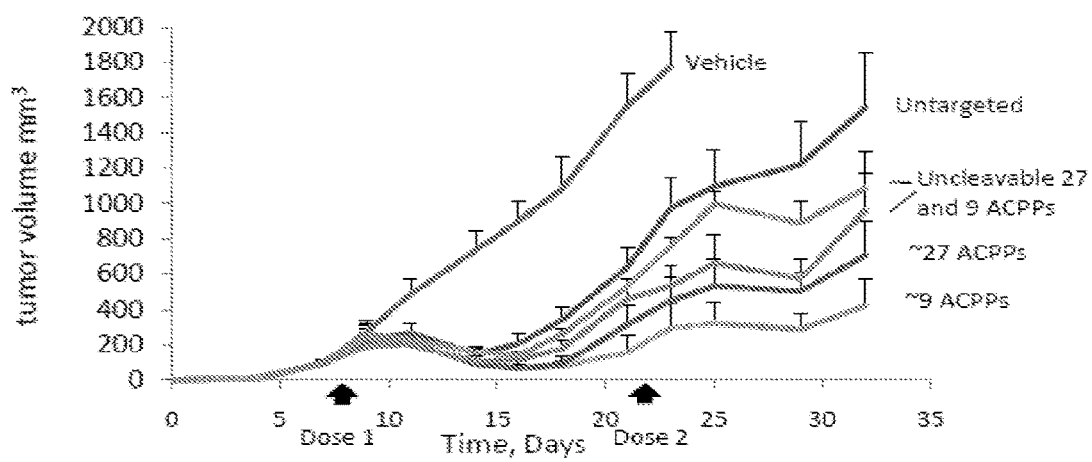
FIG. 20. Fewer selective transport molecules have a greater therapeutic effect; Uncleavable control peptide not as effective as cleavable peptide. (A) Eight HT1080 mice per treatment group with one tumor each were injected with 3 mg/kg doxorubicin equivalents on day 8 and 22. The 0.1 and 0.3 mole % peptides are labeled as ~9 or 27 selective transport molecules per liposome. These data show that decreasing the number of selective transport molecules further increases the therapeutic effect of the tumor growth curves. (B) The chart shows the p-value determined by t-test at day 18, 21, 25, and 29. At every time point there was statistical significance between the 9 selective transport molecules and the untargeted control having up to a 4 fold difference in tumor volume. These data show both the 0.1 and 0.3 mole % compared to the untargeted liposomes as wells as a comparison of the cleavable versus the uncleavable versions of the peptide. (C) All treatment groups had a loss of weight by the end of the experiment.
Figure 20:
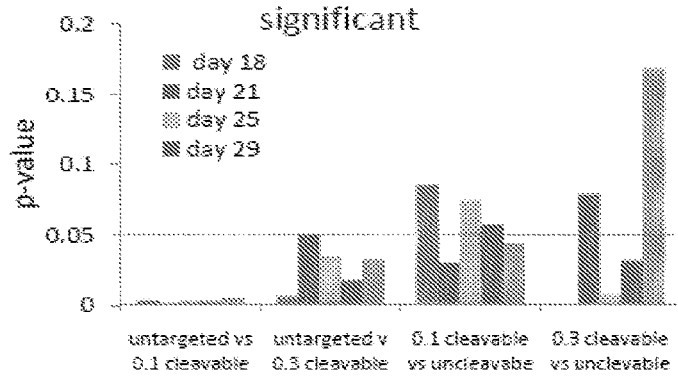
Figure 20:
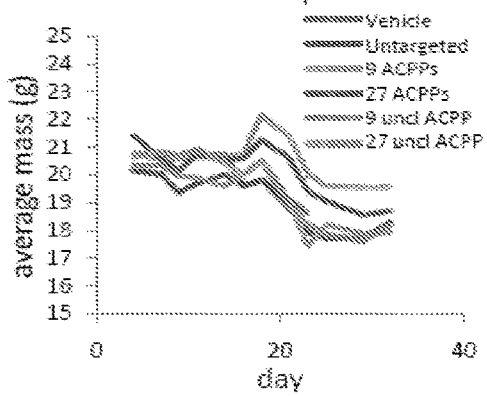

Nude mice were injected subcutaneously with $1X0^6$ cells in the right and or left mammary fat pads to produce xenografts. One week later, after tumors became 50-250 $mm^3$, mice were injected intravenously (IV) with vehicle, doxorubicin liposomes, or selective transport molecule coated doxorubicin liposomes at approximately 3 mg/kg of doxorubicin. Mouse tumor measurements and weights were taken at regular intervals. For some experiments mice were injected with a second dose. When tumor volumes reached near maximum the animals were sacrificed, tumors were weighed and imaged. All animal protocols were approved by the UCSD IACUC. The experiment in FIG. 20 was performed by Explora Biolabs because of greater resources necessary for increase number of treatment groups and larger n.

Synthesis and Validation of Selective Transport Molecule Coated Abraxane

Figure 16:
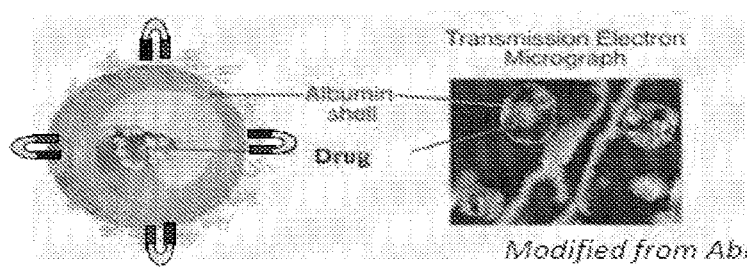
FIG. 16. selective transport molecules can be synthesized to coat Albumin suspensions of paclitaxel. (A) Schematic from Abraxis website of Abraxane depicting colloidal paclitaxel suspended in a 130 nm albumin shell and a transmission electron micrograph of the nanoparticle. Here we depict that we can react selective transport molecule to the surface of the Abraxane which could be used for enhanced targeting of Abraxane to tumors. (B) We show that 1 and 10% mole percent selective transport molecule to albumin can react up to 84% of selective transport molecules on the surface of Abraxane within 30 minutes of resuspension. This robust reaction is independent of longer incubation times or sonication. (C) Once reacted to the Abraxane selective transport molecule can be cleaved off of the nanoparticle upon treatment with MMP-9 enzyme, being near complete within one hour. (D) Dynamic light scattering confirming that resuspended Abraxane with and without selective transport molecule peptide are mono disperse and have a z-average diameter of 130 nm.
Figure 16:
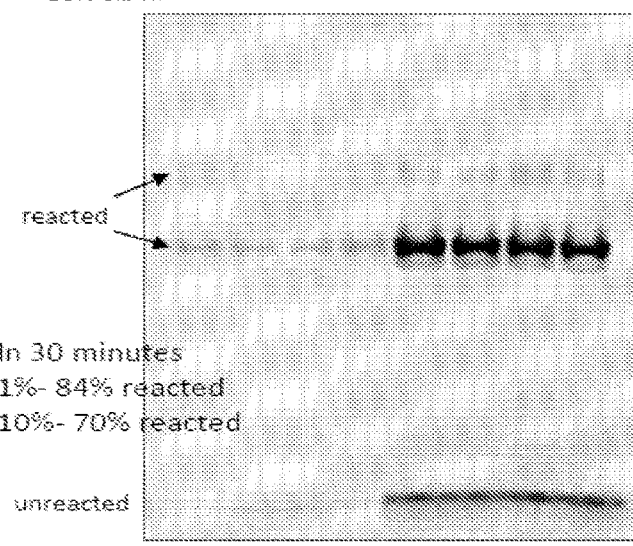
Figure 16:
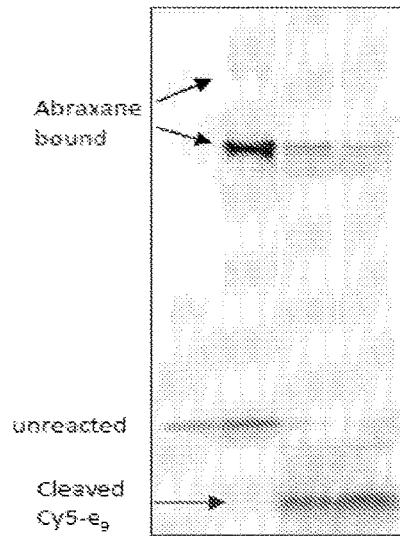
Figure 16:
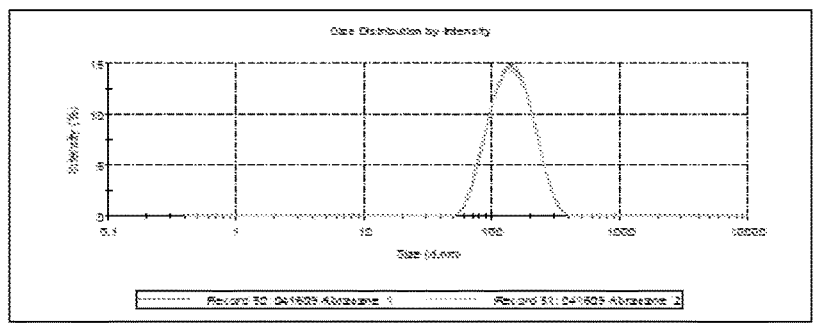

One method of using selective transport molecules to target nanoparticles is to coat the surface of albumin paclitaxel suspensions with peptides. A selective transport molecule that could react with albumin similar to the one discussed in chapter 7 was synthesized. The sequence for this design was (Cy5)c-e9-oPLG(Cme)AG-r9-k-maleimide (FIG. 16A), with the intention that the maleimide would react with C34 on albumin and then upon cleavage the Cy5c-$e_9$ would be cleaved off the Abraxane. After synthesis and purification, 1% and 10% molar equivalents of selective transport molecule to albumin molecules were mixed with freshly suspended Abraxane at a high concentration suitable for animal injection. Parallel reactions were stopped after 30 minutes and 24 hours with and without being sonicated. Surprisingly we found that regardless of sonication the reaction was driven to completion in less than 30 minutes in normal saline (the injection buffer) as show by gel electrophoresis (FIG. 16B). It was determined that 84% and 70% of the selective transport molecule reacted with the albumin from the 1% and 10% reaction respectively. This was measured by the integrated intensity of fluorescence that reacted with albumin vs. remained as a free peptide. After the peptide was reacted with Abraxane, dynamic light scattering revealed that the nanoparticles were unaggregated with a z-average of approximately 130 nm for reaction mixtures containing 0.3%, 1%, 3% selective transport molecule and no selective transport molecule (FIG. 16C). When the selective transport molecule reacted Abraxane was incubated with MMP-9 enzyme the Cy5c-$e_9$ was readily cleaved off the nanoparticle as detected by gel electrophoresis (FIG. 16D). With these clean and simple results the next series of experiments will consist of testing these conjugates for therapeutic activity in animals.

Synthesis and Validation of Selective Transport Molecule Coated Liposomes

Figure 17:
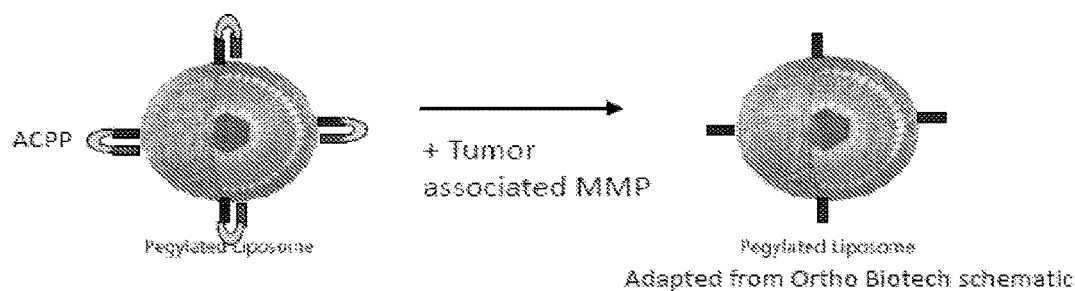
FIG. 17. Doxorubicin containing pegylated liposomes can be coated with selective transport molecules. (A) Schematic of selective transport molecule coated liposomes. Cleavage by MMP enzymes lead to restored CPP properties and enhanced cellular uptake. (B) Chemical structure of the DSPE-selective transport molecule-Cy5 that was synthesized for the incorporation in to pegylated liposomes during formulation. (C) Representative size to % volume dynamic light scattering plot of selective transport molecule coated pegylated liposomes containing doxorubicin. This reveals that the liposomes were mono-disperse with a z-average size of 130 nm. (D) selective transport molecule coated doxorubicin liposomes can be cleaved off of the liposome surface upon incubation with MMP-9. SDS-PAGE confirmed that much of the Cy5-e₉ was cleaved from the incorporated DSPE-selective transport molecule-Cy5.
Figure 17:
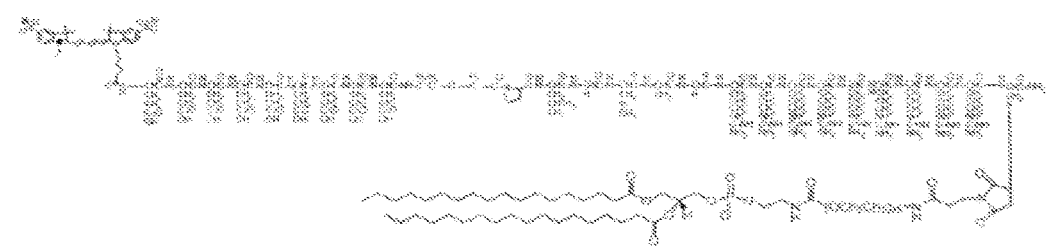
Figure 17:
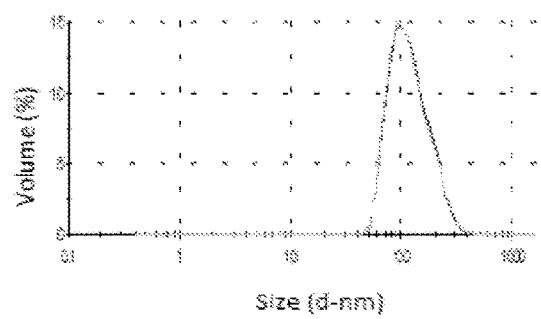
Figure 17:
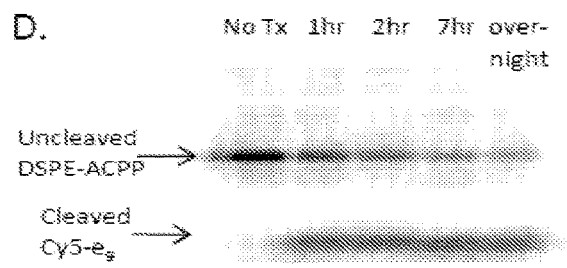

In order to synthesize liposomes with selective transport molecules on the surface as depicted in FIG. 17A we had to first synthesize a phospholipid with the selective transport molecule attached. To do this the following peptide was synthesized, Cy5-$e_9$-oPLG(Cme)AG-$r_9$-c. In this sequence the free thiol on the peptide could be reacted with 1,2-distearoyl-sn-glycero-3-phosphoethanolamin-N-[maleimide (polyethylene glycol)-2000] (DSPE-Peg(2000)maleimide). The Cy5 was reacted to the n-terminus because then cleavage can be confirmed in vitro, something that was never possible with the way Gadolinium dendrimers were synthesized.[53] Once reacted, the peptide was purified as DSPE-selective transport molecule-Cy5 (structure FIG. 17B) and used for incorporation into liposomes (FIG. 17A). Initially we tried to incorporate the DSPE-selective transport molecule-Cy5 into premade pharmaceutical grade Doxil with no success shrinking tumors compared with Doxil alone. At the time we did not have a method to confirm that selective transport molecule was incorporated and as we discovered later, we were incorporating too many selective transport molecules into the liposomes.

Liposomes were made in the lab with the composition of 11:7:1 Hydrogenated Soy Phosphatidylcholine (HSPC): Cholesterol: DSPE-Peg(2000) to reflect as close as possible the formulation of the pharmaceutical Doxil. Liposomes were made with varying concentrations of DSPE-selective transport molecule-Cy5 by mixing various molar ratios of the selective transport molecule before hydrating and extruding the lipids through a 100 nm membrane. Concentrations ranged from 0.1-3 mole % of the DSPE-Peg(2000), these ranged from approximately 9-270 selective transport molecules per liposome. Dynamic light scattering confirmed that the liposomes had an average size (z-average) of approximately 130 nm, a representative % volume to size plot is shown in FIG. 17C. To ensure the selective transport molecule was present on the surface, liposomes were treated with MMP-9 in a test tube to verify that enzymes had access to the selective transport molecule and that the peptide was cleaved by the enzyme (FIG. 17D).

Selective Transport Molecule Enhances the Uptake Doxorubicin into Cells

Figure 18:
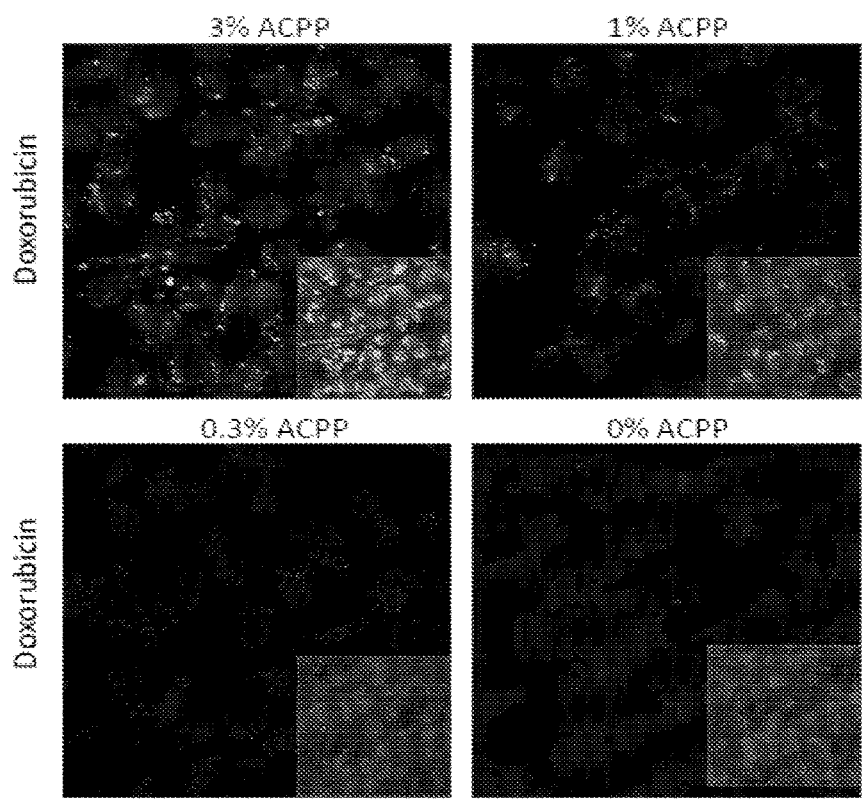
FIG. 18. A linear relationship of surface selective transport molecules on liposomes and uptake in culture, but not in vivo. (A) HT1080 human fibrosarcoma cells were incubated with 50 µM of doxorubicin in selective transport molecule coated pegylated liposomes for 30 minutes then washed 3 times and imaged an hour after initial treatment. Confocal microscopy showed that there is greater doxorubicin (green) take up into cells with greater mole % of pegylated lipids containing selective transport molecules. The 0.3% and no selective transport molecule liposomes were difficult to detect unless images were rescaled (inset). (B) The 0.3, 1, and 3 mole % of selective transport molecule coated liposomes were injected IV into HT1080 tumor bearing xenograft mice at 3 mg/kg equivalents of doxorubicin. These treatments were compared to vehicle control (300 mM sucrose buffer) and untargeted doxorubicin liposomes. The 0.3% selective transport molecule was statistically significant compared to the Doxorubicin liposomes from day 10-17 (p-value <0.02, t-test). Four mice each with two tumors were treated per group (except 3 mice for the 3% selective transport molecule).
Figure 18:
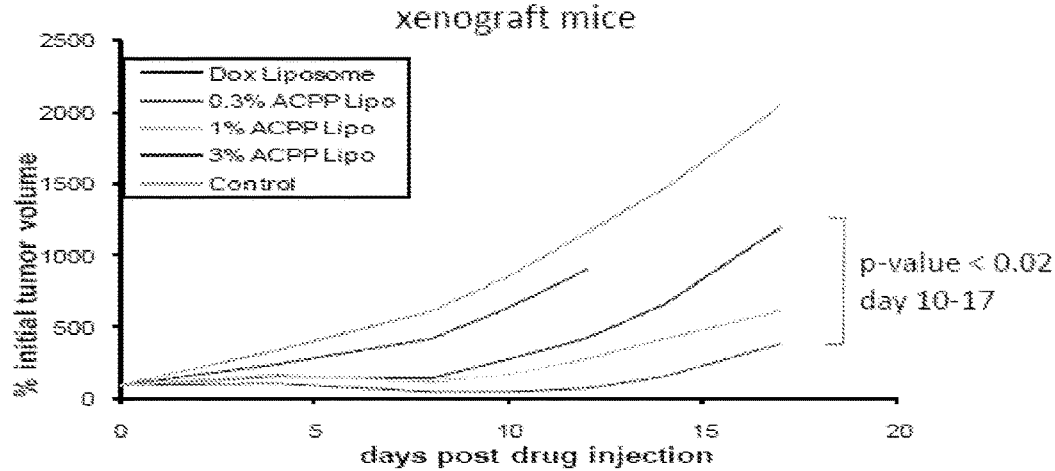

Following validation of selective transport molecule incorporated liposomes we wanted to know if selective transport molecule increased the uptake of doxorubicin into cells in culture. To determine this we incubated HT1080 human fibrosarcoma cells with liposomes containing varying amounts of selective transport molecule. The amount of doxorubicin inside cells after an hour long incubation increased with increasing amount of selective transport molecule on the surface of the liposomes (FIG. 18A). Though there was a significant amount of doxorubicin uptake most of the drug in all treatments appeared to be predominately in endosomal puncta. However, when images were brightened it became evident that doxorubicin could be detected inside of nuclei of cells (FIG. 18A inset).

Anti-Tumor Efficacy of Selective Transport Molecule Coated Liposomes is Dependent Upon the Number of Selective Transport Molecules Coating the Liposomes With these encouraging data, selective transport molecule liposomes were injected into tumor bearing mice to determine whether selective transport molecule coated liposomes could have a greater anti-tumor effect than untargeted liposomes. HT1080 tumor bearing mice were injected with 3 mg/kg doxorubicin equivalents of liposomes into 4 mice per treatment group. Each mouse had 2 tumors to increase the number of tumors per treatment group. When tumors were between 50 and 200 mm$^3$ mice were injected with a single IV injection of 0.3, 1, and 3 mole % of selective transport molecule to DSPE-Peg(2000) liposomes, untargeted doxorubicin liposomes and vehicle alone (sucrose buffer). Mouse weights and tumor volumes were measured regularly for 17 days post injection. The % change in tumor volume was plotted over time revealing that the greatest anti-tumor activity was with the 0.3% selective transport molecule doxorubicin liposomes. The 1% and untargeted liposomes were similar in their antitumor activity and the 3% were much worse. These data suggest that a lower number of selective transport molecules on the surface of the liposomes increases the therapeutic activity, which is contrary to the uptake in tissue culture (FIG. 18A, B). There was statistical significance between the 0.3% and the untargeted liposomes from day 10 through day 17 with a p-value <0.02 as determined by a two-tailed t-test. Mice remained healthy for the entire experiment and there was no significant weight loss due to toxicity of the liposomes throughout the duration of the experiment (data not shown).

Figure 19:
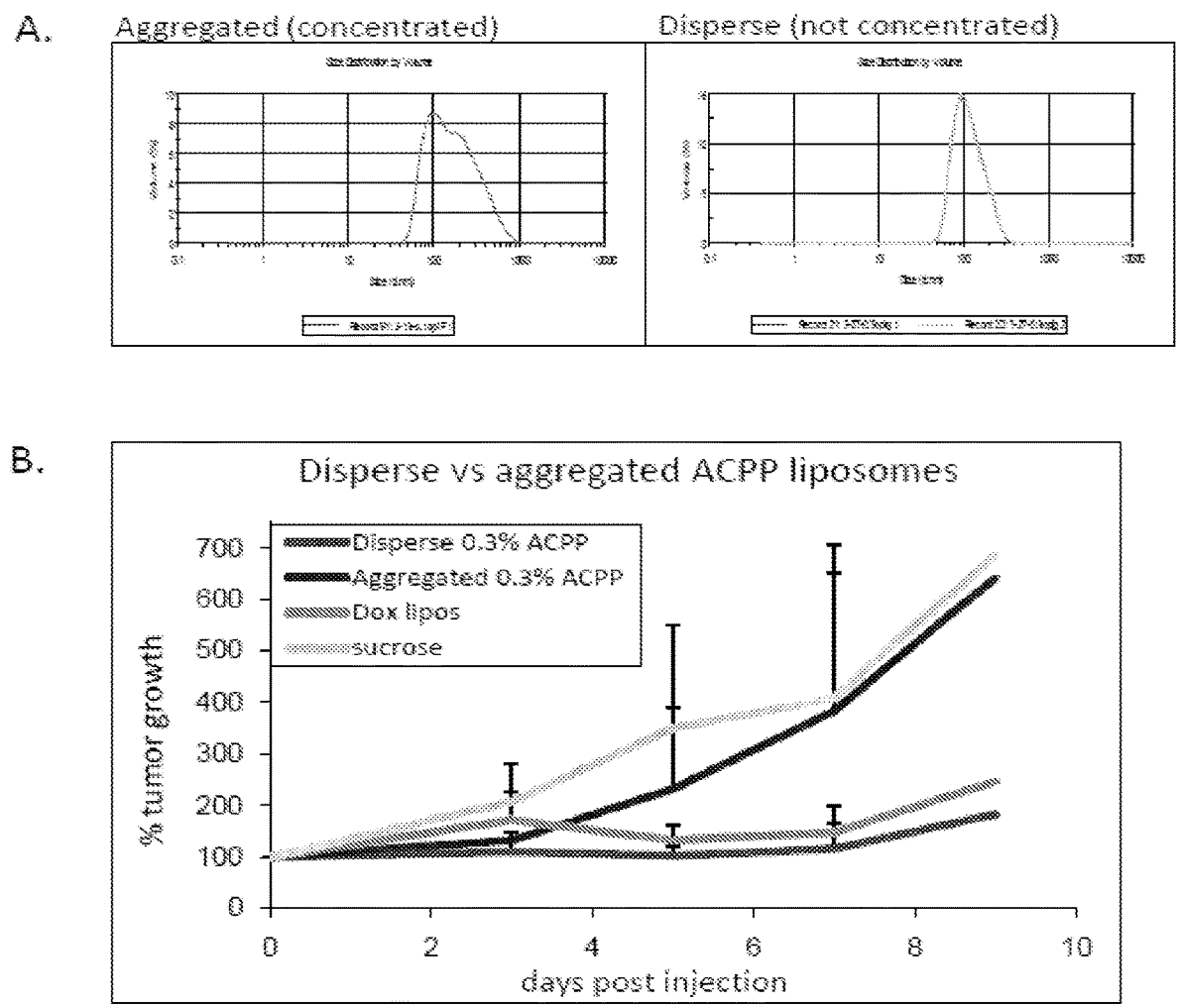
FIG. 19. Aggregation causes the therapeutic effect to disappear. (A) Dynamic light scatter revealed that a preparation of liposomes was aggregated after they were concentrated by centrifugation. This aggregation was present after passing through a 0.2 µm filter. The left panel shows the micro aggregates of a 0.3 mole % doxorubicin liposome preparation, the right panel shows a fresh unconcentrated preparation. (B) The aggregated liposomes have no therapeutic effect in animals when tested head to head with the unaggregated preparation. Four mice with 2 tumors each were injected with 3 mg/kg of the 0.3% fresh preparation, the untargeted doxorubicin liposomes, and vehicle alone.

Aggregation Abrogates the Effects of Selective Transport Molecule Coated Liposomes It was discovered that sometimes there was a problem with aggregation of the liposomes when they were concentrated by centrifugation using an Amicon column. When aggregation occurred the therapeutic affect disappeared. Knowing that this was possibly a problem with multiple types of targeted nanoparticles this problem needed to be clearly defined and avoided. Therefore size and dispersion of two batches of 0.3% selective transport molecule liposomes were measured by dynamic light scattering. It was verified that the centrifuged batch that was aggregated and the fresh unconcentrated batch normally disperse (FIG. 19A). Without light scattering measurements aggregation can be qualitatively determined by extruding the liposomes through a 0.2 μm membrane filter at room temperature to determine if there is significant resistance. If there are no problems with aggregation then the liposomes can be extruded easily whereas the presence of aggregates significantly increases the resistance. To test whether aggregation affects tumor growth inhibition the two batches were injected into HT1080 xenografted mice. Mice with two tumors each were injected with 3 mg/kg doxorubicin equivalents with dispersed 0.3% selective transport molecule liposomes (4 mice), the remaining aggregated 0.3% selective transport molecule liposomes (3 mice), untargeted liposomes (4 mice), and vehicle control (3 mice). This experiment confirmed that the dispersed liposomes were very effective as seen before and that all the therapeutic activity disappeared when the liposomes were aggregated (FIG. 19B). These results stress how important it is to measure any nanoparticle preparation and ensure that there is no aggregation as the effect could completely disappear.

Targeted Selective Transport Molecule Liposomes have Greater Therapeutic Effects than Uncleavable Selective Transport Molecule and Untargeted Liposomes The promising results attained with selective transport molecule targeted liposomes lead to testing of 2 more variables. The first was to further decrease the number of selective transport molecules on the surface and the second was to determine whether the enhanced therapeutic activity was selective transport molecule cleavage dependent or not. Liposomes were then remade with 0.1 and 0.3% selective transport molecule on the surface (approximately 9 and 27 selective transport molecules on the surface respectively) as an MMP cleavable peptide and an uncleavable peptide (Cy5-e$_9$-(Peg2)$_2$-r$_9$-c). The experimental group was increased to 8 mice per treatment and the experiment was performed by an independent contractor so as to eliminate any possible bias. Eight HT1080 tumor bearing mice with one tumor each were injected with 3 mg/kg equivalents of doxorubicin liposomes twice (day 8 and day 22) in order to further accentuate the differences between the drug formulations (FIG. 20A). Surprisingly the 0.1% selective transport molecule treatment was the most efficacious with this group showing more than a 4-fold reduction in average tumor volume compared with untargeted liposomes (at day 21 and 28). In addition to the cleavable selective transport molecule being superior to the untargeted liposome, the cleavable selective transport molecule was more efficacious than the uncleavable selective transport molecule. Compared to the similar loading number of selective transport molecules both sets of cleavable selective transport molecule liposomes resulted in smaller tumor volumes in mice than the uncleavable peptide and these differences were significant at multiple time points during the experiment (p-value <0.05) (FIG. 20B). By the end of the experiment mice in all treatment groups became sick and lost weight but there was no evidence that this was due to the drug treatments or that the selective transport molecule containing mice were any worse than untreated and vehicle control mice (FIG. 20C). Hematological analysis showed no significant differences between the groups except for the platelet count for the 0.1% cleavable and uncleavable mice being lower than the vehicle alone treatment group (data not shown).

Example 5: Screening for Carriers

Construct Synthesis.

Briefly, peptides were synthesized with a N-terminal thioacetamide and a C-terminal lysine. The lysine was used for conjugation to a Cy5 via an NHS ester, and the cysteine was used for conjugation to the indicated large molecular weight carrier via a maleimide linker. For the streptavidin conjugated molecules, peptides were synthesized with a biotin at the C-terminus that was used to directly conjugate four selective transport molecules to the streptavidin. With the exception of the PAMAM dendrimer-based constructs, constructs were purified by size exclusion HPLC, and purity was independently assessed by tricine gel electrophoresis. Some discrepancy was observed between the two techniques, possibly because of non specific sticking of free peptide to the large molecular weight carrier and possibly due to breakage of the maleimide linker. Efforts were made at further purification using electrophoretic techniques but this was largely ineffective. The PAMAM dendrimer-based constructs were purified by centrifugation through a membrane with a 10 kD molecular weight cut-off.

Imaging.

Animals expressing the polyoma middle T transgene (PyMT) driven by the MMTV promoter were obtained from Lesley Ellies. Nude animals bearing HT-1080 xenografts were either generated in house or were obtained from Explora Biosciences. Either way, tumors were used once they reached a diameter of 3-5 cm. Animals were anesthetized with ketamine/midazolam (80 mg/kg, 40 mg/kg) and injected with the indicated construct through the tail vein. Animals were typically observed throughout the first hour as they woke up from anesthesia. They were re-anesthetized and imaged at six hours, 12 hours, 24 hours and 48 hours as needed. After the last imaging session, animals were sacrificed by overdose of halothane. The imaging system used evolved over time. For most of the PEGylated conjugates, a simple light box was used, though the image shown is one of the first taken with the Maestro spectral deconvolution imager. The albumin, dextran and PAMAM dendrimer conjugates were tested using a 620/20 excitation filter and collecting images at 680 nm. The streptavidin conjugates were tested using a 640/48 excitation filter, with images collected at 700 nm.

Standardized Uptake Values.

Standardized Uptake Values were initially measured without tissue specific calibrations and were later re-adjusted to take tissue specificity and a light source change into account. Briefly, 30 mg of tissue was homogenized into SDS buffer (20 mM Tris pH 7.6, 1% SDS) as described previously. Tubes were frozen and imaged using the Maestro mouse imager (ex=either 620/20 or 640/48, em=680 nm or 700 nm). Calibrations were done separately for both sets of filters. Image analysis was done using Adobe Photoshop.

Histology.

Frozen sections were cut at 10 μm and analyzed using a fluorescence dissecting microscope (cy5: ex 620/60, em 640/48). Antibody stains were done on tissue fixed in iced acetone for 10 minutes using a FITC tagged F-480 antibody (blocked with 1N goat serum for 15 minutes, diluted into 1:50 into 1% goat serum in PBS, Caltag overnight 4° C.).

Magnetic Resonance Imaging.

Animals were anesthetized with isoflurane (induction 3%, maintenance 1-1.5%) and monitored while in the magnet using a respiratory monitoring system. Imaging was done using UCSD's 7T magnet using a GE interface. Several scans were done for each animal: a T1 weighted spin echo with fat saturation (Tr=400 ms, Te=8 ms, slice thickness 0.3 mm, matrix 512×512, 10 NEX), a T2 anatomical (Tr=3000 ms, Te=20 ms, slice thickness 0.3 mm, matrix 512×512), 1NEX, and a T1 series (Tr=150 ms, 250 ms, 500 ms, 1000 ms, 4000 ms, Te=12 ms).

Blood Halflife Increases with the Molecular Weight of the Carrier.

Figure 21:
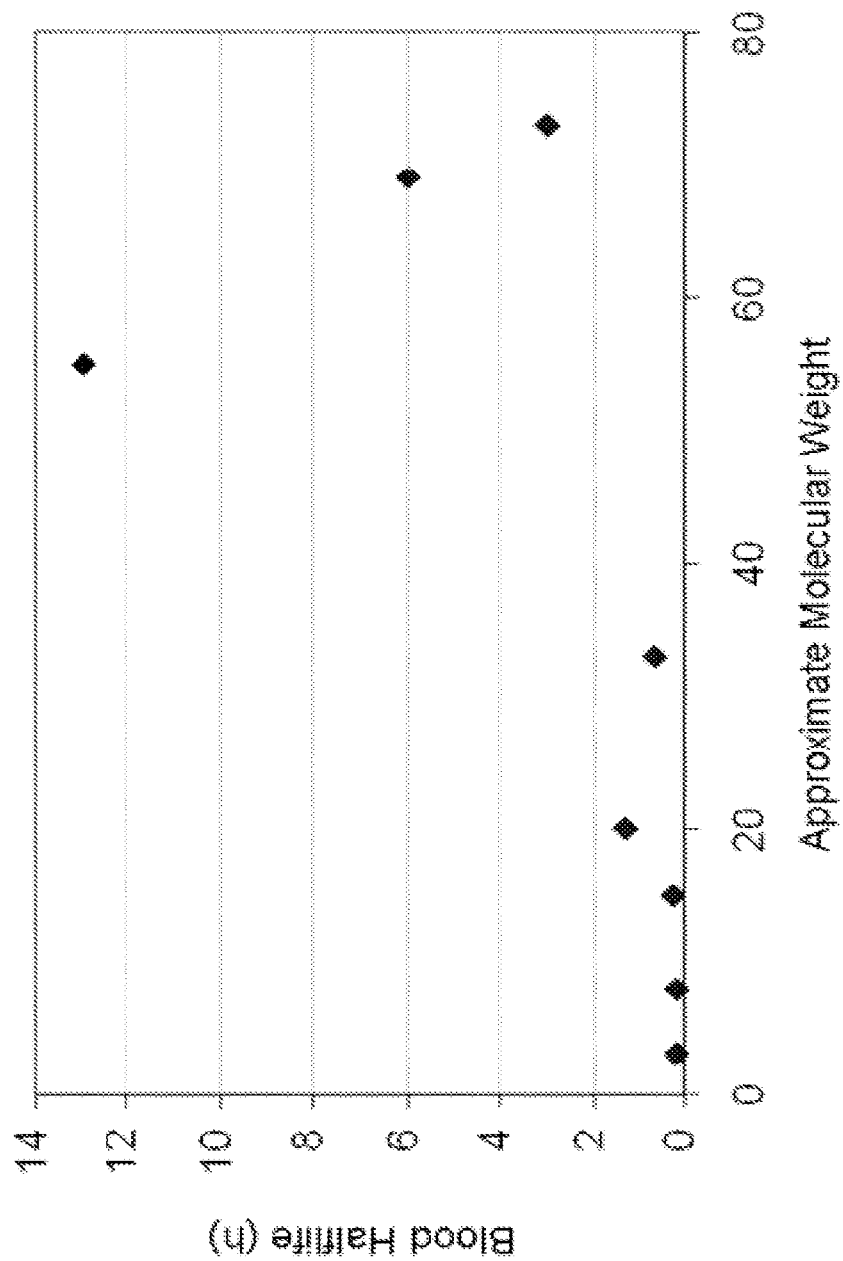
FIG. 21. Relationship between blood halflife and carrier size. Variation in molecules larger than 30 kD is due to the shape of the carrier (linear vs. globular).

As expected, blood halflife varied with the size of the carrier, ranging from a few minutes for the free peptides and 5 kD PEG conjugates to over 10 hours for selective transport molecules conjugated to PEG-4 capped $5^{th}$ generation PAMAM dendrimers. The dextran and albumin conjugates were in the middle, with blood halflives of 2-3 hours and 6-7 hours respectively. Since the large molecular weight conjugates typically contained free peptide as a major impurity, the plasma halflife measurement was typically started approximately 30 minutes post injection (FIG. 21).

At least two-fold differences in tumor uptake were observed between cleavable and uncleavable selective transport molecules attached to the same carrier.

Both albumin and dextran conjugates were synthesized using both cleavable and uncleavable selective transport molecules. For both carriers, approximately two-fold differences in uptake were seen at 48 hours (Table 3), indicating that selective transport molecules attached to carriers do get cleaved. Furthermore, gel electrophoresis indicated that the primary fluorescent species remaining in the tumor at 48 hours was the cleavage product.

TABLE 3

| Peptide Structure | Approx Purity by gel | Dose/Time at Sacrifice | Approx Plasma Halflife | Tumor Uptake (SUV) (mean ± SD) | Liver Uptake (SUV) (mean ± SD) | Kidney Uptake (SUV) (mean ± SD) |
|---|---|---|---|---|---|---|
| 12kD-PEG-$e_9$-XPLGLAG-$r_9$-k(cy5) | >90% | 6 nmol 1 h | 20 m | 0.51 ± 0.13 (n = 7) | 1.58 ± 0.79 (n = 7) | 3.38 ± 1.33 (n = 7) |
| 12kD PEG-$e_9$-Xplglag-$r_9$-k(cy5) | >90% | 6 nmol 1 h | NA | 0.26 ± 0.09 (n = 4) | 2.52 ± 0.65 (n = 4) | 7.10 ± 2.38 (n = 4) |
| 12kD-PEG-$e_9$-XPLGLAG-$r_9$-k(cy5) | >90% | 6 nmol 1 h | NA | 0.68 ± 0.17 (n = 2) | 1.17 ± 0.49 (n = 2) | 5.33 ± 0.64 (n = 2) |
| 12kD PEG-$e_9$-Xplglag-$r_9$-k(cy5) | >90% | 6 nmol 1 h | NA | 0.31 + 0.18 (n = 2) | 0.71 ± 0.17 (n = 2) | 3.27 ± 0.62 (n = 2) |
| Alb-$e_9$-XPLGLAG-$r_9$-k(cy5) | ~60% | 4.8 nmol 48 h | 3 h | 0.9 ± 0.3 (n = 2) | 8.3 ± 2.9 (n = 2) | 2.8 ± 1.0 (n = 2) |
| Alb-$e_9$-Xplglag-$r_9$k(cy5) | ~40% | 6 nmol 48 h | NA | 0.2 ± 0.1 (n = 2) | 11.8 ± 1.1 (n = 2) | 5.4 ± 0.2 (n = 2) |
| Dex-$e_9$-XPLGLAG-$r_9$-k(cy5) | Not assessed | 5 nmol 48 h | 6 h | 2.3 ± 2.0 (n = 2) | 14.2 ± 7.1 (n = 2) | 3.3 ± 1.9 (n = 2) |
| Dex-$e_9$-Xplglag-$r_9$-k(cy5) | Not assessed | 6 nmol 48 h | NA | 0.5 ± 0.2 (n = 2) | 11.1 ± 1.5 (n = 2) | 6.1 ± 0.5 (n = 2) |
| Streptavidin[$e_9$-XPLGLAG-$r_9$-k(cy5)]$_4$ | Not assessed | 4 nmol 48 h | 4 h | 0.4 ± 0.0 (n = 2) | 3.2 ± 0.0 (n = 2) | 3.7 ± 1.0 (n = 2) |
| G5 PAMAM[$e_9$-XPLGLAX-$r_9$-k(cy5)]$_2$[Succ]$_{126}$ | 60% | 3 nmol 24 h | NA | 1.4 ± 0.4 (n = 2) | 6.6 ± 2.1 (n = 2) | 1.8 ± 0.4 (n = 2) |

TABLE 3-continued

| Peptide Structure | Approx Purity by gel | Dose/Time at Sacrifice | Approx Plasma Halflife | Tumor Uptake (SUV) (mean ± SD) | Liver Uptake (SUV) (mean ± SD) | Kidney Uptake (SUV) (mean ± SD) |
|---|---|---|---|---|---|---|
| G5-PAMAM4-[e$_9$-XPLGLAX-r$_9$-k(cy5)]$_2$[PEG]$_{126}$ | >90% | 3 nmol 24 h | 20 h | 1.2 ± 0.1 (n = 3) | 4.1 ± 0.7 (n = 3) | 2.0 ± 0.2 (n = 3) |
| G5PAMAM4e$_9$-[XPLGLAX-r$_9$-k(cy5)]$_2$[PEG]$_{126}$ | >90% | 3 nmol 48 h | NA | 1.36 ± 0.13 (n = 3) | 5.89 ± 0.55 (n = 3) | 2.09 ± 0.34 (n = 3) |
| G5PAMAM[e$_9$-XPLGLAG-r$_9$-k(cy5)][PEG]$_{127}$ | >90% | 3 nmol 48 h | NA | 0.6 ± 0.1 (0.5, 0.7) n = 2 | 3.5 ± 1.7 (2.3, 4.7) n = 2 | 1.1 ± 0.0 (1.1, 1.1) n = 2 |
| G5PAMAM-[e$_9$-OPLG(MeC)AG-r$_9$-k(cy5)] [PEG]$_{127}$] | >90% | 3 nmol 48 h | | 0.71 ± 0.5 (0.2-1.2) n = 3 | 1.8 ± 0.8 (0.9-2.3) n = 3 | 1.3 ± 0.4 (1.0-1.7) n = 3 |

Carrier Attached Cleavable Selective Transport Molecules Appear to Largely be Taken Up by MMP-2 Producing Tumor Stroma when Examined Histologically.

Like the free peptides, uptake of shrapnel based peptide conjugates was localized to stroma in transgenic mice harboring the polyoma middle T antigen driven by the MMTV promoter. Antibody stains showed this stromal uptake to colocalize to the presence of MMP-2. In some animals, particularly of the iNOS−/− genotype, MMP-9 expressing regions of squamous metaplasia were highlighted, particularly with the albumin conjugated probes. These regions were confirmed to contain active MMP by in situ zymography.

Cleavable Selective Transport Molecules are Cleaved by Macrophages in Sentinel Lymph Nodes.

Figure 22:
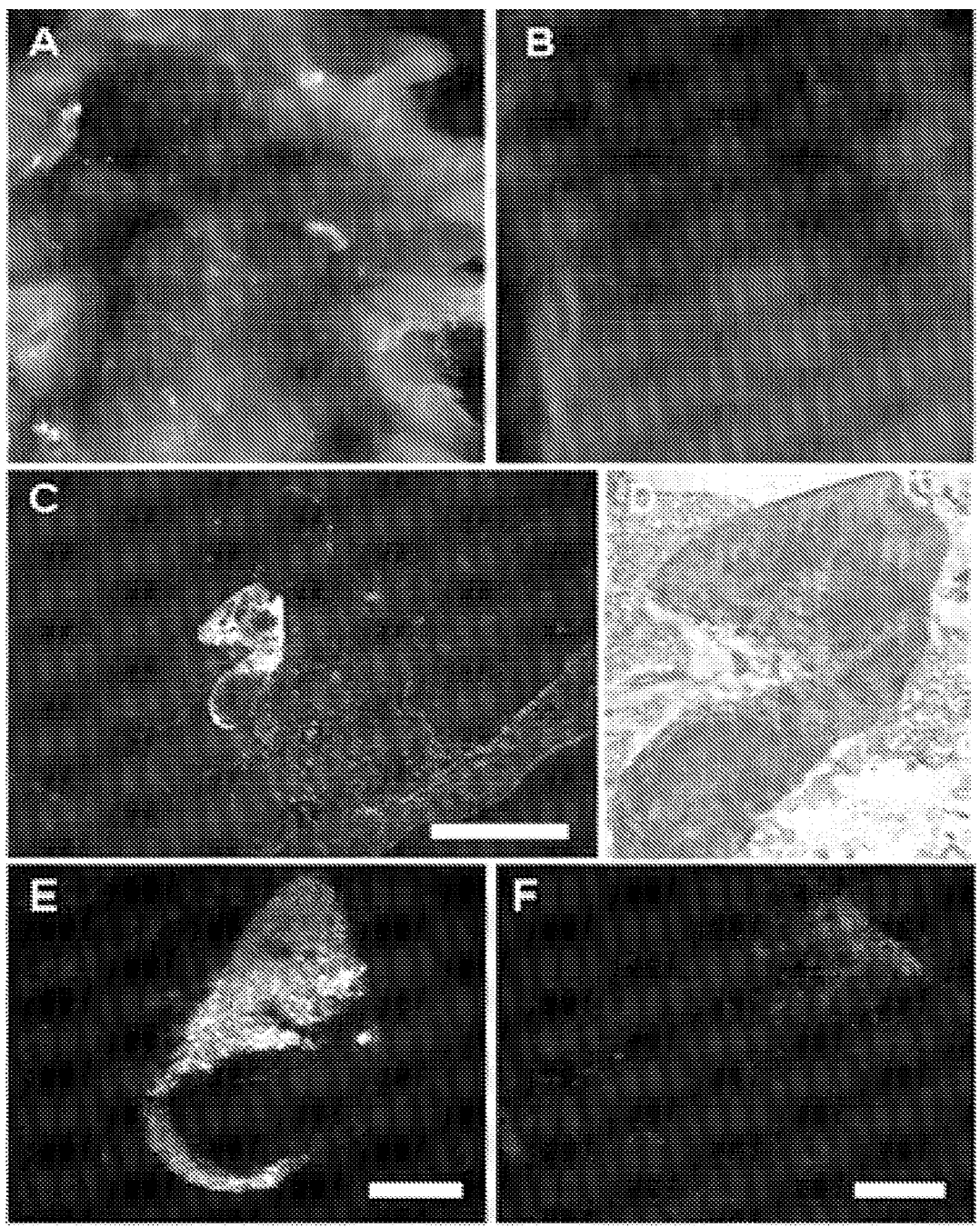
FIG. 22. Lymph node uptake is both tumor and cleavage dependent. Gross images of exposed lymph nodes from a tumor bearing mouse (A) and a non tumor bearing mouse (B), 48 hours post injection with dextran cleavable selective transport molecule are shown. The identity of such structures was confirmed by frozen section histology (C) and (D) Scale bar=1 mm. (E) and (F) show lymph nodes from mice 48 h post injection with cleavable (E) and uncleavable (F) dextran conjugated peptides. Scale bar=200 µm.
Figure 23:
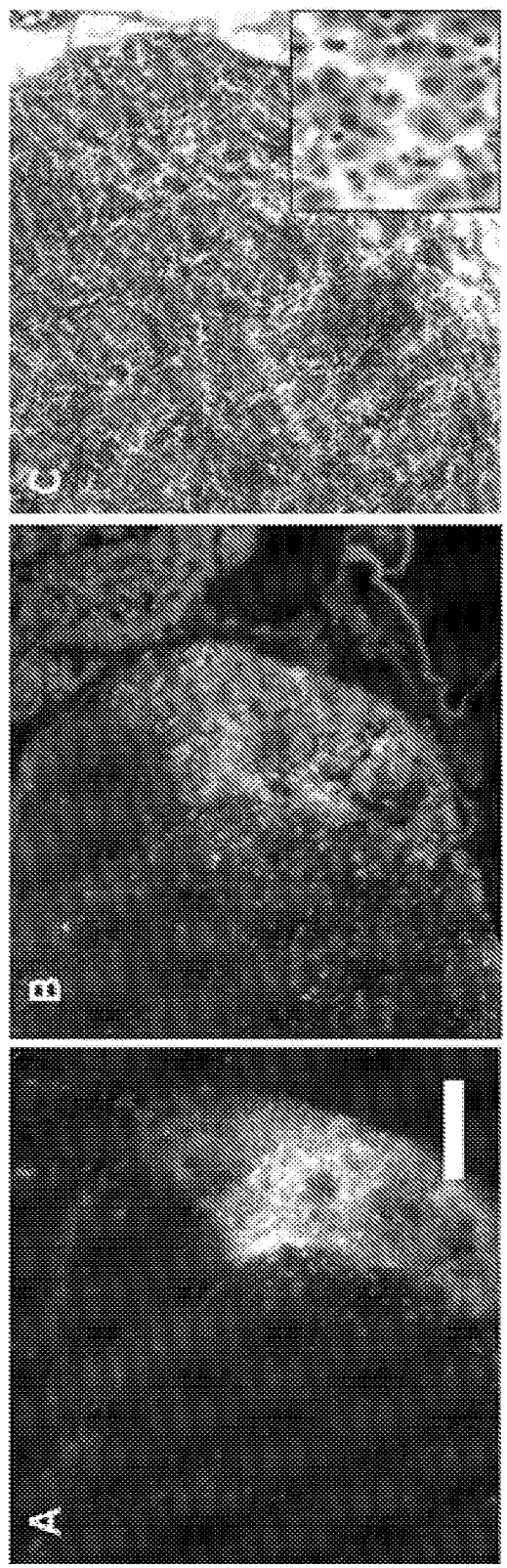
FIG. 23. Lymph node staining is confined to F4/80 producing phagocytes. (A) shows a close-up cy5 image of a lymph node. (B) shows a serial section stained with a FITC-tagged antibody against F4/80. (C) shows a serial section stained with hematoxylin and eosin. The inset shows cell morphology from a brightly staining area. Scale bar=200 µm.

An early observation made with selective transport molecules attached to large molecular weight carriers via the polyglutamate is that there is uptake in the lymph nodes of immunocompetent mice after 48 hours. So far, this has been observed for 5$^{th}$ generation PAMAM dendrimers as well as 70 kD dextrans, streptavidin and albumin. Tumor uptake in PyMT mice was reduced in animals injected with an all-d-amino acid control peptide (FIG. 22). It also occurred to a much lesser extent in non tumor-bearing animals, suggesting that it is a tumor dependent process. Cleavage of peptide likely occurs in the lymph nodes themselves, since subcutaneous co-injection with r9-FITC and e9-XPLGLAG-r9-cy5 did not lead to co-staining in the lymph node. Animals with generalized active inflammation due to pre-injection with Freund's complete adjuvant took up peptide in a manner similar to animals with tumors, suggesting that uptake has to do with activated macrophages in lymph nodes activating selective transport molecules. Finally there is more overall uptake in sentinel lymph nodes in animals with invasion into the lymph node than in animals without, but uptake colocalizes to F-480 expressing macrophages, so it is possible that this is simply due to more activation of macrophages in the presence of invasive tumor (FIG. 23).

PEG (5 kD and 12 kD)

Figure 24:
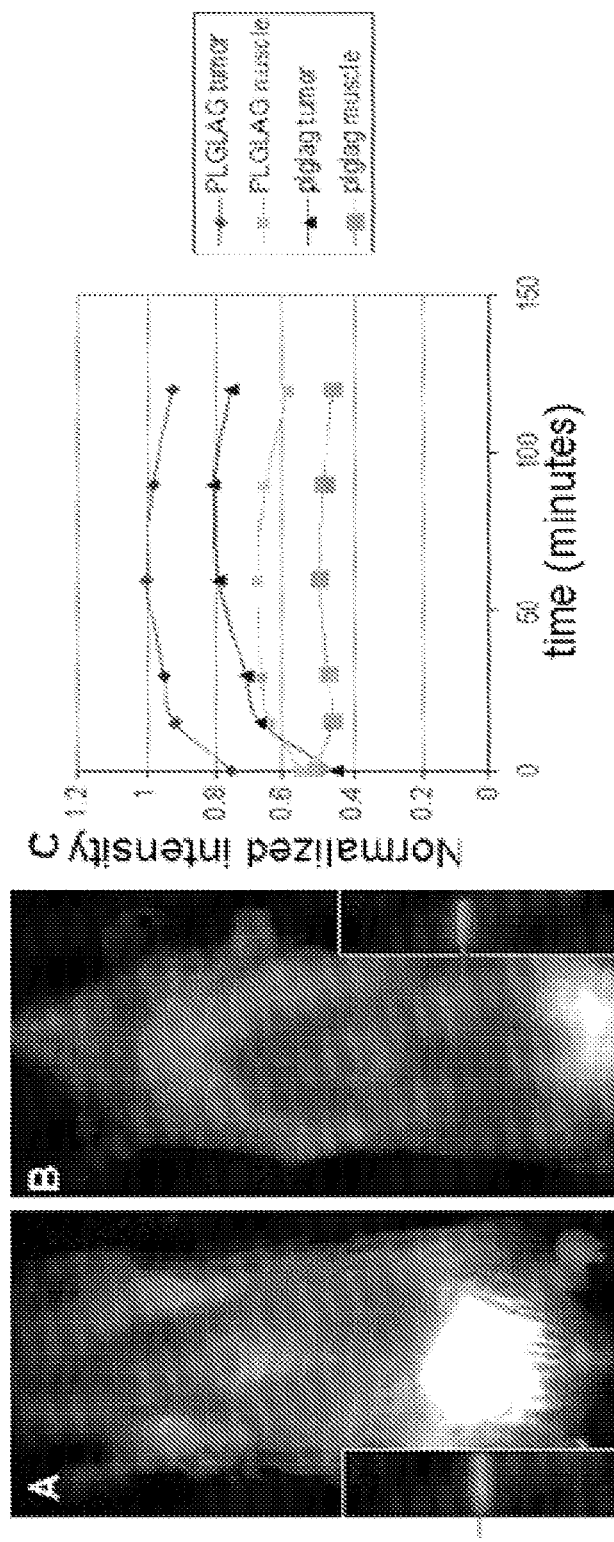
FIG. 24. Peptides conjugated to PEG-12 kD. (A) shows a mouse two hours following injection with 4.8 nmol cleavable peptide conjugated to PEG-12. Insets show analytical gels demonstrating purity of the construct injected. (B) shows the same for the uncleavable d-amino acid peptide. (C) shows relative intensities of the indicated regions over time.

Peptides conjugated to 5 kD PEG and 12 kD PEG were injected into nude mice bearing HT-1080 xenografts at a dose of 6 nmoles per animal (FIG. 24). In general, 5 kD PEG conjugates behaved similarly to free peptides, with a blood halflife of around five minutes, while 12 kD PEG conjugates had a longer halflife of approximately 20 minutes. As controls, a scrambled version of the PLGLAG (SEQ ID NO: 1) cleavable sequence denoted as LALGPG (SEQ ID NO: 48) and a d-amino acid version of the PLGLAG (SEQ ID NO: 1) sequence denoted as plglag were also injected. The two negative controls gave similar standardized uptake values in HT-1080 xenografts, but we decided to use the d-amino acid version for future experiments. Because of what was what was available at the time, the polyoma transgenic mice were tested in wildtype and iNOS−/− backgrounds. The uptake values shown below for PyMT mice pool both types of animals since the values obtained were not significantly different. These data were originally processed using calibrations from just liver and kidney tissue, since we were unaware of the need for tissue specific calibrations at the time. The data shown in Table 3 for PEGylated peptides have undergone a post-hoc tissue specific calibration, with tumor values being decreased by a factor of two and spleen values increasing by a factor of two, rendering these data more or less comparable to the other data collected using the Maestro. The liver and kidney both show decreased uptake relative to the free peptides; this is likely due to about 50% of the injected peptide undergoing urinary excretion by one hour.

Following the initial experiment with PEGylated peptides, several variations were tested. An ESPAYYTA (SEQ ID NO: 4) cleavage sequence for MMP-2 identified by phage display did not lead to an improvement in tumor uptake but led to increased uptake in the liver. A PLGWAG (SEQ ID NO: 49) sequence also led to a decrease in tumor uptake and an increase in liver uptake, as did an XSGRSAX (SEQ ID NO: 50) sequence for uPA. Giving the molecule an overall negative charge caused faster washout from all organs including tumor. Preinjection of metalloproteinase and metallopeptidase inhibitors such as thiorphan and actinonin decreased kidney uptake by up to 50%, suggesting that in these organs uptake is cleavage dependent. The presence of gelatin cleaving entities in these other organs was confirmed by zymogram gel. As expected, tumor uptake also decreased upon injection with inhibitor.

Albumin

Figure 25:
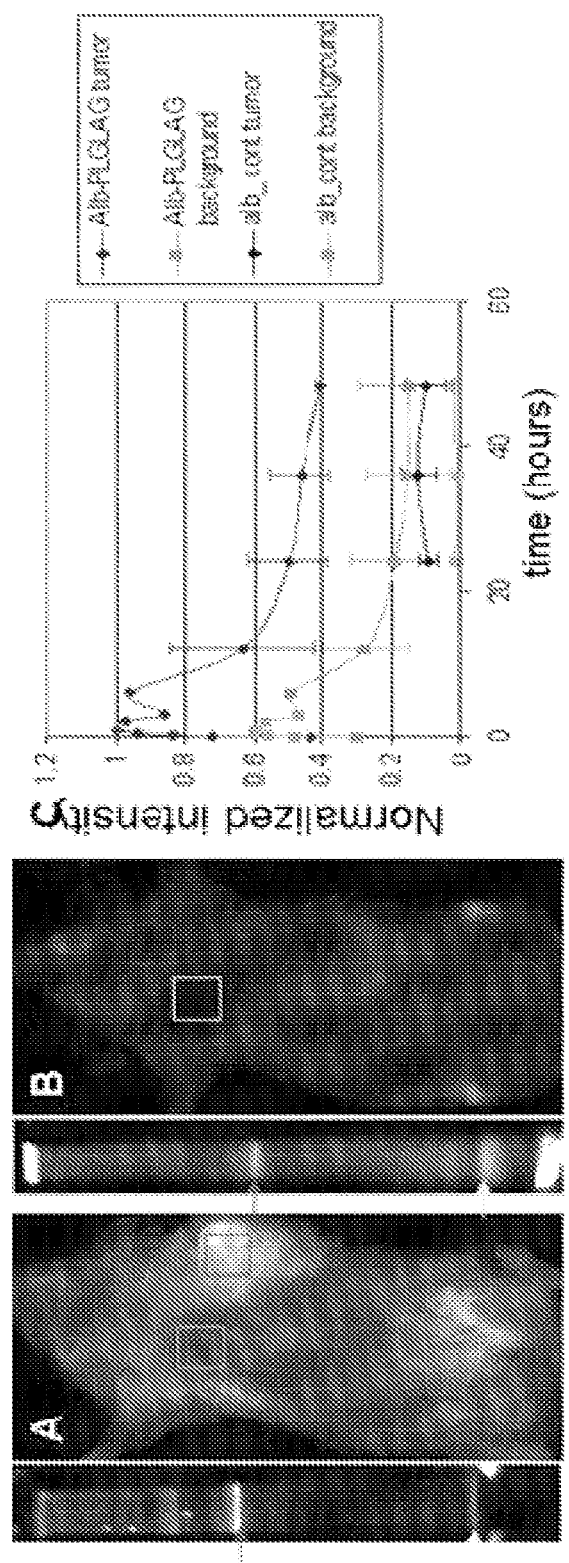
FIG. 25. Peptides conjugated to albumin. (A) Analytical gel showing injectate purity and mouse 36 hours following injection with 4.5 nmol cleavable peptide conjugated to albumin. (B) shows the same for the uncleavable d-amino acid peptide. (C) shows normalized intensities of the indicated regions over time.

The MMP cleavable selective transport molecule and its all-d-amino acid control peptide were next conjugated to albumin (FIG. 25), a protein that is excluded from the glomerular filtrate under normal physiological conditions. Although peptides appeared to be pure by HPLC, gel electrophoresis indicated that as much as 50% of the cy5 may have been attached to impurities. Nevertheless, these peptides were tested exclusively in polyoma mice in a nNOS−/− background. The genetic background was chosen based on what was immediately available at the time, but when tumors from nNOS−/− and wildtype mice were compared later on a zymogram gel, tumor MMP activation was did not differ significantly. Animals were sacrificed 48 hours post injection with four to six nmol peptide, although maximal tumor to skin contrast occurred at around 36 h.

Similarly to the PEGylated peptides, calibrations for the albumin peptides were originally done using only liver and kidney standards and post-hoc adjustments had to be made for comparison with other peptides. Albumin was one of the better carriers tested; however the chemical synthetic procedure at the time required a heating step to insert gadolinium into the DOTA chelator. Since albumin is a protein, this heating step would have denatured it, limiting its potential for designing T1 MRI agents.

Dextran

Figure 26:
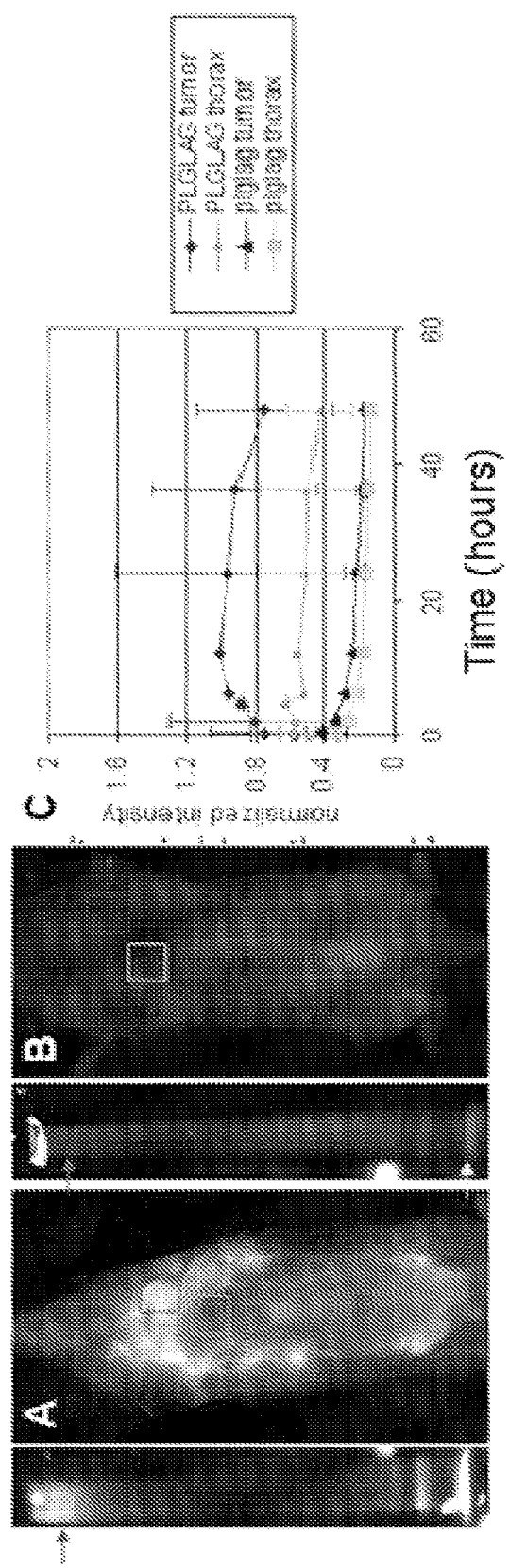
FIG. 26. Peptides conjugated to 70 kD dextran. (A) shows mice 36 hours following injection with 6 nmol cleavable peptide conjugated to 70 kD dextran. Analytical gels of injectates are shown to the left of each mouse. Dark arrows indicate what is believed to be desired product; light arrows indicate free peptide. (B) shows the same for the uncleavable d-amino acid peptide. (C) shows normalized intensities of the indicated regions over time.

The MMP cleavable and all-d-amino acid control peptides were next conjugated to 70 kD dextrans and tested in PyMT mice in a wildtype background. Although several attempts at synthesizing the dextrans were made, purification was done via a retention time cut-off on HPLC. When the samples were analyzed by electrophoresis, it was unclear that the synthesis was reliable. Typically there was a smear at the top of the gel (purple arrow), a species that runs similarly to free peptide at the bottom of the gel (green arrow) and a species that is roughly twice as large as free peptide (pink arrows). Each of the syntheses appeared to contain the same three components, albeit in different ratios. The best mouse images came from batches in which the high molecular weight species dominated, as shown in FIG. 26. A subsequent indium labeled version containing mostly the middle turquoise species did not cleave well in vitro with MMP-9, and the lower molecular weight species is likely unattached free peptide. The uptake values shown in Table 3 were done with the first batch of PLGLAG (SEQ ID NO: 1) and plglag.

Streptavidin.

A third carrier tested was streptavidin. In this scheme, biotinylated peptides could be easily attached to streptavidin, thereby greatly facilitating construct synthesis. The SUV's were disappointing however, and precipitation in the injectate was extremely problematic probably due to precipitation of the biotinylated selective transport molecules.

5$^{th}$ Generation PAMAM Dendrimers.

Figure 27:
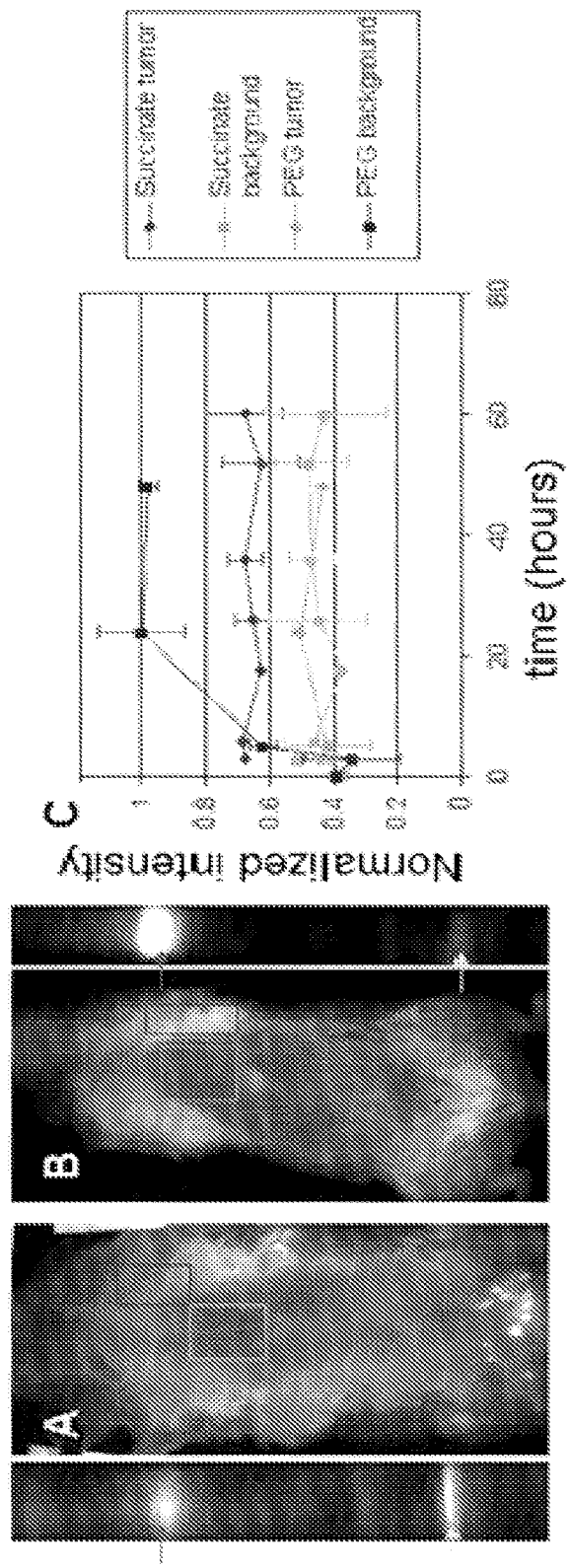
FIG. 27. Peptides conjugated to PAMAM dendrimers. (A) shows a mouse 36 hours following injection with 4.5 nmol cleavable (PLGLAX (SEQ ID NO: 2)) peptide conjugated to a 5th generation succinyl capped PAMAM dendrimer. Analytical gels of injectates are shown to the left of each mouse. Dark arrows indicate desired product; light arrows indicate free peptide. (B) shows the same for a similar dendrimer capped with PEG-4. (C) shows normalized intensities of the indicated regions over time. Note that the first images were taken with orange filters and the second were taken with red filters.

As the last molecule in the large molecular weight carrier series, 1725 was a fifth generation PAMAM dendrimer conjugated to two MMP cleavable selective transport molecules. The remaining 126 attachment sites were capped with succinyl groups. More pure than most of its predecessors (60% by gel electrophoresis with the major impurity running as free peptide), it appeared to have a biphasic blood halflife with the first phase on the order of under 10 minutes and the second on the order of 10-15 hours. The peptide appeared to accumulate in tumor for up to 72 hours (FIG. 27), with tricine gel electrophoresis indicating that most peptide present in tumor at that time was cleaved. Because of the relative ease in synthesis and promising in vivo characteristics, the Generation 5 PAMAM-(e9-XPLGLAX-r9-k(cy5))$_2$(succ)$_{126}$ was resynthesized. As usual, HPLC analysis indicated the molecules were pure, though gel electrophoresis revealed the presence of free peptide in the injectate. Efforts to purify the sample further using various electrophoretic techniques and salt concentrations were unsuccessful. This molecule was injected into both HT-1080 tumor bearing nude transgenic PyMT mice at varying concentrations. Although SUV's went up at lower concentrations, our ability to detect the molecule went down. The best concentrations to use appeared to be either 3 nmol injectate or 1.5 nmol injectate, and animals were sacrificed after 24 hours. Gel electrophoresis indicated that most of the peptide present in the tumors and organs was cleaved, with no identifiable starting material present in any organ.

Testing Faster Cleaving Sequences on Succinylated PAMAM Dendrimers

To test the effect of using a faster cleaving sequence, two dendrimers were synthesized with succinate caps. The first made use of the standard MMP sequence PLGLAX (SEQ ID NO: 51), and the second contained a similar sequence in which L was replaced by a thienylalanine (ThA) residue in the P1 site. This variation caused liver uptake to increase by a factor of two, and the tumor uptake to decrease by a factor of 2.5.

Testing PEGylated PAMAM Dendrimers and their Variants.

Figure 28:
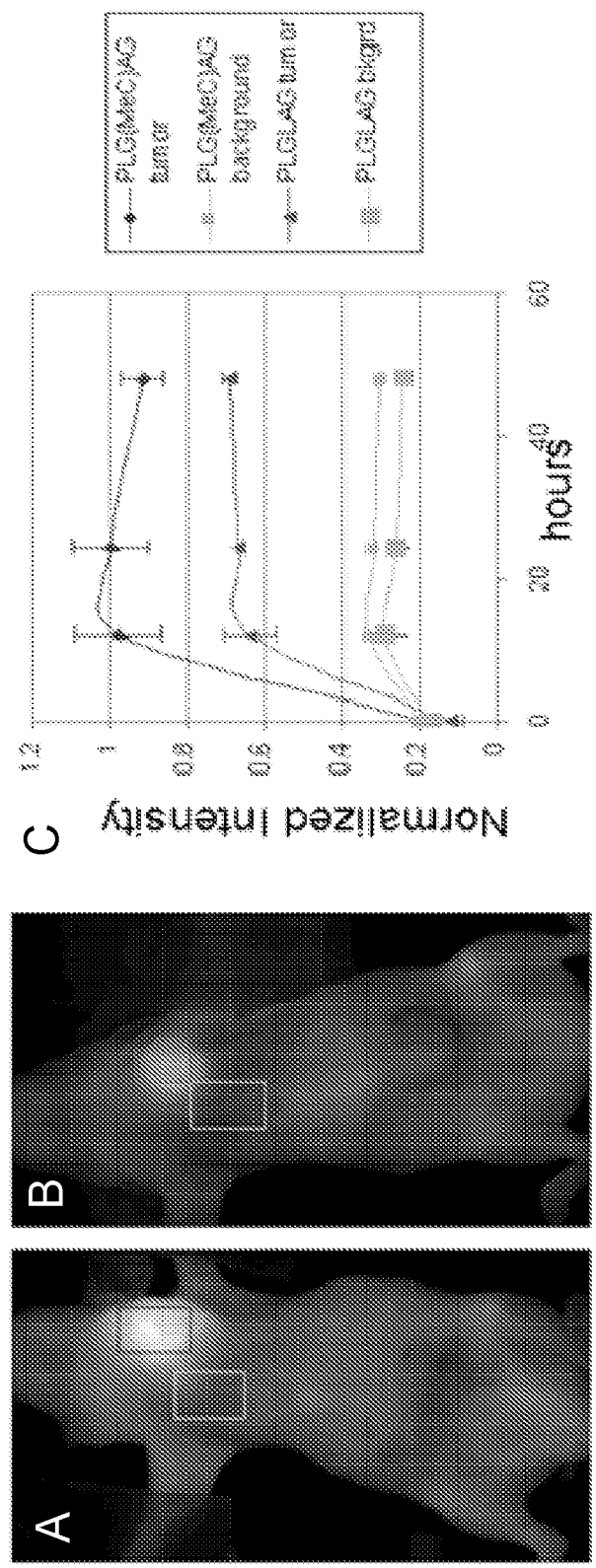
FIG. 28. A faster cleaving sequence increases uptake for selective transport molecules capped with PEG-4. (A) Analytical gel showing injectate purity and mice 48 hours following injection with 3 nmol cleavable (PLG(MeC)AG (SEQ ID NO: 3)) peptide conjugated to a 5th generation PEG-4 capped PAMAM dendrimer. Dark arrows indicate desired product; light arrows indicate free peptide. (B) shows the same for a similar construct using PLGLAG (SEQ ID NO: 1) as a cleavage sequence. (C) shows normalized intensities of the indicated regions over time.

In a separate experiment, PLGLAX (SEQ ID NO: 51) was compared to PLGLAG (SEQ ID NO: 1) and PLG-C(me)-AG (SEQ ID NO: 3) with a PEG-4 cap. These molecules were approximately 90% pure by gel electrophoresis. Using the PLGLAG (SEQ ID NO: 1) sequence appeared to cause decreased tumor uptake relative to PLGLAX (SEQ ID NO: 51), with similar liver uptake. Replacing the leucine with methylcysteine (MeC) caused the liver uptake to decrease by a factor of two, with tumor uptake similar to that of PLGLAX (SEQ ID NO: 51). Tumor uptake remained the same between PLGLAX (SEQ ID NO: 51) and PLG-C(me)-AG (SEQ ID NO: 3), but liver uptake decreased by a factor of two. PLG-C(me)-AG (SEQ ID NO: 3) was therefore taken to be a superior substrate for use on large molecular weight carriers (FIG. 28).

Testing Dextran-Conjugated Selective Transport Molecules Using T1-MRI.

Finally, to test whether carrier-attached selective transport molecules could deliver sufficient cargo to be visible using MII when injected in large doses, several versions of a dextran conjugated gadolinium-labeled selective transport molecule were synthesized. Dextran was chosen because it was the carrier with the highest uptake that was able to withstand the heating step necessary to insert gadolinium into a DOTA chelating group. These molecules were then injected into animals and were imaged using a 7T MRI scanner. T$_1$ values for several tissues were calculated by taking images at several relaxation times while holding the echo time constant. Average signal for tumor and muscle was determined by averaging the intensity over a tumor volume using Amira software. Using this strategy, we found the T1 value of a water phantom at 7T to be 2.6±0.4 s (n=21), compared to a literature value of approximately 3 s. The discrepancy could be due to the presence of ions in the water, which is possible since this water was not doubly distilled and was primarily being used to determine the stability of the magnet over time. Since the scanner was somewhat inconsistent over time, frequently crashing in the middle of an experiment, for each day we normalized the T1 value for the tumor to the T1 value for the water phantom. Intensity values computed from fat saturated images were treated similarly.

Figure 29:
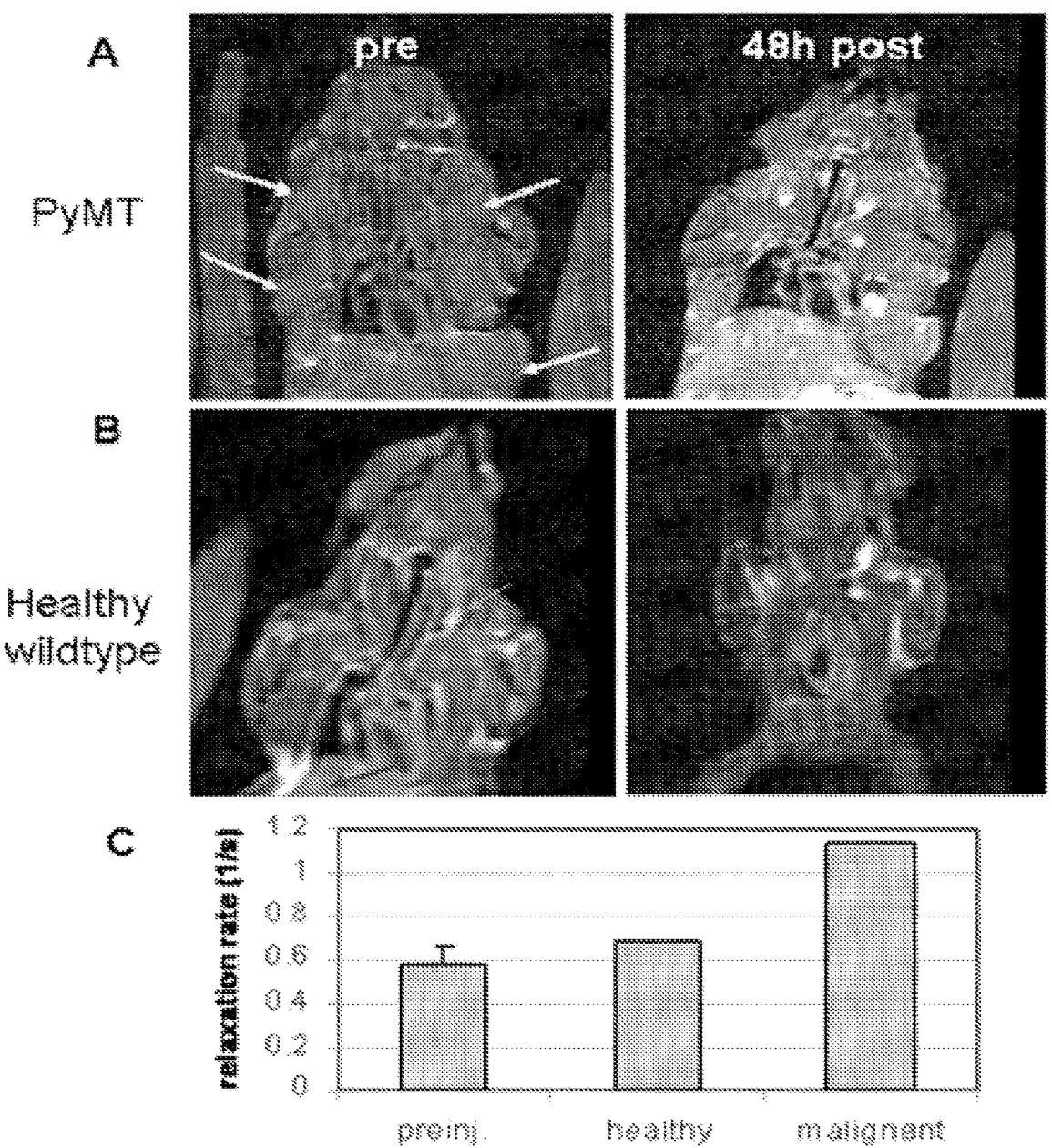
FIG. 29. T1-MRI imaging of an animal after injection of a selective transport molecule—conjugated dextran. (A) shows a PyMT mouse pre and 48 hours post injection of contrast. Note there is no significant difference in tumor to phantom ratio after injection with contrast. (B) shows a wildtype mouse pre and 48 hours post injection of contrast. (C) shows the relaxation rate over putative cervical lymph node regions in uninjected, wildtype and PyMT injected mice.

Four batches of dextran conjugates were tested for MR imaging, with four different outcomes. The first batch (1746) barely got taken up by tumors but did appear to be taken up by sentinel lymph nodes. Quantitatively, there was typically less than 1 nmol/g probe in tumor after 48 h, but due to the apparent presence of probe in the lymph nodes (FIG. 29), the probe was resynthesized with 4 selective transport molecules attached to each dextran. This peptide (1810) was injected into mice and gave maximal tumor uptake of 3nmol/g. T1's were not taken for either of these molecules due to technical difficulties with the scanner. Unlike the previous peptide, this peptide was also radiolabeled with indium-111. The third dextran-based optical construct, 1921, was examined by T1 both before and after injection of contrast. By this analysis, the presence of gadolinium in tumor should correlate with an increase in tumor intensity on a T1-weighted image and a decrease in tumor T1. Unfortunately, gadolinium uptake in tumors was less than 1 nmol/g, and correlated with little if any change in tumor T1. Finally, a fourth dextran conjugate was made, termed 2024. With no imaging data collected, tumor uptake was again approximately 1 nmol/g, though lymph node uptake was higher than the detection limit of 10 nmol/g. Although this to some extent validated our original observation, at this point, the dextran-based shrapnel peptides were abandoned as a candidate for MR imaging due to low tumor uptake and high batch-to-batch inconsistency.

Example 6: Capping of Carriers

Figure 30:
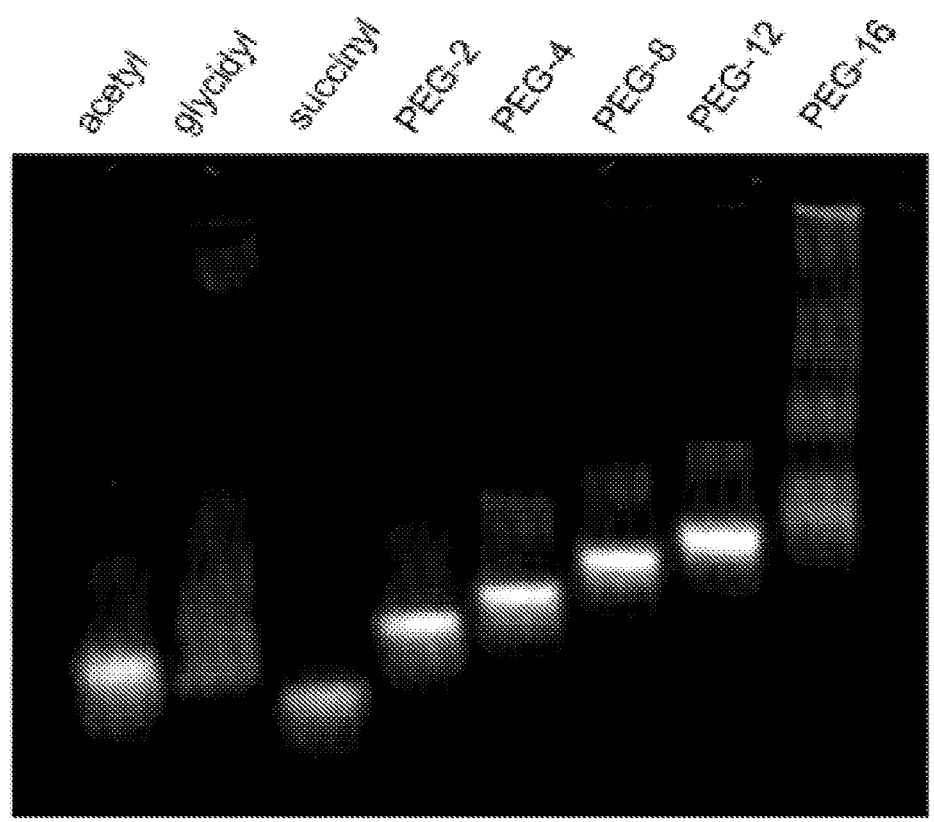
FIG. 30. Purity gel for PAMAM constructs. The glycidyl and PEG-16 constructs were deemed to be unacceptable for injection into animals using this method.
Figure 31:
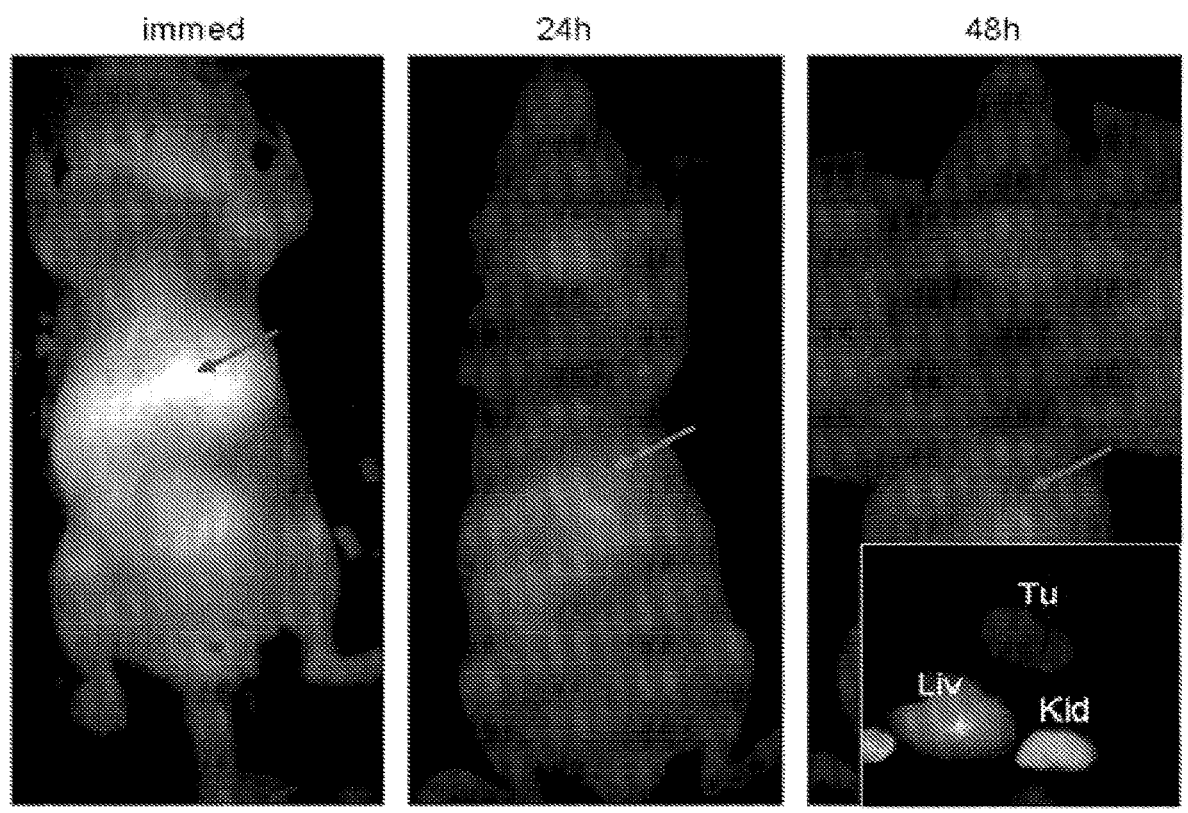
FIG. 31. In vivo time course for a mouse injected with a sulfobenzoyl-capped compound. The inset shows fluorescence images of harvested organs.

This example explore the effect of capping groups on the pharmacokinetics of dendrimers. Here, we have tested the effect of capping using several different capping groups on plasma halflife, tumor uptake and tumor penetration in mice.
Animals.
Two types of animals were used in these experiments. Athymic nude mice bearing HT-1080 xenografts approximately 5-7 mm in size at the time of injection and (b) PyMT mice.
Determination of Plasma Halflife
To obtain approximate plasma halflives, approximately 10 µL of blood was collected in a heparinized capillary tube at 30 minutes and, 1, 2 and 6 hour time points. The blood was imaged on the Maestro, and intensities were calculated using Image J. Intensities were linearized by taking the natural logarithm; plasma halflife=0.693/m where m is the slope of the line.
Results and Discussion
We first tested molecules with "pure" caps, including acetyl, succinyl, 3-hydroxypropionyl, 2-sulfobenzoyl, glycidyl, PEG-2, PEG-4, PEG-8 and PEG-12. The molecules were purified using HPLC and purity was verified by tricine gel electrophoresis (FIG. 30). Upon injection into animals, the probes followed one of several patterns. Some, including 3-hydroxypropionyl, 2-sulfobenzoyl, and glycidol, are rapidly cleared from the bloodstream during the first five minutes post injection (FIG. 31). For these molecules, uptake is largely hepatic, and they are cleared to a varying degree over the next 48 hours. To a lesser degree, they are also taken up by kidney, salivary gland and to a limited extent, tumor.

Figure 32:
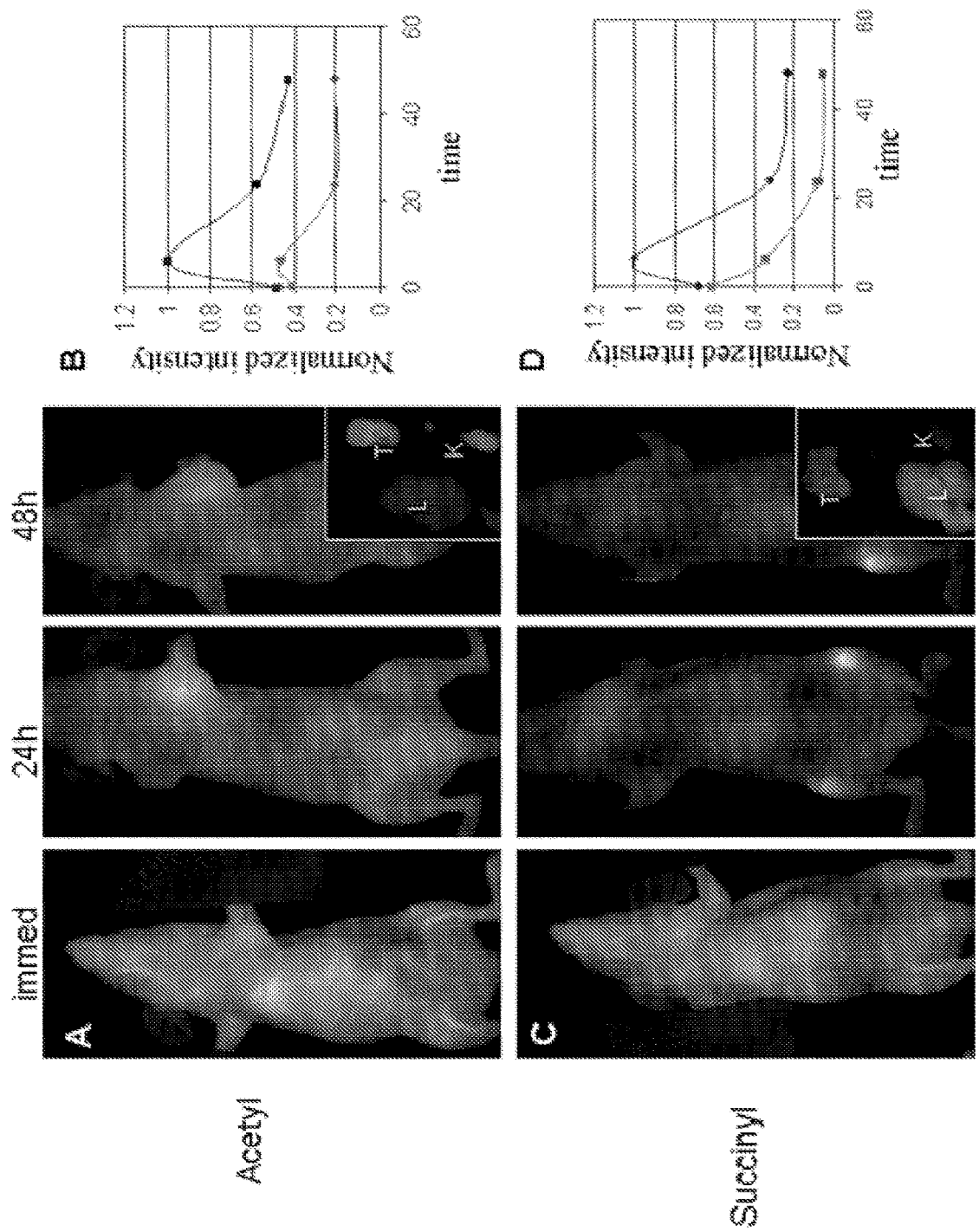
FIG. 32. In vivo images for mice injected with acetyl and succinyl capped dendrimers. (A) shows images of a mouse immediately post, 24 h post and 48 hours post injection with an acetyl capped dendrimer. Fluorescence dissection images are shown and labeled T (tumor), L (liver) and K (kidney).

A second pattern was observed for the succinyl and acetyl capped compounds. These molecules are small enough that they are still excreted renally. At physiological pH, succinyl-capped dendrimers are highly negatively charged, with a plasma halflife of 3.2±0.9 hours in animals. At 48 hours post injection, accumulation was largely in the joints, liver and kidney. In contrast, acetyl capped dendrimers are neutrally charged and have more favorable pharmacokinetic properties, with an average plasma halflife of 5.6±2.5 hours. At 48 hours, the acetyl capped dendrimers did not show any obvious tissue specific accumulation. Excretion for the succinyl and acetyl capped dendrimers is partially hepatobiliary and partially renal. Images for each of these dendrimers immediately post injection, 24 hours post injection and 48 hours post injection are shown in FIG. 32.

A third uptake pattern occurred for dendrimers coated with different length polyethylene glycol moieties. The PEG-2 and PEG-4 dendrimers were excreted with a plasma halflife of 8.4±1.3 hours and 13.9±2.9 hours respectively, but some bladder fluorescence was observed at early time points so there may have been limited renal excretion. The PEG-8 and PEG-12 coated dendrimers had blood halflives of 13.9±2.9 hours, 11.6±1.6 hours and 18.1±3.7 hours respectively. All of these dendrimers had more intrinsic tumor targeting than the succinyl and acetyl capped molecules, with standardized uptake values in tumor being approximately two fold greater in liver than in tumor (Table 5). This was readily apparent in the images, with tumor accumulation increasing slowly over time (FIG. 33).

TABLE 5

| | Tumor (HT-1080) SUV | Liver SUV | Kidney SUV | Muscle SUV | Plasma Halflife (h) (mixed N/P) |
|---|---|---|---|---|---|
| G4-PAMAM-PEG-$8_{128}$ | 0.4 ± 0.2 (0.2-0.7) n = 3 | 0.8 ± 0.2 (0.6-1.0) n = 3 | 0.4 ± 0.0 (0.4-0.4) n = 3 | 0.1 ± 0.0 (0.1-0.1) n = 3 | 9.9 ± 1.2 (8.0-11.3) n = 5 |
| G5-PAMAM-Acetyl$_{128}$ | 0.8 ± 0.5 (0.3-1.2) n = 3 | 2.1 ± 0.5 (0.8-2.7) n = 3 | 1.7 ± 0.7 (1.0-2.3) n = 3 | 0.2 ± 0.0 (0.2-0.3) n = 3 | 5.6 ± 2.5 (2.4-8.0) n = 5 |
| G5-PAMAM-Succinyl$_{128}$ | 0.7 ± 0.3 (0.4-0.9) n = 3 | 7.8 ± 2.0 (6.1-10.0) n = 3 | 0.4 ± 0.2 (0.2-0.5) n = 3 | 0.1 ± 0.1 (0.1-0.2) n = 3 | 3.2 ± 0.9 (1.8-4.3) n = 5 |
| G5-PAMAM-Hydroxypropanyl$_{128}$ | NA | NA | NA | NA | >5 m |
| G5-PAMAM-Sulfobenzoyl$_{128}$ | NA | NA | NA | NA | >5 m |
| G5-PAMAM-PEG-$2_{128}$ | 1.4 ± 0.7 (0.7-2.1) n = 3 | 4.0 ± 0.4 (3.7-4.5) n = 3 | 0.7 ± 0.2 (0.8-0.9) n = 3 | 0.4 ± 0.1 (0.4-0.5) n = 3 | 8.4 ± 1.3 (7.0-10.2) n = 4 |
| G5-PAMAM-PEG-$4_{128}$ | 2.4 ± 0.6 (1.9-3.1) n = 3 | 4.1 ± 0.3 (3.7-4.4) n = 3 | 0.9 ± 0.1 (0.8-0.9) n = 3 | 0.4 ± 0.1 (0.4-0.5) n = 3 | 13.9 ± 2.9 (11.3-17.9) n = 4 |
| G5-PAMAM-PEG-$8_{128}$ | 1.7 ± 05 (1.4, 2.2) n = 2 | 3.8 ± 1.1 (3.0, 4.6) n = 2 | 0.7 ± 0.1 (0.6, 0.8) n = 2 | 0.5 ± 0.2 (0.4, 0.6) n = 2 | 11.5 ± 1.6 (10.2-13.3) n = 3 |
| G5-PAMAM-PEG-$12_{128}$ | 2.1 ± 0.1 (2.0, 2.1) n = 2 | 4.6 ± 1.4 (3.6, 5.6) n = 3 | 0.9 ± 0.2 (0.7, 1.0) n = 3 | 0.4 ± 0.1 (0.4, 0.5) n = 3 | 18.1 ± 3.7 (15.8-22.4) n = 3 |
| G6-PAMAM-PEG-$4_{128}$ | 1.7 ± 1.0 (1.0, 2.4) n = 2 | 1.7 ± 0.0 (1.7, 1.7) n = 2 | 0.9 ± 0.3 (1.2, 0.7) n = 2 | 0.2 ± 0.1 (0.1, 0.3) n = 2 | 25.2 ± 5.9 (19.6-33.5) n = 4 |

A second concern with large molecular weight carriers is lack of penetration into the tumor. This proved not to be an issue for the capped PAMAM dendrimers, with diffuse tumor penetration observed on gross histology for all dendrimers tested in HT-1080 xenografts. Other organs showed a very characteristic pattern of uptake with the different caps. For example, acetyl coated dendrimers were taken up by kidney, succinate coated dendrimers were taken up by liver, kidney and spleen, and PEG coated dendrimers showing diffuse uptake into all organs including tumor (FIG. 34).

Example 7: Attaching Selective Transport Molecules to Dendrimeric Nanoparticles

In this example, we have designed a targeted dual labeled probe that can sense and target protease activity in vivo by attaching several selective transport molecules to a dendrimer, and have tested their ability to highlight infiltrative tumor in mice using both whole animal optical, MRI and histological techniques.
Synthesis Briefly, peptides were synthesized with a C-terminal cysteine and attached to the PAMAM dendrimer via a maleimide linkage. After attachment of the peptide, approximately three cy5 molecules or 15-20 DOTA were attached to the dendrimer via an amide linkage. Finally, the remaining amino groups were capped with PEG-4. For constructs with no cy5, chelation of gadolinium was done in glycine buffer (pH 6) at 80 degrees Celcius for three hours. For constructs with the dual label, cold chelation of gadolinium was necessary (ammonium acetate buffer, pH 6 overnight). In all three cases, purification was done by centrifugation through a membrane with a 10 kD molecular weight cut-off. For cy5 labeled constructs, concentration of the dendrimer was assessed by total weight of the compound. The number of Cy5's per dendrimer was assessed by comparing the concentration of dendrimer to the absorbance of Cy5. For gadolinium labeled constructs, the concentration of dendrimer was assessed by weight and the concentration of gadolinium was assessed by inductively coupled plasma mass spectroscopy, both immediately post synthesis and at the time of injection. Wherever possible, purity was independently assessed by tricine gel electrophoresis and was found to be near 100%.
Animals.

Nude mice harboring HT-1080 tumors (3-8 mm) and Transgenic PyMT mice were uses.
Optical Imaging.

Animals were anesthetized with 80 mg/kg ketamine and 40 mg/kg midazolam. One to three nmol of each probe was injected intravenously. Animals were imaged at 1 s and at 3 s using a Maestro spectral deconvolution imager (700 nm) using a 640/48 excitation filter (CRI, Boston, Mass.) for up to one hour following the original injection. Following imaging, animals were returned to their cages and warmed using delta phase pads. At 6 h, 24 h and 48 h, animals were re-anesthetized and imaged. After 48 hours, animals were sacrificed, organs harvested and tissues frozen.
Optical Standardized Uptake Values.

Frozen tissues were defrosted and a representative 30 mg sample cut in the absence of fluorescence guidance. For some tumors known to be heterogeneous such as the PyMT tumors, two to three such 30 mg samples were processed separately and averaged. Each 30 mg slice of tissue was then added to 100 µL SDS lysis buffer (1% SDS, 20 mM Tris buffer, pH 7.6), ground using a disposable pestle and heated to 80° C. for 10 m. To ensure cell lysis, samples were then microwaved twice for 4 seconds. To ensure equal treatment of samples, tubes were centrifuged for 10 minutes, frozen and imaged while frozen using a Maestro spectral deconvolution imager. Integrated intensities were calculated using Image J. Due to variations in the number of cy5 labels per dendrimer, two point calibrations were done for each conjugate separately. Standards were prepared by cutting 30 mg samples from tumor, liver, kidney and muscle from uninjected animals, spiking them with 100 nM final concentration of the injected peptide and processing them as before. Based on concentration curves from one of the conjugates, linearity of signal with concentration was assumed. Standardized uptake values (SUV) are defined as (nmol cy5/30 mg tissue)/(total nmol injected/total weight animal).
Fluorescence Histology.

Sections were cut at 20 µm for HT1080 and PyMT tumors and 25 mm for PyMT metastases then examined using a Zeiss Lumar dissecting microscope (exposure times 5-15 s, ex 620/60, em 700/75). For in situ zymography, DQ gelatin was obtained from EMD and processed as per the manufacturer's instructions. Serial sections were stained using a standard hematoxylin and eosin procedure.
MR Imaging.

Animals were anesthetized and injected as described for optical imaging. At 48 hours, animals were taken to UCSD's 7T magnet, anesthetized using isofluorane (3% loading dose, 1% maintenance dose) and imaged using a T1 weighted RARE (Tr=2595 ms, Te=7.5 ms, NEX=10, slice thickness 0.3 mm, acquisition matrix 256×256), a T1 weighted MSME (Tr=498 ms, Te=8 ms, 10 NEX, slice thickness 0.3 mm, acquisition matrix 128×256) and a Tru-FISP (single slice, slice thickness 0.5 mm, Tr=3, Te=1.5 ms, 4 NEX, acquisition matrix 128×128) to obtain T1's. MR imaging data was processed using either Paravision (Brucker) or Amira 4.1.1 (Mercury).
Gadolinium Standardized Uptake Values.

Following the 48 hour imaging session, animals were sacrificed and tissues removed and frozen. They were then defrosted, weighed, dissolved in nitric acid and sent away to West Coast Analytical Services (Santa Fe Springs, Calif.) for quantitative gadolinium analysis using ICP-MS. Two microliters of the injectate was processed similarly and sent away for quantitative analysis as well. Standardized uptake values (SUV) are defined as (nmol gadolinium/weight tissue)/(total nmol injected/total weight animal).
Selective Transport Molecules Conjugated to Dendrimeric Nanoparticles have More Favorable Biodistribution in Nude Animals than Free Selective Transport Molecules.

To determine whether carrier attached selective transport molecules retain their ability to be selectively cleaved in tumors, two constructs were synthesized and tested for purity using HPLC and fluorescence gel electrophoresis. The first was a dendrimer linked to a cleavable peptide via a maleimide linker at the C-terminal end of the peptide. The second was a similar compound with an all-d-amino acid peptide to serve as a control (FIG. 35a). When the new selective transport molecules conjugated to dendrimeric nanoparticles were injected into nude xenografted animals, skin florescence was greatly diminished, joint uptake largely disappeared and the tumor to thorax ratio increased dramatically, sometimes reaching as high as six-fold (FIG. 35b-d). Furthermore, the fluorescence remained present for as much as 48 hours, whereas by that time most of the free selective transport molecule had washed out (FIG. 35d). The plasma halflife for the new molecules increased to approximately 9 hours, compared to less than 10 minutes for the free peptide based probes. Quantitative analysis and comparison to a d-amino acid control peptide indicated that about half of the signal present was due to enhanced permeability and retention alone (Tumor SUV was 1.8±0.6, n=8 for the cleavable peptide vs. 0.9±0.3, n=5 for the uncleavable peptide). In contrast, tumor SUV at six hours was already down to 0.2±0.0 (n=3) for the cleavable free peptide (suc-e8-OPLG-C(me)-AG-r9-c(cy5)) after six hours, p<0.05 in both cases (FIG. 35f).

Selective Transport Molecules Conjugated to Dendrimeric Nanoparticles are Taken Up by Small Regions of Residual Tumor in a Spontaneous Breast Cancer Model.

We next tested the selective transport molecules conjugated to dendrimeric nanoparticles in the PyMT breast cancer model. While nude animals bearing HT-1080 xenografts have well-encapsulated tumors, the more invasive PyMT model provided us with an opportunity to determine whether our probes could detect even tiny regions of residual tumor invading muscle following tumor debulking (FIG. 36a-c). FIG. 36d shows histological analysis of a single, 200 µm piece of residual tumor directly adjacent to the pectoralis muscle. As in previous experiments, most of the uptake occurs at the stromal interface between tumor and muscle. Finally, we were able to show using standardized uptake values that approximately 33% of the uptake was due to cleavage, with the other 66% being due to enhanced permeability and retention (1.5±0.3, n=6 for the cleavable probe vs. 1.0±0.3, n=5 for the uncleavable probe, p<0.05) (FIG. 36e). A single MMTV-PyMT animal homozygous null for both MMP-2 and MMP-9 gave a tumor standardized uptake value of 0.9, indicating that MMP-2 and -9 are likely responsible for cleavage (data not shown).

Selective Transport Molecules Conjugated to Dendrimeric Nanoparticles Represent an improvement on currently available optical dequenching technology.

To test whether our new optical probes represented an improvement upon currently used technology, we compared uptake of our selective transport molecules conjugated to dendrimeric nanoparticles to uptake and dequenching of a commonly used dequenching probe (Prosense, VisEn Medical) in the same PyMT animal model. Not only did our probes give stronger overall signal with less liver fluorescence (FIG. 37a-c), we also were able to show a statistically significant improvement in tumor to muscle ratios in PyMT mice (FIG. 37d). Furthermore, when it came to imaging metastases in lung, our probes were easily able to detect small (<200 µm) metastases, with about half of the signal coming from bright macrophages surrounding the micrometastasis and the other half of the signal coming from the micrometastasis itself (FIG. 37e-g). In contrast, Prosense mostly stained the middle portion of metastases, leaving the edge largely unstained and hardly stained smaller metastases at all (FIG. 37h-j). Quantification for lung is shown in FIGS. 37H and L. Since Prosense targets cathepsins, we also looked at an analogous probe targeting extracellular MMP's. Though we were able to reproduce the results reported in the literature for MMP-sense, we found that the exposure times were five times longer than for either Prosense or for the selective transport molecules conjugated to dendrimeric nanoparticles, and that the contrast generated in the PyMT model was poorer than for Prosense (data not shown).

Selective Transport Molecules Conjugated to Dendrimeric Nanoparticles can Deliver Gadolinium to Tumors in Sufficient Quantities for T1 MRI.

One of the theoretical advantages to selective transport molecules conjugated to dendrimeric nanoparticles is the ability to connect them to different payload molecules. To address potential concerns about solubility, we attached only 15-30 gadolinium molecules per dendrimer and added more soluble polyethylene glycol moieties. To address the problem of highly variable tumors in PyMT mice, we switched back to HT-1080 xenografts. A series of phantoms was added to account for interscan variation; for quantification, all intensities are normalized to an adjacent water phantom. With gadolinium present in tissue, we expected to see a decrease in T1 correlated to an increase in intensity in tumors from gadolinium injected mice relative to the uninjected controls. Indeed, at 48 hours, the T1 for the tumor had dropped by 22%, with the intensity rising by 15% (FIG. 38a-d). This is consistent with the presence of 30-40 µM gadolinium in tumor, as measured independently using inductively coupled plasma mass spectroscopy. In contrast, the concentration of gadolinium in animals injected with the all-d-amino acid negative control was significantly lower (FIG. 38e, p<0.05). Although these changes are not huge, correlation of a statistically significant increase in signal intensity to a decrease in T1 and the presence of gadolinium confirms that the difference is real, and that probe is being targeted to tumors as hypothesized previously.

A Dual Label Probe Verifies that Uptake was Concentrated in MMP-Producing Regions of Inflammation at the Tumor/Stromal Interface.

One occasional but notable feature of the MRI images from animals injected with cleavable probe was the presence of bright edges surrounding the tumors, sometimes tunneling into neighboring parenchyma. To determine whether these bright edges were significant, a dual labeled probe with both gadolinium and cy5 was synthesized and injected into HT-1080 tumor bearing animals. The animals were imaged both by MRI and fluorescence (FIGS. 39a and b), sacrificed and a small piece of the bright region removed and frozen for histology. On histology, it was clear that two types of uptake were present. As expected, diffuse uptake occurred throughout the tumor parenchyma. However, much of this uptake was obscured by the presence of very bright spots in regions where tumor invaded muscle, providing a histological correlate to what was seen on MR (FIG. 39c). In situ zymography and hematoxylin eosin staining was used to investigate the cause of these bright spots, and as expected, they correlated with the presence of MMP producing macrophages (FIG. 39d-f). In tumors that were better encapsulated and less infiltrative, these bright spots were absent, both using fluorescence imaging and on T1 weighted MRI.

Example 8: Visualization of Tumor Margins

In this example we investigate whether tumor margins could be visualized more objectively during surgery utilizing selective transport molecules. We compared residual tumor cells at the surgical bed and tumor free survival for surgery with and without selective transport molecule molecular guidance.

Animals

Xenografts with HT1080 human fibrosarcoma cells (ATCC) or MDA-MB 435 human melanoma cells were used. Allografts were generated in the lab with 8119 murine mammary adenocarcinoma cells and B16F10 murine melanoma cells. $1 \times 10^6$ cells (either 8119 or BI6F10) were injected intramuscularly into the left flank of albino C57BL/6 mice. Tumor allografts were monitored until tumor size was approximately 1 cm in largest diameter (approximately 7-10 days).

Fluorescent Optical Imaging

Fluorescent optical imaging were performed either with a fluorescent dissecting microscope (Lumar, Zeiss (GFP:

exposure times 1.5-1 s, ex470/40 nm; em525/50 nm; Cy5: exposure times 1.5-1 s, ex620/60 nm; em700/75 nm)) or with the OV100 Small Animal Imaging System (Olympus (GFP: exposure times 0.5-1 s, ex475/40; em 530/50; Cy5: exposure times 1.5-3 s, ex620/60 nm; em700/75 nm).

Fluorescence Uptake

Briefly 30 mg tissues was homogenized and heated in SDS buffer, frozen, and then imaged by fluorescence. SUV ((moles/g tissue)/(moles injected/weight of the animal)) values were determined by comparing experimental fluorescence to standard curves derived by peptide spiked tissue processed similarly.

Survival Surgery

Survival surgeries were performed on allografts with 8110 cells or B16F10 cells generated as detailed above. Animals were anesthetized with 80 mg/kg ketamine and 40 mg/kg midazolam. Following hair removal with depilatory cream, animals were prepped and draped in sterile fashion. Following skin incision over the tumor, skin flaps were developed bluntly and retracted. Tumor excision was performed with microsurgical instrumentations under a dissecting microscope (Lumar, Zeiss) with white light illumination. Hemostasis was achieved with handheld cautery (Accu-Temp, Medtronic). Following complete tumor removal as assessed by while light illumination, animals are randomized into either the Cy5 fluorescence guidance arm or the standard surgery with no molecular guidance arm. Animals that were in the selective transport molecule guidance arm were injected with Cy5 labeled dendrimer selective transport molecule (2 nmoles) 48 hours prior to the beginning of tumor excision. In an attempt to account for bias during initial surgery, the operating surgeon was semi-blinded as to the treatment arms that the animals receive after the initial tumor removal. Semi-blinding in this case meant that the operating surgeon made a conscious effort to not identify animals by which treatment arms they are subsequently going into. However, because it was occasionally the same person who treated the animals with selective transport molecules via tail vein injections as the person who did the tumor resection, animal identification via visual characteristics of individual animals were sometimes unavoidable.

Following complete tumor excision as assessed by white light illumination, the surgical field was then assessed through the dissecting scope with excitation and emission parameters for Cy5. Images of the fluorescence signal were displayed on an adjacent monitor and all Cy5 positive tissue foci were excised. Following completion of tumor removal either with or without fluorescence guidance, skin incisions were repaired with interrupted simple sutures (6-0 Silk, Ethicon) and animals were returned to their cages to recover from the anesthesia.

Animals were examined for tumor recurrence 3 times per week. All animals were sacrificed regardless of presence or absence of tumor recurrence at six months following surgery. Quantification of residual tumor cells Animals used for quantification of residual tumor cells after surgery were performed on xenograft of HT1080 cells generated as detailed above. Animals were anesthetized with 80 mg/kg ketamine and 40 mg/kg midazolam. Following skin incision and retraction, tumors were removed with microsurgical technique using a dissecting microscope (Zeiss, Lumar).

Fluorescence guidance of tumor excision was performed as detailed above for the survival studies with GFP, free selective transport molecule (10 nmoles; 6 hours prior to surgery) or dendrimer selective transport molecule (2 nmoles; 48 hours prior to surgery). For animals in the GFP guidance arm, the surgical field was assessed through the dissecting scope with excitation and emission parameters for GFP. Images of the fluorescence signal were displayed on an adjacent monitor and all GFP positive tissue foci were excised. Treatment of the animals in the selective transport molecule arms were performed as in the survival surgeries described above. Following completion of tumor resection, the remaining surgical bed was resected with at least a 5 mm margin in all contiguous dimensions and analyzed for Alu sequences. Alu PCR analysis of the remaining surgical bed for residual tumor cells were performed. Because the PCR assay measures the number of cycles necessary to reach detectability, which is proportional to the log of the amount of source DNA, residual tumor DNA is represented in log units.

Fluorescence and MR Imaging with Dual-Labeled ACPP

HT1080 xenografts were generated as described above. Preoperative MR imaging of the mice were performed. Mice were then anesthetized and tumor removed with fluorescence guidance as described above. Following complete tumor removal, mice were brought to MR imaging suite and postoperative MR scans were obtained. Tumor volume was quantified three dimensionally by hand using Amira software (Mercury, Carlsbad, Calif.). Tumor volume quantification using preoperative and postoperative images were done in a blinded fashion by separate personnel.

Tumor Imaging with Cy5-Labeled ACPP

To test whether selective transport molecules are taken up differentially between tumor and normal tissue, allografts derived from spontaneous mammary adenocarcinoma tumors in transgenic mice (line 8119, MMTV-PyMT) and the murine melanoma cell line B16F10 transplanted into immune competent mice, and human cancer cell lines (MDA-MB 435 melanoma and HT1080 fibrosarcoma) xenografted into nude mice, were imaged after intravenous injection of Cy5-labeled selective transport molecules and sufficient time for elimination of uncleaved selective transport molecules. Cy5 was chosen as a labeling marker because of its reduced tissue absorption in the near infrared range. We tested both isolated selective transport molecule peptides (free selective transport molecule) and selective transport molecule peptides conjugated to PAMAM dendrimer (dendrimer selective transport molecule). We found that all tumors retain the Cy5 labeled free selective transport molecule and dendrimer selective transport molecule to a greater extent than normal tissues or to either tissue treated with uncleavable peptides. Furthermore, we found that tumor to normal tissue ratio from all tumor types were greater with dendrimer selective transport molecule compared to free selective transport molecule (Table 2).

TABLE 2

|  |  | Free Selective Transport Molecules | Dendrimer Selective Transport Molecules |
|---|---|---|---|
| MDA-MB 435 | Tumor | 0.17 ± 0.05 (n = 3) | 1.065 ± 0.55 (n = 3) |
|  | Muscle | 0.29 ± 0.068 (n = 3) | 0.238 ± 0.007 (n = 3) |
|  | Ratio | 2.45 (p = 0.0004) | 4.46 (p = 0.031) |

TABLE 2-continued

|  |  | Free Selective Transport Molecules | Dendrimer Selective Transport Molecules |
|---|---|---|---|
| HT1080 | Tumor | 0.42 ± 0.08 (n = 4) | 1.8 ± 0.6 (n = 8) |
|  | Muscle | 0.11 ± 0.08 (n = 4) | 0.21 ± 0.07 (n = 8) |
|  | Ratio | 3.82 (p = 0.022) | 8.6 (p = 0.0009) |
| 8119 | Tumor | 0.39 ± 0.12 (n = 5) | 2.191 ± 0.743 (n = 3) |
|  | Muscle | 0.11 ± 0.06 (n = 5) | 0.166 ± 0.023 (n = 3) |
|  | Ratio | 3.5 (p = 0.006) | 13.2 (p = 0.004) |
| B16F10 | Tumor | 0.24 ± 0.06 (n = 4) | 1.069 ± 0.575 (n = 3) |
|  | Muscle | 0.10 ± 0.03 (n = 3) | 0.191 ± 0.014 (n = 3) |
|  | Ratio | 2.4 (p = 0.014) | 5.6 (p = 0.028) |

Selective Transport Molecules Delineate Tumor at the Margin of Resection.

To assess the ability of selective transport molecules to delineate the margin between normal and tumor tissue, we injected nude mice xenografted with the GFP-transfected cell line MDA-MB 435 intravenously with Cy5 labeled free selective transport molecule prior to surgical excision of tumors. We found that if the tumors were well encapsulated, standard surgical technique without selective transport molecule guidance resulted in complete tumor removal (as evidenced by GFP fluorescence and histological analysis) and selective transport molecule guidance did not improve efficacy of surgical excision (data not shown). However, if the tumors were infiltrative into surrounding tissue, selective transport molecule guidance resulted in the ability to visualize areas of tumors that are not apparent with white light (either from being buried beneath other tissue or where the appearance of the tumor is not easily distinguishable from surrounding normal tissue).

Comparing Free- and Dendrimer-Selective Transport Molecule for Fluorescence Imaging Guidance To assess the utility of free-selective transport molecule vs. dendrimeric-selective transport molecule for fluorescence imaging guidance during surgery for tumor resection, we injected either version of the peptides fluorescently labeled with Cy5 into mice xenografted with GFP-transfected MDA-MB 435. We compared free-selective transport molecules and dendrimer-selective transport molecules for their tumor to background visual fluorescence contrast and ease of use during in vivo surgery (n=16 each condition). We found that there is a higher tumor to background fluorescence contrast for the dendrimer-selective transport molecule compared to free-selective transport molecules and higher absolute tumor fluorescence for dendrimer-selective transport molecules when normalized to the amount of fluorophore injected. Treatment with dendrimeric-selective transport molecules has been shown to result in higher fluorescence uptake by the tumor (Table 2) with less non-specific uptake by skin and cartilage. We did note limited fluorescence uptake for both free and dendrimeric selective transport molecule into lymph nodes as well as fatty tissue that is not dependent on the presence of cancer cells. This is likely due to non-specific uptake by macrophages, whose presence is abundant in both of these tissues.

Residual Tumor Cell Quantification with Alu PCR

To quantify the efficacy of tumor excision with selective transport molecule guidance, we used Alu PCR to measure residual human (cancer) cells remaining in the tumor bed after surgical excision. The quantification of human Alu sequences has been shown to be able to detect the equivalent of one human tumor cell in $1 \times 10^6$ murine cells. Tumor margins can thus be detected sensitively using human Alu PCR. We found that dendrimer selective transport molecule guidance resulted in ten-fold fewer residual tumor cells at the surgical site (i.e. 90% reduction of residual cancer cells) (log[DNA]=3.67±0.47, n=10) compared to unguided surgery done using standard technique (log [DNA]=4.63±0.82, n=10, 2-tailed Student's t test, p=0.005). In contrast, surgery using GFP fluorescence inherent to the cancer cells to guide excision (log [DNA]=4.0±1.4, n=7) or surgery with free selective transport molecule (log[DNA]=4.67±0.33, n=6) did not show improved efficacy compared to standard unguided surgery (log[DNA]=4.63±0.82, n=10, p=0.26 and 0.91, respectively). We hypothesize that cells within the xenografts lose GFP expression due to selective pressures and thus some cancer cells may be missed during GFP fluorescence survey of the tumor bed, resulting in incomplete resection of the tumor. In addition, because GFP fluorescence is absorbed by tissue and hemoglobin in the living animal, tumors that are not on the surface of the surgical bed may be missed. The lack of improved cancer removal efficacy with free selective transport molecule guidance likely reflects the lower free selective transport molecule uptake by tumor tissue and thus reduced contrast of the free selective transport molecule between tumor and adjacent normal tissue (2.45 fold) compared to dendrimer selective transport molecules (4.46 fold). Consistent with this observation, there is a significant reduction of residual tumor cells using dendrimer selective transport molecule guidance compared to free selective transport molecule guidance (2 tailed Student's t test, p=0.0005).

Histological Analysis of Surgical Specimens Derived from ACPP-Guided Surgery

To quantify correlation between high fluorescence uptake and presence of malignant cells, we performed histological analysis on individual ACPP-guided resected samples. We found that the dendrimer-selective transport molecule probe has a specificity rate of 93.33% (i.e. H&E histological analysis showed cancer cells in 14 of 15 specimens obtained from dendrimer-selective transport molecule guided excision).

Dendrimer-Selective Transport Molecule Guided Surgery Resulted in Smaller Residual Tumor Volume by MRI To compare the volume of residual tumor volume following dendrimer selective transport molecule guided surgery versus standard unguided surgery, we performed MR imaging of mice xenografted with HT1080 cells treated with dendrimer-selective transport molecule containing both Cy5 and Gadolinium chelate. Tumor volume was quantified using the MR images before and after fluorescence guided selective transport molecule excision of tumor in a blinded fashion. We found that surgery with Cy5 selective transport molecule fluorescence guidance resulted in approximately a 5-fold reduction of residual tumor based the volumetric analysis of MRI scan compared to standard unguided surgery (0.003±0.002 mm$^3$ (n=2) vs. 0.016±0.008 mm$^3$ (n=2)).

Although this result did not reach statistical significance, (Student's t test, 1 tailed, p=0.08) likely because of the small sample size, it is consistent with the above result showing reduced residual tumor cells by Alu PCR quantification.

Improved Tumor Free Survival with Selective Transport Molecule Guided Surgery

To test whether tumor recurrence is affected when surgery is done with selective transport molecule guidance, we injected Cy5-labeled dendrimer selective transport molecule into immunocompetent mice allografted with cells derived either from spontaneous tumors in transgenic mice (line 8119, MMTV-PyMT) or from the melanoma cell line (B16F10). When the tumors were well encapsulated, complete tumor excision was accomplished with and without selective transport molecule guidance and thus selective transport molecule guidance did not confer any additional survival benefit (data not shown). However, when the tumors were infiltrative into surrounding tissue, we found that mice whose tumors were excised with dendrimer selective transport molecule guidance showed improved tumor free survival compared to mice whose tumors were excised without dendrimer selective transport molecule guidance. In mice allografted with the melanoma cell line B16F10, surgery with dendrimer selective transport molecule guidance resulted in a doubling of improved tumor free survival in the short term (40% compared to 20% at 8 weeks following surgery) and a 50% improvement of tumor free survival at longer times (33% compared to 22% at 24 weeks, Wilcoxon test, p=0.05). In mice allografted with the transgenic 8119 breast cancer cell line, surgery with dendrimer selective transport molecule guidance resulted in 5 fold improvement of long term (24 weeks) tumor-free survival compared to standard surgery (50% compared to 10% at 20 weeks following surgery, Wilcoxon test, p=0.03).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A molecule comprising a structure A-X-B-C, wherein:
A is a peptide with (i) a sequence comprising a series of 5 to 9 acidic amino acids selected from: aspartates and glutamates, and (ii) an unsubstituted maleimide bound to the N-terminus of the peptide;
B is a peptide with a sequence comprising a series of 5 to 20 basic amino acids;

X is a cleavable linker selected from: PLGLAG (SEQ ID NO:1), PLGLAx (SEQ ID NO:2) wherein X is any amino acid, PLG-C(me)-AG (SEQ ID NO:3), ESPAYYTA (SEQ ID NO:4), RLQLKL (SEQ ID NO:5), and RLQLK(AC) (SEQ ID NO:6); and C is a chemotherapeutic agent.

2. The molecule of claim 1, wherein the unsubstituted maleimide is attached to the N-terminus of A through a linker.

3. The molecule of claim 2, wherein the linker comprises a heterobifunctional linker.

4. The molecule of claim 2, wherein the linker further comprises a hydrophilic PEG chain.

5. The molecule of claim 2, wherein the linker further comprises a hydrophobic carbon chain.

6. The molecule of claim 1, wherein A has a sequence comprising a series of 5 to 9 glutamates.

7. The molecule of claim 1, wherein A has a sequence comprising a series of 9 glutamates.

8. The molecule of claim 1, wherein A has a sequence comprising a series of 5 glutamates.

9. The molecule of claim 1, wherein B has a sequence comprising a series of 5 to 12 arginines.

10. The molecule of claim 1, wherein B has a sequence comprising a series of 9 arginines.

11. The molecule of claim 1, wherein B has a sequence comprising a series of 8 arginines.

12. The molecule of claim 1, wherein A and B comprise D-amino acids.

13. A pharmaceutical composition comprising the molecule of claim 1 and a pharmaceutically acceptable carrier.

* * * * *

SEQUENCE LISTING

```
<160> NUMBER OF SEQ ID NOS: 51

<210> SEQ ID NO 1
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 1

Pro Leu Gly Leu Ala Gly
1               5

<210> SEQ ID NO 2
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (6)..(6)
<223> OTHER INFORMATION: Xaa = any amino acid

<400> SEQUENCE: 2

Pro Leu Gly Leu Ala Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (4)..(4)
<223> OTHER INFORMATION: METHYLATION

<400> SEQUENCE: 3

Pro Leu Gly Cys Ala Gly
1               5
```

```
<210> SEQ ID NO 4
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 4

Glu Ser Pro Ala Tyr Tyr Thr Ala
1               5

<210> SEQ ID NO 5
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 5

Arg Leu Gln Leu Lys Leu
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (5)..(5)
<223> OTHER INFORMATION: ACETYLATION

<400> SEQUENCE: 6

Arg Leu Gln Leu Lys
1               5

<210> SEQ ID NO 7
<211> LENGTH: 19
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (8)..(8)
<223> OTHER INFORMATION: Xaa = aminocaproic acid
<220> FEATURE:
<221> NAME/KEY: MOD_RES
<222> LOCATION: (18)..(18)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = cysteinamide modified by fluorescein

<400> SEQUENCE: 7

Glu Asp Asp Asp Asp Lys Ala Xaa Arg Arg Arg Arg Arg Arg Arg
1               5                   10                  15

Arg Xaa Xaa

<210> SEQ ID NO 8
<211> LENGTH: 22
<212> TYPE: PRT
<213> ORGANISM: Artificial Sequence
<220> FEATURE:
<223> OTHER INFORMATION: selective transport molecule
<220> FEATURE:
<221> NAME/KEY: MOD_RES
```

```
<222> LOCATION: (1)..(1)
<223> OTHER INFORMATION: Xaa = aminocaproic acid modified by fluorescein
<220> FEATURE:
<221> NAME/KEY: MOD_RES
<222> LOCATION: (12)..(12)
<223> OTHER INFORMATION: Xaa = aminocaproic acid
<220> FEATURE:
<221> NAME/KEY: MOD_RES
<222> LOCATION: (22)..(22)
<223> OTHER INFORMATION: Xaa cysteinamide

<400> SEQUENCE: 8

Xaa Cys Arg Arg Arg Arg Arg Arg Arg Arg Xaa Glu Glu Glu Glu
1               5                   10                  15

Glu Glu Glu Glu Glu Cys
            20

<210> SEQ ID NO 9
<211> LENGTH: 17
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: Xaa = aminocaproic acid modified by fluorescein
<220> FEATURE:
<221> NAME/KEY: MOD_RES
<222> LOCATION: (7)..(7)
<223> OTHER INFORMATION: Xaa = aminocaproic acid
<220> FEATURE:
<221> NAME/KEY: MOD_RES
<222> LOCATION: (17)..(17)
<223> OTHER INFORMATION: cysteinamide
<220> FEATURE:
<221> NAME/KEY: MOD_RES
<222> LOCATION: (17)..(17)
<223> OTHER INFORMATION: Xaa = cysteinamide

<400> SEQUENCE: 9

Xaa Cys Glu Glu Glu Glu Xaa Arg Arg Arg Arg Arg Arg Arg Arg
1               5                   10                  15

Cys

<210> SEQ ID NO 10
<211> LENGTH: 23
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (12)..(12)
<223> OTHER INFORMATION: Xaa = aminocaproic acid
<220> FEATURE:
<221> NAME/KEY: MOD_RES
<222> LOCATION: (22)..(22)
<223> OTHER INFORMATION: Xaa = aminocaproic acid
<220> FEATURE:
<221> NAME/KEY: MOD_RES
<222> LOCATION: (23)..(23)
<223> OTHER INFORMATION: Xaa = cysteinamide modified by fluorescein

<400> SEQUENCE: 10

Glu Glu Glu Glu Glu Asp Asp Asp Asp Lys Ala Xaa Arg Arg Arg
1               5                   10                  15

Arg Arg Arg Arg Arg Xaa Xaa
            20
```

```
<210> SEQ ID NO 11
<211> LENGTH: 19
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (8)..(8)
<223> OTHER INFORMATION: Xaa = aminocaproic acid
<220> FEATURE:
<221> NAME/KEY: MOD_RES
<222> LOCATION: (18)..(18)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = cysteinamide modified by fluorescein

<400> SEQUENCE: 11

Glu Asp Asp Asp Asp Lys Ala Xaa Arg Arg Arg Arg Arg Arg Arg
1               5                   10                  15

Arg Xaa Xaa

<210> SEQ ID NO 12
<211> LENGTH: 22
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (21)..(21)
<223> OTHER INFORMATION: Xaa = aminocaproic acid linker
<220> FEATURE:
<221> NAME/KEY: MOD_RES
<222> LOCATION: (22)..(22)
<223> OTHER INFORMATION: Xaa = cysteinamide modified by fluorescein

<400> SEQUENCE: 12

Glu Glu Glu Glu Glu Asp Asp Asp Asp Lys Ala Arg Arg Arg Arg
1               5                   10                  15

Arg Arg Arg Arg Xaa Xaa
                20

<210> SEQ ID NO 13
<211> LENGTH: 19
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (18)..(18)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = cysteineamide modified by fluorescein

<400> SEQUENCE: 13

Asp Asp Asp Asp Asp Asp Lys Ala Arg Arg Arg Arg Arg Arg Arg
1               5                   10                  15

Arg Xaa Xaa

<210> SEQ ID NO 14
<211> LENGTH: 23
<212> TYPE: PRT
<213> ORGANISM: Artificial Sequence
<220> FEATURE:
```

```
<223> OTHER INFORMATION: synthetic polypeptide
<220> FEATURE:
<221> NAME/KEY: MOD_RES
<222> LOCATION: (10)..(10)
<223> OTHER INFORMATION: Xaa = aminocaproic acid
<220> FEATURE:
<221> NAME/KEY: MOD_RES
<222> LOCATION: (13)..(13)
<223> OTHER INFORMATION: Xaa = aminocaproic acid
<220> FEATURE:
<221> NAME/KEY: MOD_RES
<222> LOCATION: (16)..(16)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = aminocaproic acid
<220> FEATURE:
<221> NAME/KEY: MOD_RES
<222> LOCATION: (22)..(22)
<223> OTHER INFORMATION: Xaa = aminocaproic acid
<220> FEATURE:
<221> NAME/KEY: MOD_RES
<222> LOCATION: (23)..(23)
<223> OTHER INFORMATION: Xaa = cysteinamide modified by fluorescein

<400> SEQUENCE: 14

Glu Glu Asp Asp Asp Asp Lys Ala Arg Xaa Arg Arg Xaa Arg Arg Xaa
1               5                   10                  15

Arg Arg Xaa Arg Arg Xaa Xaa
            20

<210> SEQ ID NO 15
<211> LENGTH: 11
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (4)..(4)
<223> OTHER INFORMATION: Xaa = aminocaproic acid
<220> FEATURE:
<221> NAME/KEY: MOD_RES
<222> LOCATION: (10)..(10)
<223> OTHER INFORMATION: Xaa = aminocaproic acid
<220> FEATURE:
<221> NAME/KEY: MOD_RES
<222> LOCATION: (11)..(11)
<223> OTHER INFORMATION: Xaa = cysteinamide modified by fluorescein

<400> SEQUENCE: 15

Glu Asp Ala Xaa Arg Arg Arg Arg Arg Xaa Xaa
1               5                   10

<210> SEQ ID NO 16
<211> LENGTH: 16
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (8)..(8)
<223> OTHER INFORMATION: Xaa = aminocaproic acid
<220> FEATURE:
<221> NAME/KEY: MOD_RES
<222> LOCATION: (15)..(15)
<223> OTHER INFORMATION: Xaa = aminocaproic acid
<220> FEATURE:
<221> NAME/KEY: MOD_RES
<222> LOCATION: (16)..(16)
<223> OTHER INFORMATION: Xaa = cysteinamide modified by doxorubicin
```

```
<400> SEQUENCE: 16

Glu Asp Asp Asp Asp Lys Ala Xaa Arg Arg Arg Arg Arg Xaa Xaa
1               5                   10                  15

<210> SEQ ID NO 17
<211> LENGTH: 23
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (12)..(12)
<223> OTHER INFORMATION: Xaa = aminocaproic acid
<220> FEATURE:
<221> NAME/KEY: MOD_RES
<222> LOCATION: (22)..(22)
<223> OTHER INFORMATION: Xaa = aminocaproic acid
<220> FEATURE:
<221> NAME/KEY: MOD_RES
<222> LOCATION: (23)..(23)
<223> OTHER INFORMATION: Tyr modified by iodination with 125-I and by
      amidation

<400> SEQUENCE: 17

Glu Glu Glu Asp Asp Asp Glu Glu Glu Asp Ala Xaa Arg Arg Arg
1               5                   10                  15

Arg Arg Arg Arg Arg Xaa Tyr
            20

<210> SEQ ID NO 18
<211> LENGTH: 33
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (33)..(33)
<223> OTHER INFORMATION: Xaa = cysteinamide modified by fluorescein

<400> SEQUENCE: 18

Glu Glu Glu Glu Glu Asp Asp Asp Asp Lys Ala Pro Leu Gly Leu Ala
1               5                   10                  15

Gly Arg Arg Arg Arg Arg Arg Arg Arg Pro Leu Gly Leu Ala Gly
            20                  25                  30

Xaa

<210> SEQ ID NO 19
<211> LENGTH: 27
<212> TYPE: PRT
<213> ORGANISM: Artificial Sequence
<220> FEATURE:
<223> OTHER INFORMATION: synthetic polypepide
<220> FEATURE:
<221> NAME/KEY: MOD_RES
<222> LOCATION: (27)..(27)
<223> OTHER INFORMATION: Xaa = cysteinamide modified by fluorescein

<400> SEQUENCE: 19

Glu Glu Glu Glu Glu Asp Asp Asp Asp Lys Ala Arg Arg Arg Arg
1               5                   10                  15

Arg Arg Arg Arg Pro Leu Gly Leu Ala Gly Xaa
            20                  25

<210> SEQ ID NO 20
<211> LENGTH: 29
```

```
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (29)..(29)
<223> OTHER INFORMATION: Xaa = cysteinamide modified by fluorescein

<400> SEQUENCE: 20

Glu Asp Asp Asp Asp Lys Ala Pro Leu Gly Leu Ala Gly Arg Arg
1               5                   10                  15

Arg Arg Arg Arg Arg Arg Pro Leu Gly Leu Ala Gly Xaa
            20                  25

<210> SEQ ID NO 21
<211> LENGTH: 48
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (48)..(48)
<223> OTHER INFORMATION: Xaa = cysteinamide modified by fluorescein

<400> SEQUENCE: 21

Glu Glu Asp Asp Asp Asp Lys Ala Arg Pro Leu Gly Leu Ala Gly Arg
1               5                   10                  15

Arg Pro Leu Gly Leu Ala Gly Arg Arg Pro Leu Gly Leu Ala Gly Arg
            20                  25                  30

Arg Pro Leu Gly Leu Ala Gly Arg Arg Pro Leu Gly Leu Ala Gly Xaa
        35                  40                  45

<210> SEQ ID NO 22
<211> LENGTH: 24
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (24)..(24)
<223> OTHER INFORMATION: Xaa = cysteinamide modified by fluorescein

<400> SEQUENCE: 22

Asp Asp Asp Asp Asp Asp Lys Ala Arg Arg Arg Arg Arg Arg Arg
1               5                   10                  15

Arg Pro Leu Gly Leu Ala Gly Xaa
            20

<210> SEQ ID NO 23
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (3)..(3)
<223> OTHER INFORMATION: Xaa = Ser or Thr
<220> FEATURE:
<221> NAME/KEY: MOD_RES
<222> LOCATION: (4)..(4)
<223> OTHER INFORMATION: Xaa = Leu or Ile
<220> FEATURE:
<221> NAME/KEY: MOD_RES
<222> LOCATION: (5)..(5)
<223> OTHER INFORMATION: Xaa = Ser or Thr
```

<400> SEQUENCE: 23

Pro Arg Xaa Xaa Xaa
1               5

<210> SEQ ID NO 24
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 24

Gly Gly Ala Ala Asn Leu Val Arg Gly Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 25

Ser Gly Arg Ile Gly Phe Leu Arg Thr Ala
1               5                   10

<210> SEQ ID NO 26
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 26

Ser Gly Arg Ser Ala
1               5

<210> SEQ ID NO 27
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 27

Gly Phe Leu Gly
1

<210> SEQ ID NO 28
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 28

Ala Leu Ala Leu
1

<210> SEQ ID NO 29
<211> LENGTH: 5
<212> TYPE: PRT
<213> ORGANISM: Artificial Sequence
<220> FEATURE:
<223> OTHER INFORMATION: synthetic polypeptide
<220> FEATURE:

```
<221> NAME/KEY: MOD_RES
<222> LOCATION: (3)..(3)
<223> OTHER INFORMATION: S-ethylcysteine
<220> FEATURE:
<221> NAME/KEY: MOD_RES
<222> LOCATION: (3)..(3)
<223> OTHER INFORMATION: Xaa = S-ethylcysteine

<400> SEQUENCE: 29

Pro Ile Xaa Phe Phe
1               5

<210> SEQ ID NO 30
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 30

Gly Gly Pro Arg Gly Leu Pro Gly
1               5

<210> SEQ ID NO 31
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 31

His Ser Ser Lys Leu Gln
1               5

<210> SEQ ID NO 32
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 32

Leu Val Leu Ala Ser Ser Ser Phe Gly Tyr
1               5                   10

<210> SEQ ID NO 33
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 33

Gly Val Ser Gln Asn Tyr Pro Ile Val Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 34

Gly Val Val Gln Ala Ser Cys Arg Leu Ala
1               5                   10
```

```
<210> SEQ ID NO 35
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 35

Asp Glu Val Asp
1

<210> SEQ ID NO 36
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 36

Gly Trp Glu His Asp Gly
1               5

<210> SEQ ID NO 37
<211> LENGTH: 11
<212> TYPE: PRT
<213> ORGANISM: Artificial Sequence
<220> FEATURE:
<223> OTHER INFORMATION: JNK Inhibitor VI
<220> FEATURE:
<221> NAME/KEY: MOD_RES
<222> LOCATION: (11)..(11)
<223> OTHER INFORMATION: AMIDATION

<400> SEQUENCE: 37

Arg Pro Lys Arg Pro Thr Thr Leu Asn Leu Phe
1               5                   10

<210> SEQ ID NO 38
<211> LENGTH: 16
<212> TYPE: PRT
<213> ORGANISM: Artificial Sequence
<220> FEATURE:
<223> OTHER INFORMATION: SC 3036

<400> SEQUENCE: 38

Lys Lys His Thr Asp Asp Gly Tyr Met Pro Met Ser Pro Gly Val Ala
1               5                   10                  15

<210> SEQ ID NO 39
<211> LENGTH: 28
<212> TYPE: PRT
<213> ORGANISM: Artificial Sequence
<220> FEATURE:
<223> OTHER INFORMATION: NEMO-Binding Domain Binding Peptide

<400> SEQUENCE: 39

Asp Arg Gln Ile Lys Ile Trp Phe Gln Asn Arg Arg Met Lys Trp Lys
1               5                   10                  15

Lys Thr Ala Leu Asp Trp Ser Trp Leu Gln Thr Glu
            20                  25

<210> SEQ ID NO 40
<211> LENGTH: 26
<212> TYPE: PRT
<213> ORGANISM: Artificial Sequence
<220> FEATURE:
<223> OTHER INFORMATION: NF-kB SN50
```

```
<400> SEQUENCE: 40

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 41
<211> LENGTH: 29
<212> TYPE: PRT
<213> ORGANISM: Artificial Sequence
<220> FEATURE:
<223> OTHER INFORMATION: TIRAP Inhibitor Peptide

<400> SEQUENCE: 41

Arg Gln Ile Lys Ile Trp Phe Asn Arg Arg Met Lys Trp Lys Lys Leu
1               5                   10                  15

Gln Leu Arg Asp Ala Ala Pro Gly Gly Ala Ile Val Ser
            20                  25

<210> SEQ ID NO 42
<211> LENGTH: 4
<212> TYPE: PRT
<213> ORGANISM: Artificial Sequence
<220> FEATURE:
<223> OTHER INFORMATION: caspase-9 inhibitor Z-LEHD-FMK
<220> FEATURE:
<221> NAME/KEY: MOD_RES
<222> LOCATION: (1)..(1)
<223> OTHER INFORMATION: Leu modified by attachment to benzyloxycarbonyl
      group
<220> FEATURE:
<221> NAME/KEY: MOD_RES
<222> LOCATION: (2)..(2)
<223> OTHER INFORMATION: Glu modified by O-methylation
<220> FEATURE:
<221> NAME/KEY: MOD_RES
<222> LOCATION: (4)..(4)
<223> OTHER INFORMATION: Asp modified by O-methylation and by attachment
      to fluoromethyl ketone (FMK)

<400> SEQUENCE: 42

Leu Glu His Asp
1

<210> SEQ ID NO 43
<211> LENGTH: 4
<212> TYPE: PRT
<213> ORGANISM: Artificial Sequence
<220> FEATURE:
<223> OTHER INFORMATION: caspase-9 inhibitor Ac-LEHD-CHO
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: modified by oxidation of the terminal backbone
      carboxyl group to an aldehyde

<400> SEQUENCE: 43

Leu Glu His Asp
1

<210> SEQ ID NO 44
<211> LENGTH: 4
<212> TYPE: PRT
<213> ORGANISM: Artificial Sequence
<220> FEATURE:
```

```
<223> OTHER INFORMATION: caspase-8 inhibitor Ac-IETD-CHO
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: modified by oxidation of the terminal backbone
      carboxyl group to an aldehyde

<400> SEQUENCE: 44

Ile Glu Thr Asp
1

<210> SEQ ID NO 45
<211> LENGTH: 4
<212> TYPE: PRT
<213> ORGANISM: Artificial Sequence
<220> FEATURE:
<223> OTHER INFORMATION: caspase-8 inhibitor Z-IETD-CHO
<220> FEATURE:
<221> NAME/KEY: MOD_RES
<222> LOCATION: (1)..(1)
<223> OTHER INFORMATION: Ile modified by attachment to benzylcarbonyl
      group
<220> FEATURE:
<221> NAME/KEY: MOD_RES
<222> LOCATION: (2)..(2)
<223> OTHER INFORMATION: Glu modified by O-methylation
<220> FEATURE:
<221> NAME/KEY: MOD_RES
<222> LOCATION: (4)..(4)
<223> OTHER INFORMATION: Asp modified by O-methylation and by attachment
      to fluoromethyl ketone (FMK)

<400> SEQUENCE: 45

Ile Glu Thr Asp
1

<210> SEQ ID NO 46
<211> LENGTH: 4
<212> TYPE: PRT
<213> ORGANISM: Artificial Sequence
<220> FEATURE:
<223> OTHER INFORMATION: caspase-9 fluorescent inhibitor FAM-LEHD-FMK
<220> FEATURE:
<221> NAME/KEY: MOD_RES
<222> LOCATION: (1)..(1)
<223> OTHER INFORMATION: Leu modified by attachment to fluorescein
      amidite (FAM)
<220> FEATURE:
<221> NAME/KEY: MOD_RES
<222> LOCATION: (4)..(4)
<223> OTHER INFORMATION: Asp modified by attachment to fluoromethyl
      ketone (FMK)

<400> SEQUENCE: 46

Leu Glu His Asp
1

<210> SEQ ID NO 47
<211> LENGTH: 4
<212> TYPE: PRT
<213> ORGANISM: Artificial Sequence
<220> FEATURE:
<223> OTHER INFORMATION: caspase-8 fluorescent inhibitor FAM-LETD-FMK
<220> FEATURE:
<221> NAME/KEY: MOD_RES
<222> LOCATION: (1)..(1)
<223> OTHER INFORMATION: Leu modified by attachment to fluorescein
      amidite (FAM)
<220> FEATURE:
```

```
<221> NAME/KEY: MOD_RES
<222> LOCATION: (4)..(4)
<223> OTHER INFORMATION: Asp modified by attachment to fluoromethyl
      ketone (FMK)

<400> SEQUENCE: 47

Leu Glu Thr Asp
1

<210> SEQ ID NO 48
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 48

Leu Ala Leu Gly Pro Gly
1               5

<210> SEQ ID NO 49
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 49

Pro Leu Gly Trp Ala Gly
1               5

<210> SEQ ID NO 50
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: Xaa = aminocaproic acid
<220> FEATURE:
<221> NAME/KEY: MOD_RES
<222> LOCATION: (7)..(7)
<223> OTHER INFORMATION: Xaa = aminocaproic acid

<400> SEQUENCE: 50

Xaa Ser Gly Arg Ser Ala Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: cleaving sequence
<220> FEATURE:
<221> NAME/KEY: MOD_RES
<222> LOCATION: (6)..(6)
<223> OTHER INFORMATION: Xaa = aminocaproic acid

<400> SEQUENCE: 51

Pro Leu Gly Leu Ala Xaa
1               5
```